US008926736B2

(12) United States Patent
Serre et al.

(10) Patent No.: US 8,926,736 B2
(45) Date of Patent: Jan. 6, 2015

(54) REDUCIBLE POROUS CRYSTALLINE HYBRID SOLID FOR THE SEPARATION OF MIXTURES OF MOLECULES HAVING DIFFERENT DEGREES AND/OR A DIFFERENT NUMBER OF UNSATURATIONS

(75) Inventors: Christian Serre, Plaisir (FR); Alexandre Vimont, Merville-Franceville (FR); Philip Llewellyn, Marseilles (FR); Jong-San Chang, Daejeon (KR); Patricia Horcajada-Cortes, Chaville (FR); Gérard Ferey, Paris (FR); Marco Daturi, Epron (FR); Young-Kyu Hwang, Daejeon (KR)

(73) Assignees: Centre National de la Recherche Scientifique -CNRS-, Paris (FR); Universite de Caen-Basse Normandie, Caen (FR); Universite de Versailles—Saint Quentin en Yvelines, Versailles (FR); Korea Research Institute of Chemical & Technology (KRICT), Daejeon (KR)

( * ) Notice: Subject to any disclaimer, the term of this patent is extended or adjusted under 35 U.S.C. 154(b) by 788 days.

(21) Appl. No.: 12/996,325

(22) PCT Filed: Jun. 11, 2009

(86) PCT No.: PCT/FR2009/000699
§ 371 (c)(1),
(2), (4) Date: Mar. 4, 2011

(87) PCT Pub. No.: WO2010/000975
PCT Pub. Date: Jan. 7, 2010

(65) Prior Publication Data
US 2011/0172412 A1    Jul. 14, 2011

(30) Foreign Application Priority Data
Jun. 11, 2008   (FR) ..................................... 08 03245

(51) Int. Cl.
*C07C 7/13* (2006.01)
*B01D 53/04* (2006.01)

(52) U.S. Cl.
CPC ... *C07C 7/13* (2013.01); *Y10S 95/90* (2013.01)
USPC ................................ 95/141; 95/143; 95/900

(58) Field of Classification Search
USPC .............................. 95/90, 141, 143, 144, 900
See application file for complete search history.

(56) References Cited

U.S. PATENT DOCUMENTS 6,488,741 B2 * 12/2002 Olson ............................. 95/144
6,517,611 B1 *  2/2003 Kuznicki et al. ................ 95/144
8,425,659 B2 *  4/2013 Matzger et al. ................... 95/96
8,530,717 B2 *  9/2013 Schubert et al. .............. 585/830
2003/0121415 A1 *  7/2003 Olson ............................. 95/144
2009/0312591 A1 * 12/2009 Schubert et al. .............. 585/654

FOREIGN PATENT DOCUMENTS

WO    WO 2007/113085 A2    10/2007

OTHER PUBLICATIONS

Wagener et al., "Opportunities and Challenges at the Interface between Petrochemistry and Refinery: Separation of Propane/Propene Mixtures by Selective Adsorption on Metal Organic Frameworks", DGMK Tagungsbericht, vol. 2007-2, 2007, XP008104016, pp. 213-220.
A. Sungpet, et al., "Silver doped Nafion-poly(pyrrole) membranes for facilitated permeation of liquid-phase olefins", J. Membr. Sci., 189 (2001) 271-279.
Activated Diffusion, 104-110.
Adriano Zecchina et al., "Structure and nuclearity of active sites in Fe-zeolites: comparison with iron sites in enzymes and homogeneous catalysts", Phys. Chem. Chem. Phys., 2007 9, 3483-3499.
Adsorption of Nitrogen Oxide and Nitrogen Dioxide, 123-130.
Alexandre, Vimont, et al., "Creation of Controlled Brønsted Acidity on a Zeotypic Mesoporous Chromium(III) Carboxylate by Grafting Water and Alcohol Molecules", Journal of Physical Chemistry C, 111 (2007), 383-388.
Alexandre Vimont, et al., "Investigation of Acid Sites in a Zeotypic Giant Pores Chromium(III) Carboxylate", J. Am. Chem. Soc., 2006, 128, 3218-3227.
Bharat L. Newalkar, et al., "Potential Adsorbent for Light Hydrocarbon Separation: Role of SBA-15 Framework Porosity", Chem. Mater. 2003, 15, 1474-1479.
C. M. Shu, et al., "Experimental and Computational studies on propane-propylene separation by adsorption and variable-temperature stepwise desorption", Separations Technology, 1990, vol. 1, 18-28.
Caroline Mellot-Draznieks, et al., "Very Large Swelling in Hybrid Frameworks: A Combined Computational and Powder Diffraction Study", J. Am. Chem. Soc. 2005, 127, 16273-16278.
Chester T. Dziobkowski, et al., "Magnetic Properties and Mossbauer Spectra of Several Iron (III)-Dicarboxylic Acid Complexes" Inorg. Chem. 1981, 20, 671-678.

(Continued)

Primary Examiner — Frank Lawrence
(74) Attorney, Agent, or Firm — Arent Fox LLP

(57) ABSTRACT

The present invention relates to reducible porous crystalline solids, constituted of a metal-organic framework (MOF), for the separation of mixtures of molecules having different unsaturation degrees and/or a different number of unsaturations with a selectivity that can be adjusted by controlling the reduction of the MOF. The MOF solids of the present invention, after reduction, have a strong affinity for molecules containing at least one unsaturation. They can be used in various separation processes, especially those relating to hydrocarbons.

16 Claims, 82 Drawing Sheets

(56) References Cited

OTHER PUBLICATIONS

Christian Serre, et al., "A Route to the Synthesis of Trivalent Transistion-Metal Porous Carboxylates with Trimeric Secondary Building Units" Angew. Chem. Int. Ed. 2004, 43, 6286-6289.

Colin S. Cundy, Microwave Techniques in the Synthesis and Modification of Zeolite Catalysts. A review, Collect. Czech. Chem. Commun. (vol. 63) (1998).

E. R. Gilliland, et al., "Reaction of Olefins with Solid Cuprous Halides", vol. 63, Aug. 1941, 2088-2090.

G De Weireld, et al., "Automated Determination of High-Temperature and High-Pressure Gas Adsorption Isotherms Using a Magnetic Suspension Balance" Meas. Sci. Technol. 10 (1999) 117-126.

Gerard Ferey, et al., "A Hybrid Solid with Giant Pores Prepared by a Combination of Targeted Chemistry, Simulation, and Powder Diffraction", Angew. Chem. Int. ed. 2004, 43, 6296-6301.

Ging-Ho Hsiue et al., "Novel methods in separation of olefin/paraffin mixgtures by functional polymeric membrances" Journal of Membrane Science, 82 (1993) 117-128.

Giuliana Magnacca, et al., "Structural and Surface Characterization of Pure and Sulfated Iron Oxides", Chem. Mater., 2003, 15, 675-687.

Harri Jarvelin, et al., "Adsorptive Separation of Propylene-Propane Mixtures", Ind. Eng. Chem. Res. 1993, 32, 2201-2207.

Ingo Pinnau, et al., "Solid Polymer Electrolyte Composite Membranes for Olefin/Paraffin Separation", Journal of Membrane Science 184 (2001) 39-48.

Jin-Sheng Yang, et al., "Swollen polymeric complex membranes for olefin/paraffin separation", Journal of Membrane Science 138 (1998) 203-211.

Joeri F. M. Denayer, et al., "Molecular Competition Effects in Liquid-Phase Adsorption of Long-Chain n-Alkane Mixtures in ZSM-5 Zeolite Pores", Angew. Chem Int. Ed. 2003, 42, 2774-2777.

Joeri F. M. Denayer, et al., "Rotational Entropy Driven Separation of Alkane/Isoalkane Mixtures in Zeolite Cases", Angew. Chem. Int. Ed. 2005, 44, 400-403.

Oliver H. LeBlanc, Jr., et al., "Facilitated Transport in Ion-Exchange Membranes", Journal of Membrane Science, 6 (1980) 339-343.

P. Glanz, et al., "Adsorption of gas mixtures of propene and propane on graphitized carbon black I. Experimental method and results", Adsorption Science & Technology (1984) 1, 41-50.

Pascal D. C. Dietzel et al., "Hydrogen adsorption in a nickel based coordination polymer with open metal sites in the cylindrical cavities of the desolvated framework", Chem. Commun., 2006, 959-961.

Pascal D. C. Dietzel, et al., "Structural Changes and Coordinatively Unsaturated Metal Atoms on Dehydration of Honeycomb Analogous Microporous Metal-Organic Frameworks", P.Chem. Eur. J., 2008, 14, 2389-2397.

Philip L. Llewellyn, et al., "Gas Adsorption Microcalorimetry and Modelling to Characterise Zeolites and Related Materials", C. R. Chimie 8 (2005) 283-302.

R. Bruce Eldridge, "Olefin/Paraffin Separation Technology: A Review", Ind. Eng. Chem. Res. 1993, 32, 2208-2212.

Sung Hwa Jhung, et al., "Microwave Synthesis of a Nanoporous Hybrid Material, Chromium Trimesate", Bull. Korean Chem. Soc. 2005, vol. 26, No. 6, 880-881.

Suzy Surblé, et al., "Synthesis of MIL-102, a Chromium Carboxylate Metal-Organic Framework, with Gas Sorption Analysis", J. Am. Chem. Soc. 2006 128, 14889-14896.

Thomas Rostrup-Nielsen, "Manufacture of hydrogen", Catalysis Today 106 (2005) 293-296.

Yunling Liu, et al, "Assembly of Metal-Organic Frameworks (MOFs) Based on Indium-Trimer Building Blocks: A Porous MOF with soc Topology and High Hydrogen Storage", Angew. Chem. Int. Ed. 2007, 46, 3278-3283.

* cited by examiner

Solid symbol: propane
Open symbol: propylene

Solid symbol: propane
Open symbol: propylene

Solid symbol: propane
Open symbol: propylene

Figure 43B

Crystallographic data for the iron(III) carboxylate MIL-126:

Formula sum: $Fe_3O[H_2O]_2.[O_2C-C_{12}H_8-CO_2]_3.X.nH_2O$ (X=OH, Cl...)
Formula weight: 952.16 g/mol (for X=OH)
Crystal system: tetragonal
Space group: P 43 21 2 (n°96)
Unit cell dimensions: a=21.800(3) Å c=35.407(7) Å
Cell volume: 16826.82(467) Å$^3$
Calculated density: 0.751659 g/cm$^3$

| Atom | wyckoff site | x/a | y/b | z/c |
|---|---|---|---|---|
| Fe1 | 8b | 0.28094(7) | 0.00027(7) | 0.09865(4) |
| Fe2 | 8b | 0.34284(7) | -0.00269(7) | 0.01345(4) |
| Fe3 | 8b | 0.19258(7) | 0.00729(7) | 0.02312(4) |
| O1 | 8b | 0.35274(4) | 0.0609(4) | 0.0978(2) |
| O2 | 8b | 0.3852(4) | 0.0691(3) | 0.0375(2) |
| C1 | 8b | 0.3840(6) | 0.0847(6) | 0.0721(4) |
| C2 | 8b | 0.4277(6) | 0.1345(6) | 0.0815(4) |
| C3 | 8b | 0.4478(6) | 0.1417(6) | 0.1198(4) |
| H3 | 8b | 0.43470 | 0.11330 | 0.13850 |

Figure 43C

| Atom | wyckoff site | x/a | y/b | z/c |
|---|---|---|---|---|
| C4 | 8b | 0.4857(6) | 0.1890(6) | 0.1296(4) |
| H4 | 8b | 0.49670 | 0.19460 | 0.15540 |
| C5 | 8b | 0.5090(6) | 0.2303(6) | 0.1017(4) |
| C6 | 8b | 0.4912(6) | 0.2197(6) | 0.0654(4) |
| H6 | 8b | 0.50620 | 0.24610 | 0.04610 |
| C7 | 8b | 0.4519(6) | 0.1717(6) | 0.0553(4) |
| H7 | 8b | 0.44210 | 0.16540 | 0.02950 |
| C8 | 8b | 0.5481(6) | 0.2828(6) | 0.1131(3) |
| C9 | 8b | 0.5335(6) | 0.3149(6) | 0.1454(3) |
| H9 | 8b | 0.49630 | 0.30690 | 0.15850 |
| C10 | 8b | 0.5739(6) | 0.3590(6) | 0.1583(3) |
| H10 | 8b | 0.56560 | 0.37880 | 0.18170 |
| C11 | 8b | 0.6263(6) | 0.3753(6) | 0.1383(3) |
| C12 | 8b | 0.6374(6) | 0.3455(6) | 0.1066(4) |
| H12 | 8b | 0.67290 | 0.35600 | 0.09250 |
| C13 | 8b | 0.5992(6) | 0.2996(6) | 0.0931(4) |
| H13 | 8b | 0.60850 | 0.27970 | 0.06990 |
| C14 | 8b | 0.6703(6) | 0.4180(5) | 0.1558(3) |
| O3 | 8b | 0.1559(4) | 0.0589(3) | 0.0629(2) |
| O4 | 8b | 0.2212(4) | 0.0692(3) | 0.1109(2) |
| O5 | 8b | 0.1621(4) | -0.0678(4) | 0.0501(2) |
| O6 | 8b | 0.2109(4) | -0.0624(4) | 0.1056(2) |
| C15 | 8b | 0.1715(6) | -0.0836(6) | 0.0834(4) |
| C16 | 8b | 0.1317(8) | -0.1355(7) | 0.0986(4) |
| C17 | 8b | 0.0850(8) | -0.1604(8) | 0.0766(5) |
| H17 | 8b | 0.07610 | -0.14220 | 0.05290 |
| C18 | 8b | 0.0522(8) | -0.2087(8) | 0.0875(5) |

Figure 43D

| Atom | wyckoff site | x/a | y/b | z/c |
|---|---|---|---|---|
| H18 | 8b | 0.02860 | -0.22990 | 0.06910 |
| C19 | 8b | 0.0509(9) | -0.2288(9) | 0.1235(5) |
| C20 | 8b | 0.0985(8) | -0.2072(8) | 0.1442(5) |
| H20 | 8b | 0.10650 | -0.22590 | 0.16790 |
| C21 | 8b | 0.1385(8) | -0.1565(8) | 0.1322(5) |
| H21 | 8b | 0.16840 | -0.13990 | 0.14880 |
| C22 | 8b | 0.0102(9) | -0.2763(9) | 0.1367(5) |
| C23 | 8b | -0.0377(9) | -0.2917(9) | 0.1159(5) |
| H23 | 8b | -0.04380 | -0.27100 | 0.09270 |
| C24 | 8b | 0.4182(8) | -0.1612(7) | 0.1232(4) |
| H24 | 8b | 0.38470 | -0.15040 | 0.13900 |
| C25 | 8b | 0.4278(7) | -0.1338(7) | 0.0894(4) |
| C26 | 8b | 0.4823(7) | -0.1443(7) | 0.0714(5) |
| H26 | 8b | 0.49320 | -0.12010 | 0.05010 |
| C27 | 8b | 0.0213(9) | -0.3108(9) | 0.1665(5) |
| H27 | 8b | 0.05820 | -0.30410 | 0.18020 |
| C28 | 8b | 0.3821(7) | -0.0851(6) | 0.0769(4) |
| O7 | 8b | 0.3921(4) | -0.0633(4) | 0.0451(2) |
| O8 | 8b | 0.3419(4) | -0.0702(4) | 0.0984(2) |
| O9 | 8b | 0.2096(3) | -0.0491(3) | -0.02044(19) |
| O10 | 8b | 0.3096(4) | -0.0729(3) | -0.0166(2) |
| C29 | 8b | 0.2577(6) | -0.0790(5) | -0.0302(3) |
| C30 | 8b | 0.2485(6) | -0.1269(5) | -0.0600(3) |
| C31 | 8b | 0.3001(6) | -0.1563(5) | -0.0741(4) |
| H31 | 8b | 0.33920 | -0.14890 | -0.06320 |
| C32 | 8b | 0.2946(6) | -0.1960(6) | -0.1038(4) |
| H32 | 8b | 0.33060 | -0.21450 | -0.11370 |

Figure 43E

| Atom | wyckoff site | x/a | y/b | z/c |
|---|---|---|---|---|
| C33 | 8b | 0.2410(6) | -0.2098(6) | -0.1195(4) |
| C34 | 8b | 0.1877(6) | -0.1799(6) | -0.1049(4) |
| H34 | 8b | 0.14850 | -0.18940 | -0.11510 |
| C35 | 8b | 0.1924(6) | -0.1376(6) | -0.0764(3) |
| H35 | 8b | 0.15720 | -0.11580 | -0.06810 |
| C36 | 8b | 0.2351(6) | -0.2546(6) | -0.1491(4) |
| C37 | 8b | 0.2187(5) | 0.2402(5) | -0.0749(3) |
| H37 | 8b | 0.18700 | 0.27010 | -0.07390 |
| C38 | 8b | 0.2186(5) | 0.1896(5) | -0.0496(3) |
| H38 | 8b | 0.18530 | 0.18450 | -0.03260 |
| C39 | 8b | 0.2670(5) | 0.1471(5) | -0.0494(3) |
| C40 | 8b | 0.3126(6) | 0.1552(6) | -0.0739(3) |
| H40 | 8b | 0.34540 | 0.12660 | -0.07410 |
| C41 | 8b | 0.3140(6) | 0.2034(6) | -0.0989(4) |
| H41 | 8b | 0.34850 | 0.20850 | -0.11500 |
| C42 | 8b | 0.2640(5) | 0.0926(5) | -0.0247(3) |
| O11 | 8b | 0.3105(3) | 0.0578(3) | -0.0251(2) |
| O12 | 8b | 0.2154(3) | 0.0840(3) | -0.00599(19) |
| O13 | 8b | 0.2734(3) | 0.0019(3) | 0.04485(18) |
| O14 | 8b | 0.4190(4) | -0.0087(4) | -0.0234(2) |
| O15 | 8b | 0.1026(4) | 0.0168(4) | -0.0007(2) |
| O16 | 8b | 0.2929(4) | -0.0005(4) | 0.1559(2) |

Figure 43F

Interatomic distances (in Å)

| | | | |
|---|---|---|---|
| Fe1 | O13 | 1x | 1.9123 |
| | O8 | 1x | 2.0313 |
| | O4 | 1x | 2.0352 |
| | O16 | 1x | 2.0438 |
| | O1 | 1x | 2.0482 |
| | O6 | 1x | 2.0636 |
| Fe2 | O13 | 1x | 1.8809 |
| | O10 | 1x | 2.0000 |
| | O2 | 1x | 2.0068 |
| | O11 | 1x | 2.0246 |
| | O7 | 1x | 2.0383 |
| | O14 | 1x | 2.1157 |
| Fe3 | O13 | 1x | 1.9261 |
| | O3 | 1x | 1.9721 |
| | O9 | 1x | 2.0069 |
| | O5 | 1x | 2.0084 |
| | O12 | 1x | 2.0264 |
| | O15 | 1x | 2.1452 |
| O1 | C1 | 1x | 1.2501 |
| O2 | C1 | 1x | 1.2717 |
| C1 | C2 | 1x | 1.4822 |
| C2 | C7 | 1x | 1.3403 |
| C3 | C3 | 1x | 1.4337 |
| C4 | C4 | 1x | 1.3661 |
| C5 | C5 | 1x | 1.4299 |
| C6 | C6 | 1x | 1.3623 |
| | C8 | 1x | 1.4830 |
| | C7 | 1x | 1.3989 |

Figure 43G

Interatomic distances (in Å)

| | | | |
|---|---|---|---|
| C8 | C13 | 1x | 1.3699 |
| C9 | C9 | 1x | 1.3780 |
| C10 | C10 | 1x | 1.3815 |
| C11 | C11 | 1x | 1.3902 |
| | C12 | 1x | 1.3192 |
| C12 | C14 | 1x | 1.4733 |
| C14 | C13 | 1x | 1.3868 |
| | O3 | 1x | 1.2571 |
| | O4 | 1x | 1.2879 |
| O5 | C15 | 1x | 1.2453 |
| O6 | C15 | 1x | 1.2527 |
| C15 | C16 | 1x | 1.5240 |
| C16 | C21 | 1x | 1.2833 |
| | C17 | 1x | 1.3921 |
| C17 | C18 | 1x | 1.3300 |
| C18 | C19 | 1x | 1.3482 |
| C19 | C20 | 1x | 1.3549 |
| | C22 | 1x | 1.4415 |
| C20 | C21 | 1x | 1.4705 |
| C22 | C27 | 1x | 1.3181 |
| | C23 | 1x | 1.3212 |
| C23 | C24 | 1x | 1.4586 |
| C24 | C25 | 1x | 1.3538 |
| C25 | C26 | 1x | 1.3675 |
| | C28 | 1x | 1.5217 |
| C26 | C27 | 1x | 1.3655 |
| C28 | O8 | 1x | 1.2054 |

Figure 43H

| Interatomic distances (in Å) | | |
|---|---|---|
| O9 | O7 | 1x | 1.2414 |
| O10 | C29 | 1x | 1.2821 |
| C29 | C29 | 1x | 1.2368 |
| C30 | C30 | 1x | 1.4980 |
| | C35 | 1x | 1.3738 |
| C31 | C31 | 1x | 1.3876 |
| C32 | C32 | 1x | 1.3672 |
| C33 | C33 | 1x | 1.3285 |
| | C34 | 1x | 1.4291 |
| C34 | C36 | 1x | 1.4383 |
| C36 | C35 | 1x | 1.3708 |
| | C37 | 1x | 1.3692 |
| C37 | C41 | 1x | 1.4103 |
| C38 | C38 | 1x | 1.4210 |
| C39 | C39 | 1x | 1.4042 |
| | C40 | 1x | 1.3311 |
| C40 | C42 | 1x | 1.4767 |
| C42 | C41 | 1x | 1.3742 |
| | O12 | 1x | 1.2635 |
| | O11 | 1x | 1.2662 |

REDUCIBLE POROUS CRYSTALLINE HYBRID SOLID FOR THE SEPARATION OF MIXTURES OF MOLECULES HAVING DIFFERENT DEGREES AND/OR A DIFFERENT NUMBER OF UNSATURATIONS

CROSS-REFERENCE TO RELATED APPLICATION

This application is a National Stage entry of International Application No. PCT/FR2009/000699, filed Jun. 11, 2009, which claims priority to French Patent Application No. 08/03245 filed Jun. 11, 2008, the disclosure of the prior application is incorporated in its entirety by reference.

DESCRIPTION

1. Technical Field

The present invention relates to the use of porous crystalline solids constituted of a metal-organic framework (MOF) for the separation of mixtures of molecules having different unsaturation degrees and/or a different number of unsaturations.

The MOF solids of the present invention can be used for the separation of olefin/paraffin mixtures. They can for example be used for the separation of propane/propene mixtures. They can also be used for the separation of mixtures of acetylene and carbon dioxide.

The references in square brackets [X] refer to the list of references at the end of the examples.

2. State of the Art

Metal-organic frameworks (MOF) are coordination polymers of hybrid inorganic-organic framework containing metal ions and organic ligands coordinated to the metal ions. These materials are organized into one-, two- or three-dimensional frameworks where the metal clusters are bound together by spacer ligands in a periodic manner. These materials have a crystalline structure, are most often porous and are used in many industrial applications such as the storage of gas, the adsorption of liquids, the separation of liquids or gases, catalysis, etc.

For example the US patent application 2003-0078311 [ref. 1] may be cited, which describes a reaction process making use of a catalytic system comprising an MOF material based on zinc. In the U.S. Pat. No. 6,929,679 [ref. 2] this same material is also used for the storage of gas.

In addition, MOF materials based on frameworks of the same topology are described as "isoreticular". These spatially organized frameworks made it possible to obtain a more homogenous porosity. Thus, the U.S. Pat. No. 6,930,193 [ref. 3] describes several IRMOF (Isoreticular Metal-Organic Framework) materials based on zinc used for the storage of gas.

Moreover, the separation of mixtures of compounds in the gaseous or liquid phase is a major industrial problem concerning in particular the chemical, petrochemical and/or pharmaceutical industrial sectors. For example, separating olefins from paraffins is one of the most important problems in the field of separation. The recovery of olefins is effected from mixtures of olefins and paraffins obtained from liquefaction products derived from gaseous residues from the cracking of petroleum derivatives. World demand is growing increasingly and there is growing interest in the development of novel separation methods of low energy cost. Consider for example propylene which is a fundamental precursor for the synthesis of many polymers such as polypropylene. Its production comes up against the difficulty of separating the latter from propane at an economically acceptable cost.

The current technologies have many disadvantages. For example, these use cryogenic distillation or the high pressure separation of $C_2H_4/C_2H_6$ and/or $C_3H_6/C_3H_8$ mixtures [ref. 36]. However, the differences in volatility between the olefins and the paraffins are slight, necessitating multiple plate (>100) high reflux systems, which is thus very costly.

Recently, while many alternatives to cryogenic separation have been described in the past (membranes, adsorption technologies . . . ) [ref. 4], there has for some time been a research effort on the development of novel adsorbents for the purification of olefins.

While studies using carbon [ref. 5] or silica gels [ref. 6] have been previously reported, an alternative is based on mesoporous silicas or polymers into which cations of the $Ag^+$ or $Cu^{2+}$ type have been introduced by impregnation [ref. 7]. The ions are if necessary reduced by heat treatment under vacuum, which favors the interaction of these materials with olefins [ref. 8] in accordance with the Dewar-Chatt-Duncanson model [ref. 9]. Nonetheless, these interactions are not as strong as those encountered in coordination chemistry and thus it is quite easy to desorb the alkene by heating or reducing the pressure in the system. In the present case, the alkene/alkane selectivities of this type of adsorbent are typically between 2 and 8 for a mesoporous silica loaded with silver or copper ions [Ref 7]. Their adsorption capacities are comparable to those of the zeolites and are relatively low: close to 1 $mmol \cdot g^{-1}$ at 1 bar and ambient temperature. Moreover, the diffusivity of the molecules, particularly molecules of large size, is relatively limited for this type of material owing to their pore sizes. On the other hand, the selectivity of these materials can with difficulty be modulated/adjusted depending on the mixture to be separated, for example for a propene/propane mixture.

The zeolites have also been used as adsorbents for the separation of olefin/paraffin mixtures. These are mainly cationic zeolites of the 5A or 13X type which have for example an ethylene/ethane selectivity between 12 and 15 (at 323 K) [ref. 10]. The problem with these adsorbents comes from the fact that the desired product is the olefin which is very strongly adsorbed in the material. It is therefore complicated to recover the olefin, which constitutes a brake on the development of separation processes based on these materials.

On the other hand, the use of zeolites which have a restricted pore size leads to problems of intracrystalline diffusivity in the pores and hence high mass transfer resistance involving very poor regenerability. To remedy these problems a high desorption temperature, between 100 and 200° C., is necessary with risks of polymerizing the olefin in the pores of the adsorbent and hence of decreasing the selectivity and the adsorption capacity [ref. 11]. In practice, these acidic zeolites are not used at the industrial level for such applications.

While the acidic zeolites have many disadvantages for the separation of olefins/paraffins, it appears that a revival of interest currently relates to the neutral "silicic" zeolites or aluminophosphates of the 8-ring type (Chabazite) [ref. 12]. In fact, in spite of a negligible thermodynamic selectivity in the absence of cations in the pores, these latter nonetheless exhibit good dynamic selectivities with alkene/alkane diffusion coefficient ratios of the order of $10^4$, suggesting that these latter could be used for the purification of olefins. The basis of the separation is geometrical with a pore size (range: 3.7-4.2*4.1-4.5 Å) and tortuosity (elliptical) more favorable to the alkenes than to the alkanes. For a purification process of the PSA (Pressure Swing Adsorption) type, it is essential to obtain the olefin with a very high purity defined by $s=(KC_3H_6/KC_3H_8)/SR(DC_3H_6/DC_3H_8)$ with K: equilibrium constant and D: diffusion coefficient. The adsorbents of the CHA or DD3R type have performances of 99% in terms of purity, confirming the possibility of using them for this type of separation. Nonetheless there are restrictions: in order not to lose the selectivity, positioning at less than 45% of the equilibrium capacity is necessary (Henry's law) and the frequency of the cycles must correspond to that of the species which diffuses most rapidly (propylene), that is to say here between 5 and 2000 seconds for these two adsorbents.

On the same sort of principle, the purely silicic zeolite ITQ-12 has the distinctive feature of having a propane/propylene selectivity which is a function of the temperature [ref. 13]. While at 30° C. the alkene is adsorbed 100 times faster than propane, at 80° C. a deformation of the pores leads to exclusive adsorption of the propylene and preliminary tests of the PSA type indicate production of propylene at a purity of 99.5%. However, the high cost of this adsorbent (i.e. use of HF and the structuring agent 1,3,4-trimethylimidazolium) constitutes an obstacle to its use in industrial processes.

Finally, certain MOFs or Metal Organic Frameworks have been studied in the context of the separation of gases. For example, the study containing the copper trimesate HKUST-1 (HKUST for Hong Kong University) may be cited [ref. 14]. This porous copper(II) carboxylate has a system of cages of diameter 9 Å, a specific surface area (for the solid produced during that study) of 1800 m²·g⁻¹ and dimers of copper. These latter lose their coordinated molecules of water by dehydration, giving way to unsaturated copper (II) metal centers. These possess Lewis acidity enabling the coordination of unsaturated molecules of the NO type [ref. 15]. A preliminary study of the interaction of propane and propylene was performed on this solid. The calculated heats of adsorption of these two molecules are rather close with HKUST-1, −30 KJ/mol (propane) and −33 KJ/mol (propylene), leading one to expect a low thermodynamic separation. In this respect, a breakthrough test on a column loaded with previously activated solid displays a difference in retention time between propane, retained for 40 minutes at 20° C., and propylene which only starts to emerge from the column after 60 minutes. However, the selectivity, equal to 2, calculated from these breakthrough curves is not sufficient to envisage the application of this material in a process for separation of olefin/paraffin mixtures on the industrial scale. Further, the selectivity of these materials can with difficulty be modulated/adjusted depending on the mixture to be separated, for example for a propene/propane mixture.

U.S. Pat. No. 6,491,740 [ref. 16] which describes the use of an MOF material based on copper II to eliminate contaminants (CH4, H2, N2, O2) from a mixture of hydrocarbons or to remove hydrocarbons from a gas stream can also be cited. The solid described in the examples is HKUST-1; the same remarks as those made in the previous paragraph concerning the limitations and deficiencies of this material thus apply. It can also be noted that the MOFs based on copper are relatively costly. In addition, their stability in presence of water in aqueous solution is not very good [ref 15].

At present there is no adsorbent satisfying the list of requirements for industrial paraffin/olefin separation simultaneously having suitable selectivity, cost and diffusion properties, and absence of polymerization of the propylene. Hence alkane/alkene separation is currently effected by a cryogenic route and has very high energy costs. Finding an absorbent making it possible to replace this expensive method while satisfying the required criteria (selectivity, diffusivity, regeneration . . . ) would constitute a major advance in this field.

Among the disadvantages of the processes already known, the following can be cited as examples:
prohibitive implementation costs.
lack of selectivity of the system/separation material.
insufficient diffusivity of the species to be separated in the separation material
problems of lixiviation with the existing separation materials.

There is therefore a real need to develop systems making it possible to separate olefin/paraffin mixtures efficiently, as well as other mixtures of molecules having different unsaturation degrees and/or a different number of unsaturations.

DISCLOSURE OF THE INVENTION

The purpose of the present invention is precisely to respond to these needs and disadvantages of the prior art by proposing the use of a porous crystalline MOF solid comprising reduced metal sites to separate a mixture of molecules having different unsaturation degrees and/or a different number of unsaturations, said solid comprising a three-dimensional structure of moieties corresponding to the following formula (I):

$$M_m O_k X_l L_p \qquad (I)$$

in which:
each occurrence of M independently represents an ion of a transition metal $M^{z+}$ or the reduced form thereof $^{(z-1)+}$ selected from the group comprising Fe, Mn, Co, Ni and V, z is 3 or 4, provided that the ratio $y=M^{(z-1)+}/M^{z+}$ lies between $0<y\leq x$, where x is the fraction of accessible ions $M^{z+}$ of the MOF solid,
m is 1 to 12,
k is 0 to 4,
l is 0 to 18,
p is 1 to 6,
X is an anion selected from the group comprising OH⁻, Cl⁻, F⁻, I⁻, Br⁻, $SO_4^{2-}$, $NO_3^-$, $ClO_4^-$, $PF_6^-$, $BF_4^-$, $R-(COO)_n^-$ where R is as defined below, $R^1-(COO)_n^-$, $R^1-(SO_3)_n^-$ or $R^1-(PO_3)_n^-$, where $R^1$ is a hydrogen atom, a linear or branched, optionally substituted $C_1$ to $C_{12}$ alkyl, an optionally substituted $O_6$ to $C_{10}$ aryl, and where n represents an integer from 1 to 4,
L is a spacer ligand comprising a radical R containing q carboxylate groups

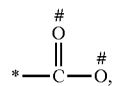

where
q is 1, 2, 3, 4, 5 or 6,
* designates the point of attachment of the carboxylate to the radical R,
designates the possible points of attachment of the carboxylate to the metal ion,
R represents:
(i) a $C_{1-12}$ alkyl, $C_{2-12}$ alkene or $C_{2-12}$ alkyne radical,
(ii) a mono- or polycyclic, fused or non-fused aryl radical, comprising 6 to 50 carbon atoms,
(iii) a mono- or polycyclic, fused or non-fused heteroaryl, comprising 1 to 50 carbon atoms,
(iv) an organic radical containing a metallic element selected from the group comprising ferrocene, porphyrin and phthalocyanine, the radical R being optionally substituted by one or more groups $R^2$ independently selected from the group comprising $C_{1-10}$ alkyl, $C_{2-10}$ alkene, $C_{2-10}$ alkyne, $C_{3-10}$ cycloalkyl, $C_{1-10}$ heteroalkyl, $C_{1-10}$ haloalkyl, $C_{6-10}$ aryl, $C_{3-20}$ heterocycle, $C_{1-10}$ alkyl $C_{6-10}$ aryl, $C_{1-10}$ alkyl $C_{3-10}$ heteroaryl, F, Cl, Br, I, —$NO_2$, —CN, —$CF_3$, —$CH_2CF_3$, —OH, —$CH_2OH$, —$CH_2CH_2OH$, —$NH_2$, —$CH_2NH_2$, —NHCHO, —COOH, —$CONH_2$, —$SO_3H$, —$CH_2SO_2CH_3$, —$PO_3H_2$, or a -$GR^{G1}$ group in which G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, or —C(=S)—, and where independently of other occurrences of $R^{G2}$ each occurrence of $R^{G2}$ is a hydrogen atom, or a linear, branched or cyclic, optionally substituted $C_{1-12}$ alkyl, $C_{1-12}$ heteroalkyl, $C_{2-10}$ alkene or $C_{2-10}$ alkyne group, or a $O_{6-10}$ aryl, $C_{3-10}$ heteroaryl, $C_{5-10}$ heterocycle, $C_{1-10}$ alkyl $C_{6-10}$ aryl or $C_{1-10}$ alkyl $C_{3-10}$ heteroaryl group in which the aryl, heteroaryl or heterocyclic radical is optionally substituted, or else, when G represents —$NR^{G2}$—, $R^{G1}$ and $R^{G2}$ together with the nitrogen atom to which they are bound form an optionally substituted heterocycle or heteroaryl.

In certain embodiments, M can represent V and z can be 4 ($V^{4+}/V^{3+}$ redox couple).

In certain other embodiments, M can represent Ni and z can be 3 ($Ni^{3+}/Ni^{2+}$ redox couple).

Advantageously, each occurrence of M independently represents an ion of a transition metal $M^{z+}$ or the reduced form thereof $^{(z-1)+}$ selected from the group comprising Fe, Mn, Co, Ni (z is then 3) and V (z is then 4).

As used herein, the fraction of accessible $M^{z+}$ ions of the MOF solid x, refers to the ratio between the number of accessible $M^{z+}$ ions of the MOF solid and the total number of $M^{z+}$ ions present in the MOF solid. The number of accessible $M^{z+}$ ions of the MOF solid represents the number of $M^{z+}$ ions of the MOF solid capable of being reduced to $M^{(z-1)+}$ ions. Thus, x represents the maximal fraction of $M^{(z-1)+}$ ions which an MOF solid according to the invention may contain.

In the context of the present invention, x is strictly greater than zero.

In certain embodiments x can represent any fraction lying between zero (limit 0 excluded) and ⅓ (limit ⅓ included). Advantageously, x can represent ⅓. This embodiment will relate to MOFs reduced by the phenomenon of auto-reduction (i.e. in an initial period, a temperature <150° C., or even <100° C., makes it possible to remove the molecules of water and solvent coordinated at the $M^{z+}$ sites. Above 100° C., in particular above 150° C., the $M^{z+}$ sites begin to be reduced. The reduction can be accompanied by the elimination of a negatively charged ligand (−1) to preserve the electrical neutrality of the MOF solid). For example, x can be 0.10, 0.15, 0.20, 0.25, 0.30 or ⅓, this last value corresponding to the maximum theoretical activation of the MOF material by reduction of the $M^{z+}$ sites by the phenomenon of autoreduction (i.e. the electrical neutrality of the MOF solid being preserved by the elimination of negatively charged ligands (−1)).

In certain embodiments x can be greater than ⅓. This will relate to MOFs containing at least one ligand capable of being oxidized (redox ligand), such as for example hydroquinone the oxidized form whereof is quinone. In that case, the reduction of the porous MOF solid can be accompanied by charge compensation due not only to the loss of a counter-ion of the metal (as in the previous implementation mode) but also due to the oxidation of the organic ligand. It is thus possible to increase the content of reduced $M^{(z-1)+}$ ion beyond the ratio x=⅓. The reader will be able to refer to example 31 below for a practical example. In theory, the proportion of reduction of the $M^{z+}$ ions can reach as much as 100% (i.e. x=1). For example, x can be 0.35, 0.40, 0.45, 0.50, 0.60, 0.70, 0.80, 0.90 or even 1.

In the context of the present invention, the term "substituted" designates for example the replacement of a hydrogen radical in a given structure by an $R^2$ radical as previously defined. When more than one position can be substituted, the substituents can be the same or different at each position.

In the sense of the present invention "spacer ligand" is understood to mean a ligand (including for example neutral species and ions) coordinated to at least two metals, participating in the distancing between these metals and in the formation of empty spaces or pores. The spacer ligand can contain 1 to 6 carboxylate groups, as defined above, which can be monodentate or bidentate, in other words contain one or two points of attachment to the metal. The points of attachment to the metal are represented by the symbol # in the formulae. When the structure of a group A contains two points of attachment #, this means that the coordination to the metal can take place by one, the other or both points of attachment.

In the sense of the present invention "alkyl" is understood to mean a linear, branched or cyclic, saturated or unsaturated, optionally substituted, carbon radical, comprising 1 to 12 carbon atoms, for example 1 to 10 carbon atoms, for example 1 to 8 carbon atoms, for example 1 to 6 carbon atoms.

In the sense of the present invention, "alkene" is understood to mean an alkyl radical, as previously defined, having at least one carbon-carbon double bond.

In the sense of the present invention, "alkyne" is understood to mean an alkyl radical as previously defined, having at least one carbon-carbon triple bond.

In the sense of the present invention, "aryl" is understood to mean an aromatic system containing at least one ring satisfying the Hückel aromaticity rule. Said aryl is optionally substituted and can contain from 6 to 50 carbon atoms, for example 6 to 20 carbon atoms, for example 6 to 10 carbon atoms.

In the sense of the present invention, "heteroaryl" is understood to mean a system containing at least one aromatic ring of 5 to 50 members among which at least one member of the aromatic ring is a hetero atom, in particular selected from the group comprising sulfur, oxygen, nitrogen and boron. Said heteroaryl is optionally substituted and can contain from 1 to 50 carbon atoms, preferably 1 to 20 carbon atoms, preferably 3 to 10 carbon atoms.

In the sense of the present invention, "cycloalkyl" is understood to mean a cyclic, saturated or unsaturated, optionally substituted, carbon-containing radical which can contain 3 to 20 carbon atoms, preferably 3 to 10 carbon atoms.

In the sense of the present invention, "haloalkyl" is understood to mean an alkyl radical as previously defined, said alkyl system containing at least one halogen.

In the sense of the present invention, "heteroalkyl" is understood to mean an alkyl radical as previously defined, said alkyl system containing at least one hetero atom, in particular selected from the group comprising sulfur, oxygen, nitrogen and boron.

In the sense of the present invention, "heterocycle" is understood to mean a saturated or unsaturated, optionally substituted, cyclic carbon-containing radical containing at least one hetero atom, and which can contain 2 to 20 carbon atoms, preferably 5 to 20 carbon atoms, preferably 5 to 10 carbon atoms. The hetero atom can for example be selected from the group comprising sulfur, oxygen, nitrogen and boron.

In the sense of the present invention, "alkoxy", "aryloxy", "heteroalkoxy" and "heteroaryloxy" are understood to mean respectively an alkyl, aryl, heteroalkyl and heteroaryl radical bound to an oxygen atom.

In the sense of the present invention, "alkylthio", "arylthio", "heteroalkylthio" and "heteroarylthio" are understood to mean respectively an alkyl, aryl, heteroalkyl and heteroaryl radical bound to a sulfur atom.

As used herein, "three-dimensional structure" refers to a three-dimensional succession or repetition of moieties of formula (I) as is conventionally understood in the field of MOF materials, which are also characterized as "metallo-organic polymers".

As used herein, the term "unsaturation" refers to a multiple bond (double or triple) or a free electron pair present on a hetero atom selected from O, S, N and P.

In the present, the multiple bond can link:
two carbon atoms (C=C, CC),
a carbon atom and an heteroatom (C=O, C=S, —C=N—, C≡N), or
two heteroatoms (N=N, P=O, P=S).

The term "unsaturation degree" refers to the nature of a multiple bond, namely a double bond or a triple bond, the latter having a degree of unsaturation greater (3) than a double bond (2).

The number of unsaturations is the unsaturations count of a molecule, as defined above. This is the sum N of the multiple bonds and free electron pairs present in a given molecule, as defined above.

By way of example, the unsaturations can be present in the form of a double bond C=C, a triple bond C≡C, a carboxyl group —$CO_2H$, an oxo group C=O, an aldehyde group —C(=O)H, a cyanide group —C≡N, a nitro group —$NO_2$, an ester group —$CO_2R$, C=S, —C=N—, C≡N, N=N, P=O, P=S, a phenyl group, an aryl group and/or a heteroaryl group.

Another object of the invention is a process for separating a mixture of molecules having different unsaturation degrees and/or a different number of unsaturations by preferential adsorption of the molecules with a greater degree and/or number of unsaturations on a porous crystalline MOF solid as defined above, said process containing at least one reaction step consisting (i) in mixing in a polar solvent:
at least one solution containing at least one inorganic metal precursor present in the form of metal M, a metal salt of M or a coordination complex containing a metal ion of M
at least one ligand L' comprising a radical R containing q groups *—C(=O)—$R^3$, where
M, q and R are as defined above,
* designates the point of attachment of the group to the radical R,
$R^3$ is selected from the group comprising an OH, an OY, wherein Y is an alkaline cation, a halogen, or a radical —$OR^4$, —O—C(=O)$R^4$, —$NR^4R^{4'}$, where $R^4$ and $R^{4'}$ are $C_{1-12}$ alkyl radicals, to obtain an MOF material,
(ii) in activating the MOF material obtained in (i), and
(iii) in placing the MOF material obtained in step (ii) in contact with a mixture of molecules having different unsaturation degrees and/or a different number of unsaturations.

M is an ion of a transition metal selected from the group comprising Fe, Mn, Co, Ni and V, as previously defined.

Unless otherwise stated, the various embodiments which follow relating to the MOF materials apply as much to the aforesaid use as to the aforesaid process of the invention.

The distinctive crystal structure of the MOF solids according to the invention, as well as the possibility of reducing certain metal sites (accessible metal sites) to $M^{(z-1)+}$ ions without affecting the structure of these solids, procure for these materials specific properties particularly suitable for the separation of mixtures of molecules having different unsaturation degrees and/or a different number of unsaturations.

In the MOF solids of the invention, M is selected from the group comprising Fe, Mn, Co, Ni and V. The MOF solids of the invention can also contain a mixture of these metals. M is advantageously Fe, in its oxidized form (Fe(III)) or its reduced form (Fe(II)).

As previously stated, M is a transition metal ion $M^{z+}$ in which z is 3. Thus, each occurrence of M can be independently Fe(III), Mn(III), Co(III) or V(III), or the reduced form Fe(II), Mn(II), Co(II) or V(II), respectively.

M can also represent V(IV), or its reduced form V(III). In that case, z represents 4.

M can also represent Ni(III), or the reduced form thereof, Ni(II). In that case, z represents 3.

When M is a mixture of metals, for each metal, z can have an identical or different value.

In one embodiment of the invention, the solids of the invention comprise a three-dimensional structure of moieties of formula (I) in which M can represent a single type of metal, for example Fe, in the Fe(II) and/or Fe(III) (i.e., z=3) form.

In general, the ratio $y=Fe^{2+}/Fe^{3+}$ is strictly greater than zero.

In certain embodiments the ratio $y=Fe^{2+}/Fe^{3+}$ can lie between $0<y\leq\frac{1}{3}$.

In other embodiments, y can be greater than $\frac{1}{3}$, when the porous MOF solid contains at least one redox ligand capable of being oxidized. Thus, in certain embodiments, $0<y\leq 1$ (see example 31 for an exemplary embodiment).

In another embodiment of the invention, the solids of the invention can comprise a three-dimensional structure of moieties of formula (I) in which M can represent a mixture of different metals, for example Fe and Mn, in which for each metal z is equal to 3.

In another embodiment of the invention, the solids of the invention can comprise a three-dimensional structure of moieties of formula (I) in which M can represent a mixture of different metals, for example Fe, Co, Ni or Mn, in which for each metal z is equal to 3, or V in which z represents 4.

In one particular implementation mode, $M^{z+}$ represents trivalent octahedral Fe with z equal to 3. In that implementation mode, the Fe has a coordination number of 6.

"Coordination number" is understood to mean the number of anions to which the cation M is bound.

The utility of the MOF materials according to the invention lies in the fact that the structure of the MOF material remains stable after reduction of metal ions $M^{z+}$ of the material to $M^{z+}$ ions. In fact, unexpectedly, it has been discovered that the MOF materials according to the invention (i.e. metal carboxylates, where the metal can be Fe, Mn, Co, Ni, V, or a combination of these) conserve their integral structure when all or part of the accessible $M^{z+}$ ions of the MOF material are reduced to corresponding $M^{(z-1)+}$ ions. This property is remarkable as it makes it possible to use the MOF materials of the invention for separating a mixture of molecules having different unsaturation degrees and/or a different number of unsaturations. In addition, it makes it possible to modulate the selectivity of the MOF material in question in the process of separation.

In fact, the unsaturated metal centers $M^{z+}$ and $M^{(z-1)+}$ have an electron acceptor nature (Lewis acid) and can form π complexes with molecules having an electron donor nature (Lewis base), such as molecules containing one or more unsaturations in the sense of the present invention. In the case where the molecule containing an unsaturation is an alkene or an alkyne, the stabilization of the complexes thus formed can be rationalized in accordance with the Dewar-Chatt-Duncanson model [ref. 9], considering on the one hand the electronic structure of the carbon-carbon double or triple bond of the olefin and on the other the vacant orbitals of the adsorption site: the bond between the alkene or the alkyne involves (i) a delocalization of the electrons of the π bonding orbitals of the unsaturated hydrocarbon towards the vacant orbitals of the adsorption site (donor-acceptor interaction via σ bond) (ii) a delocalization of the electrons of the partially filled d orbitals of the adsorption site towards the π* anti-bonding orbitals of the unsaturated hydrocarbon (π bond). The reduced metal ion $M^{(z-1)+}$ has an additional d electron compared to $M^{z+}$, which reinforces the π bond to the hydrocarbon and thus increases the stability of the complex formed. Thus, the MOF material of formula (I) simultaneously containing $M^{z+}$ metal ions and the reduced form thereof$^{(z-1)+}$ (the ratio $y=M^{(z-1)+}/M^{z+}$ is strictly greater than zero) will be able to interact more strongly with such molecules.

The above reasoning can be maintained identically for molecules containing one or more free electron pairs. In the same way, the MOF material of formula (I) simultaneously containing metal ions $M^{z+}$ and the reduced form thereof$^{(z-1)+}$ (the ratio $y=M^{(z-1)+}/M^{z+}$ is strictly greater than zero) will be able to interact more strongly with such molecules.

The inventors have demonstrated this property of the MOF solids of the invention experimentally, as described in the "Examples" section below.

In one particular implementation mode, the reduction of the metal ions $M^{z+}$ of the MOF material can be effected by activating the material at a temperature sufficiently high to result in the reduction of $M^{z+}$ sites to $M^{(z-1)+}$ ions by the autoreduction phenomenon. See for example Battiston at al. [ref. 41] and Magnacca at al. [ref. 42]. In an initial period, a temperature <150° C., or even <100° C., makes it possible to remove the molecules of water and solvent coordinated onto the $M^{z+}$ sites. Above 100° C., in particular above 150° C., the $M^{z+}$ sites start to be reduced. The reduction can be accompanied by the elimination of a negatively charged ligand (−1) to preserve the electrical neutrality of the MOF solid. The reduction can also take place by means of pumping under vacuum or a reducing agent, as specified below.

In another implementation mode, the reduction of the metal ions $M^{z+}$ of the MOF material can be preceded by treatment of the material with a source of $F^-$ ions. For example, the source of $F^-$ ions can be KF, CsF, LiF, $MgF_2$, $CaF_2$, or an amine fluoride salt such as $NH_4F$. Advantageously, this can be $NH_4F$, for example in aqueous solution.

Without wishing to be bound in any way to a particular theory, it seems that it can be proposed that this treatment makes it possible to exchange the nitrates present in the pores of the material for $F^-$ ions. This type of anion exchange has been observed in other materials (Philip L. Llewellyn, Sandrine Bourrelly, Christian Serre, Alexandre Vimont, Marco Daturi, Lomig Hamon, Guy De Weireld, Jong-San Chang, Do-Young Hong, Young Kyu Hwang, Sung Hwa Jhung, Gérard Férey "High Uptakes of $CO_2$ and $CH_4$ in Mesoporous Metal Organic Frameworks MIL-100 and MIL-101", Langmuir, 2008, 24, 7245-7250, [ref 57]).

Thus, the prior treatment with a source of $F^-$ ions makes it possible to reduce the metal sites $M^{z+}$ at lower temperature (the $F^-$ ions being smaller and lighter, and consequently more labile), and to obtain a reduced material of greater specific surface area.

In one particular implementation mode, the content of reduced ions $M^{(z-1)+}$ in the MOF material of formula (I) can be controlled/adjusted in order to modulate the selectivity of the MOF solid towards species to be separated. The content of reduced ions $M^{(z-1)+}$ can be modulated by exposing the MOF solid to a fairly high temperature and/or for a fairly long activation time. In this context, "activation time" is understood to mean the time during which the reduction of the accessible metal sites $M^{z+}$ is effected. In general, under the same conditions, the higher the temperature, the greater the content of reduced ions $M^{(z-1)+}$ in the MOF material. In the same way, the longer the activation time, the higher the content of reduced ions $M^{(z-1)+}$ in the MOF material. As discussed in the above paragraph, the thermal activation can be preceded by treatment with a source of $F^-$ ions, such as KF, CsF, LiF, $MgF_2$, $CaF_2$, or an amine fluoride salt such as $NH_4F$. This has the effect of making it possible to reduce the activation temperature and/or time.

The methods for preparation of MOF materials are well known to those skilled in the art, and will not be enlarged on in the context of the present application.

"Unsaturated metal site $M^{z+}$" is understood to mean $M^{z+}$ ions, the coordination number whereof is less than the maximum number of ligands to which the metal atom $M^{z+}$ can be bound by a σ bond. For example, when the MOF solid of formula (I) is based on a trivalent octahedral $Fe^{3+}$ ion, the maximum coordination number of the $Fe^{3+}$ ions is 6. Thus, an unsaturated metal site in an MOF of formula (I) where M is Fe and z is 3 can be an $Fe^{3+}$ ion of coordination 5. For example, in such a solid where the metal ions $Fe^{3+}$ of coordinance 6 can be coordinated to molecules of water (coordinance 6), unsaturated $Fe^{3+}$ metal sites can be obtained by heating the MOF material under vacuum to eliminate the molecules of water and/or solvent from the accessible $Fe^{3+}$ sites. The same reasoning can be maintained for the metal ions $Mn^{3+}$, $V^{3+}$ and $Co^{3+}$: neutral ligands can be eliminated from the accessible $Mn^{3+}$, $V^{3+}$ and/or $Co^{3+}$ sites by heating at a temperature sufficient to generate unsaturated $Mn^{3+}$, $V^{3+}$ and/or $Co^{3+}$ sites. The same reasoning can be maintained for the redox couples $V^{4+}/V^{3+}$ and $Ni^{3+}/Ni^{2+}$.

After heating at a higher temperature, unsaturated $Fe^{2+}$, $Mn^{2+}$, $V^{2+}$ and/or $Co^{2+}$ sites can be obtained by the autoreduction phenomenon mentioned above. Similarly, unsaturated $V^{3+}$ sites can be obtained by auto-reduction of $V^{4+}$ ions. In the same way, unsaturated $Ni^{2+}$ sites can be obtained by autoreduction of $Ni^{3+}$ ions.

The metal ions can be isolated or grouped into metal "clusters". The MOF solids according to the invention can for example be built up of chains of octahedra or of octahedron trimers.

In the sense of the present invention, "metal cluster" is understood to mean a group of atoms containing at least two metal ions linked by iono-covalent bonds, either directly by anions, for example O, OH, Cl, etc., or by the organic ligand.

Further, the MOF solids according to the invention can be present in different forms or "phases" in view of the diverse possibilities for organization and connections of the ligands to the metal ion or to the metal group.

In the sense of the present invention, "phase" is understood to mean a hybrid composition containing at least one metal and at least one organic ligand possessing a defined crystal structure.

The spatial crystalline organization of the solids of the present invention is at the heart of the special characteristics and properties of these materials. In particular, it governs the size of the pores, which has an influence on the specific surface area of the materials and on the adsorption characteristics. It also governs the density of the materials, this being relatively low, the proportion of metal in these materials, the stability of the materials, the rigidity of the structures, etc.

Moreover, the size of the pores can be adjusted by the selection of appropriate ligands L.

In one particular implementation mode, the ligand L of the moiety of formula (I) of the MOF solids of the present invention can be a di-, tri-, tetra- or hexacarboxylate ligand selected from the group comprising:

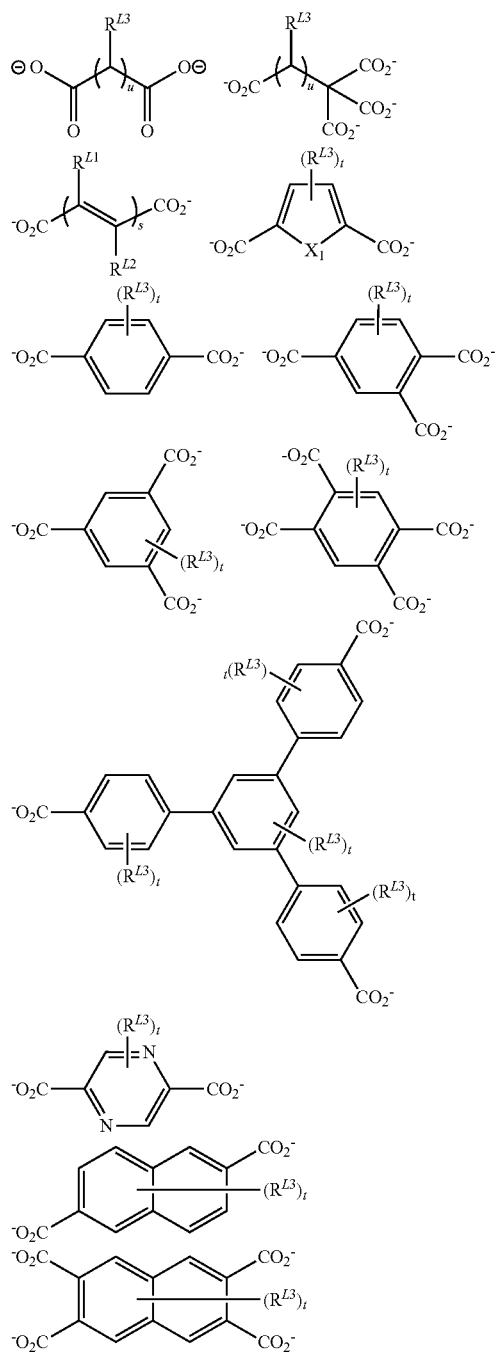

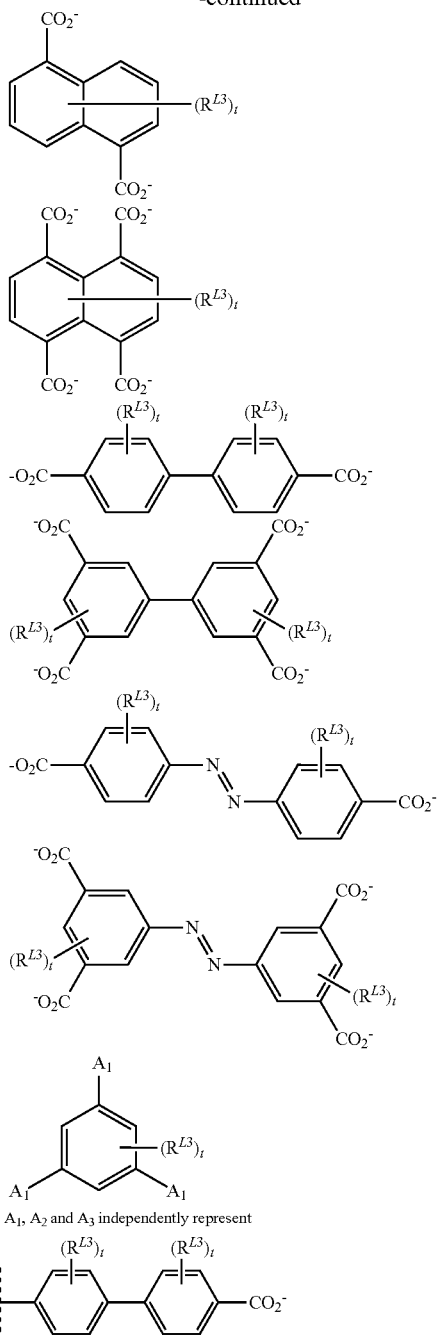

in which:
X$_1$ represents O or S,
s represents an integer from 1 to 4,
each occurrence of t independently represents an integer from 1 to 4,
u represents an integer from 1 to 6,
$R^{L1}$ and $R^{L2}$ independently represent H, a halogen or a C$_1$ to C$_6$ alkyl (preferably methyl or ethyl), and
each occurrence of $R^{L3}$ independently represents H, a halogen (preferably F, Cl or Br), OH, NH$_2$, NO$_2$ or a C$_1$ to C$_6$ alkyl (preferably methyl or ethyl).

In particular, the ligand L of the moiety of formula (I) in the MOF solids of the present invention can be a di-, tri-, tetra- or hexacarboxylate ligand selected from the group comprising:

$C_2H_2(CO_2^-)_2$ (fumarate), $C_2H_4$ $(CO_2^-)_2$ (succinate), $C_3H_6$ $(CO_2^-)_2$ (glutarate), $C_4H_4$ $(CO_2^-)_2$ (muconate), $C_4H_8$ $(CO_2^-)_2$ (adipate), $C_5H_3S(CO_2^-)_2$ (2,5-thiophenedicarboxylate), $C_6H_4(CO_2^-)_2$ (terephthalate), $C_6H_2N_2$ $(CO_2^-)_2$ (2,5-pyrazine dicarboxylate) $C_7H_{16}$ $(CO_2^-)_2$ (azelate), $C_{10}H_6(CO_2^-)_2$ (naphthalene-2,6-dicarboxylate), $C_{12}H_8$ $(CO_2^-)$ (biphenyl-4,4'-dicarboxylate), $C_{12}H_8N_2(CO_2^-)_2$ (azobenzenedicarboxylate), $C_{12}H_6Cl_2N_2(CO_2^-)_2$ (dichloroazobenzenedicarboxylate), $C_{12}H_6N_2$ $(CO_2^-)_4$ (azobenzenetetracarboxylate), $C_{12}H_6N_2$ $(OH)_2$ $(CO_2^-)_2$ (dihydroxoazobenzenedicarboxylate), $C_6H_3(CO_2^-)_3$ (benzene-1,2,4-tricarboxylate), $C_6H_3$ $(CO_2^-)_3$ (benzene-1,3,5-tricarboxylate), $C_{24}H_{15}$ $(CO_2^-)_3$ (benzene-1,3,5-tribenzoate), $C_{42}H_{27}(CO_2^-)_3$ (1,3,5-tris[4'-carboxy(1,1'-biphenyl-4-yl)benzene), $C_6H_2(CO_2^-)_4$ (benzene-1,2,4,5-tetracarboxylate, $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6$ $(CO_2^-)_4$ (biphenyl-3,5,3',5'-tetracarboxylate, and the modified analogs selected from the group comprising 2-aminoterephthalate, 2-nitroterephthalate, 2-methylterephthalate, 2-chloroterephthalate, 2-bromoterephthalate, 2,5-perfluoroterephthalate, 2,5-dihydroxoterephthalate, tetrafluoroterephthalate, 2,5-dicarboxyterephthalate, tetramethyl-4,4'-biphenyldicarboxylate and dicarboxy-4,4'-biphenyldicarboxylate.

Most of the carboxylate ligands listed above are commercially available. The reader can to refer to the Examples section for the preparation of the non-commercially available carboxylate ligands.

In particular, the anion X of the moiety of formula (I) of the present invention can be selected from the group comprising $OH^-$, $Cl^-$, $Br^-$, $R-(COO)_n^-$, $PF_6^-$, $NO_3^-$, $SO_4^{2-}$ and $ClO_4^-$, with R and n as defined above. In one particular implementation mode, the anion X can be selected from the group comprising $OH^-$, $Cl^-$, $F^-$ and $R-(COO)_n^-$ where R represents $-CH_3$, $-C_6H_3$, $-C_6H_4$, $-C_{10}H_4$ or $-C_6(CH_3)_4$.

In particular, the MOF solid according to the invention can contain a percentage by weight of M in the dry phase from 5 to 50%, preferably from 18 to 31%.

The percentage by weight (wt. %) is a measurement unit used in chemistry and metallurgy to describe the composition of a mixture or an alloy, in other words the proportions of each component in the mixture.

1 wt. % of a component=1 g of the component per 100 g of mixture or again 1 kg of said component per 100 kg of mixture.

The MOF solids of the present invention have in particular the advantage of exhibiting thermal stability up to a temperature of 350° C. More particularly, these solids exhibit thermal stability from 120° C. to 350° C.

As previously stated, in the MOF solids of the invention, at least one part of the molecule or molecules containing at least one unsaturation (Lewis base) coordinates with M. Advantageously, at least 1 to 5 mmol of said molecule per gram of dry solid coordinates with M.

The part of the molecule or molecules containing at least one unsaturation which does not coordinate with M can advantageously fill the free space in the pores.

The inventors have demonstrated that the MOF materials containing a three-dimensional structure of moieties of formula (I) take the form of a rigid or flexible structure. In fact, an MOF material can swell and shrink causing the aperture of the pores to vary depending on the nature of the molecules adsorbed which can be, for example, solvents and/or gases.

In the sense of the present invention, "rigid structure" is understood to mean structures which swell or contract only very slightly, in other words with an amplitude up to 10%.

In the sense of the present invention "flexible structure" is understood to mean structures which swell or contract with high amplitude, in particular with an amplitude greater than 10%, preferably greater than 50%. In particular, an MOF material of flexible structure can swell or contract with an amplitude of 10% to 300%, preferably 50 to 300%.

The present invention can be implemented with MOF materials of rigid or flexible structure.

Experimental results have demonstrated that MOF materials of rigid structure were suitable for the implementation of the present invention.

Advantageously, the MOF solid of the present invention is in the form of a robust structure, which has a rigid framework and only contracts very slightly when its pores are emptied of their content which can be, for example, solvent, non-coordinated carboxylic acid, etc. In particular, the MOF solid according to the invention can have a rigid structure which swells or contracts with an amplitude ranging from 0 to 10% depending on the nature of the molecules adsorbed which can be, for example, solvents and/or gases.

The structures of the MOF solids can for example be built up on the basis of chains or trimers of octahedra.

According to one embodiment of the invention, the MOF solid of rigid structure can have a weight percentage of M in the dry phase of 5 to 50%, preferably 18 to 31%. Advantageously, M here will represent iron.

The MOF solid of rigid structure according to the invention can have a pore size of 0.4 to 6 nm, in particular 0.5 to 5.2 nm, more particularly 0.5 to 3.4 nm.

The MOF solid of rigid structure according to the invention can have a pore volume of 0.5 to 4 cm$^3$/g, in particular 0.05 to 2 cm$^3$/g.

In the context of the invention, the pore volume signifies the volume accessible to the molecules of gas and/or liquid.

In particular, the MOF solid according to the invention can have a specific surface area (BET) of 5 to 6000 m$^2$/g, preferably 5 to 4500 m$^2$/g.

In one particular embodiment of the invention, the MOF solid of flexible structure can have a weight percentage of M in the dry phase of 5 to 40%, preferably 18 to 31%. Advantageously, M here will represent iron.

For example, in the context of the invention, the MOF solid of flexible structure can have a pore size of 0.4 to 6 nm, in particular 0.5 to 5.2 nm, and more particularly 0.5 to 1.6 nm.

For example, the MOF solid of flexible structure according to the invention can have a pore volume of 0 to 3 cm$^3$/g, in particular 0 to 2 cm$^3$/g.

The MOF solid of the invention can have a pore volume of 0 to 4 cm$^2$/g, in particular 0.5 to 4 cm$^2$/g.

The MOF solid of the invention can have a loading capacity in molecules containing at least one unsaturation of 0.5 to 50 mmol of substance per gram of dry solid.

In the context of the present invention, the loading capacity signifies the storage capacity for molecules or the quantity of molecules adsorbed in the material. The loading capacity can be expressed in weight capacity (gram/gram) or in molar capacity (mol/mol) or in other units (mol/gram, gram/mol, etc.)

Different MOF materials, named "MIL" (for "Matériau Institut Lavoisier"), have been developed by the inventors at the Institut Lavoisier de Versailles. The "MIL" name of these structures is followed by an arbitrary number n given by the inventors to identify the different solids.

Other structures are named "PIZA" (for "Porphyrinic Illinois Zeolite Analogue") or "CPO" (for "Coordination Polymer Oslo").

The nomenclatures MIL, PIZA and CPO are conventional nomenclatures in the technical field in question, which are well known to those skilled in the art. They are in fact generally used in scientific publications.

A certain number of structures have been brought to the fore by the inventors at this date. These are in particular the structures named MIL-88A, MIL-89, MIL-100, MIL-101, MIL-102, MIL-88B_4CH3, MIL-88B_2OH, MIL-126, MIL-127, CPO-27 and PIZA-1.

The crystallographic characteristics of these structures are known, and have been the subject of many reports. For example the following will be mentioned:

MIL-88A: (a) Serre et al., "Role of solvent-host interactions that lead to very large swelling of hybrid frameworks", Science, 2007, Vol. 315, 1828-1831 [ref 33], (b) Surblé et al., "A new isoreticular class of metal-organic frameworks with the MIL-88 topology", Chem. Comm., 2006, 284-286 [ref 47], (c) Mellot-Draznieks et al., "Very large swelling in hybrid frameworks: a combined computational and power diffraction study", J. Am. Chem. Soc., 2005, Vol. 127, 16273-16278 [ref 48]. The structure of a hydrated MIL-88A solid is shown in FIG. 40, and the crystallographic data are listed in the above publications.

MIL-88B to D: Serre et al., "Role of solvent-host interactions that lead to very large swelling of hybrid frameworks", Science, 2007, Vol. 315, 1828-1831 [ref 33].

MIL-89: C. Serre, F. Millange, S. Surblé, G. Férey *Angew. Chem. Int. Ed.* 2004, 43, 6286: A new route to the synthesis of trivalent transition metals porous carboxylates with trimeric SBU [ref 17]. The structure of an MIL-89 solid is shown in FIG. 41, and the crystallographic data are listed in the above publication.

MIL-100: Horcajada et al., "Synthesis and catalytic properties of MIL-100(Fe), an iron(III) carboxylate with large pores", Chem. Comm., 2007, 2820-2822 [ref 28]. The structure of an MIL-100 solid is shown in FIGS. 18 and 19, and the crystallographic data are listed in the above publication.

MIL-101: Férey et al., "A chromium terephthalate-based solid with unusually large pore volumes and surface area", Science, 2005, Vol. 309, 2040-2042 [ref 49]. The structure of an MIL-101 solid is shown in FIG. 31, and the crystallographic data are listed in the above publication.

MIL-102: S. Surblé, F. Millange, C. Serre, T. Düren, M. Latroche, S. Bourrelly, P. L. Llewellyn and G. Férey "MIL-102: A Chromium Carboxylate Metal Organic Framework with Gas Sorption Analysis" *J. Am. Chem. Soc.* 128 (2006), 46, 14890 [ref 50]. The structure of an MIL-102 solid is shown in FIG. 32, and the crystallographic data are listed in the above publication.

MIL-88B_4CH3, MIL-88B 2OH: For this structural type, the reader will be able to refer to the publications relating to the above type MIL-88, namely (a) Serre et al., "Role of solvent-host interactions that lead to very large swelling of hybrid frameworks", Science, 2007, Vol. 315, 1828-1831 [ref 33], (b) Surblé et al., "A new isoreticular class of metal-organic frameworks with the MIL-88 topology", Chem. Comm., 2006, 284-286 [ref 47], (c) Mellot-Draznieks et al., "Very large swelling in hybrid frameworks: a combined computational and power diffraction study", J. Am. Chem. Soc., 2005, Vol. 127, 16273-16278 [ref 48]. The structure of an MIL-88B4CH$_3$ solid is shown in FIG. 33, and the crystallographic data are listed in the above publications.

MIL-127: Y. Liu and al, Angew. Chem. Int. Ed. 2007, 46, 3278-3283 [ref 51]. The crystallographic data for this material are listed in the above publication.

PIZA-1: "A functional zeolite analogue assembled from metalloporphyrins", M. E. Kosal, J-H Chou, S. R. Wilson, K. S. Suslick, Nature, 2002, 1, 118-121 [ref 52]. The crystallographic data for this material are listed in the above publication.

CPO-27: "Hydrogen adsorption in a nickel based coordination polymer with open metal sites in the cylindrical cavities of the desolvated framework", P. D. C. Dietzel, B. Panella, M. Hirscher, R. Blom, H. Fjellvag, *Chem. Commun.*, 2006, 959-961 [ref 53]. The crystallographic data for this material are listed in the above publication.

Thus, the inventors have demonstrated that the MOF materials having a three-dimensional structure of moieties of formula (I) can exist in different phases, depending on their composition and/or their mode of preparation. For example the MOF materials whereof the moiety of formula (I) corresponds to one of the following formulae will be cited:

$M_3OX[C_6(CH_3)_4(CO_2)_2]_3$/for example MIL-88B_4CH$_3$
$M_3OX[C_6H_3(CO_2)_3]_2$ for example MIL-100
$M_3OX[C_6H_4(CO_2)_2]_3$ for example MIL-101
$M_6O_2X_2[C_{10}H_2(CO_2)_4]_3$ for example MIL-102 or MIL-126
$Fe_6O_2[C_{12}H_6N_2-(CO_2)_4]_3 \cdot X_2 \cdot nH_2O$ for example MIL-127
[CoT(p-CO2)PPCo1.5] for example PIZA-1
$Fe_2(_2OC-C_6H_2(OH)_2-CO_2)(H_2O) \cdot xH_2O$ for example CPO-27 in which X is as previously defined.

Moreover, the inventors have demonstrated that MOF materials having moieties of the same general formula (I), but having different structures, can be obtained from a same carboxylic acid ligand L and the same metal bases (trimers). This is for example the case with the MOF materials MIL-88B_4CH$_3$ and MIL-101. In fact the difference between the MIL-88Btetra (i.e. MIL-88B_4CH$_3$) and MIL-101 solids lies in the modes of connection of the ligands to the octahedron trimers: in the MIL-101 solid, the ligands L assemble in the form of rigid tetrahedra, whereas in the MIL-88B solid they form trigonal bipyramids, making the separation between the trimers possible.

The mode of assembly of these ligands can be controlled during the synthesis for example by adjustment of the pH. For example, the MIL-88 solid is obtained in a less acidic medium than the MIL-101 solid as described in the "Examples" section below.

Advantageously, an MOF material of rigid structure is used in order to obtain better diffusivity properties in the solid during the separation.

Thus, in one particular implementation mode, the MOF solid comprises a succession of the following moieties of formula (I):

$M_3OX[C_6H_3(CO_2)_3]_2$ (structure of MIL-100 type)
$M_3OX[C_6H_4(CO_2)_2]_3$ (structure of MIL-101 type)
$M_3OX[C_6(CH_3)_4(CO_2)_2]_3$ (structure of MIL-88B_4CH3 type)
$M_6O_2X_2[C_{10}H_2(CO_2)_4]_3$ (structure of MIL-102 type)
$Fe_6O_2[C_{12}H_6N_2-(CO_2)_4]_3 \cdot X_2 \cdot nH_2O$ (structure of MIL-127 type)

In one particular implementation mode, in the above structures, M represents Fe.

Methods for preparation of MOF materials are well known to those skilled in the art, and will not be enlarged on in the context of the present application. It will simply be noted that, in general, the MOF materials can be prepared by a process comprising at least one reaction step (i) consisting in mixing in a polar solvent:

at least one solution containing at least one inorganic metal precursor present in the form of metal M, a metal salt of M or a coordination complex containing a metal ion of M at least one ligand L' comprising a radical R containing q groups *—C(=O)—R$^3$, where M, q and R are as defined above,

* designates the point of attachment of the group to the radical R,

R$^3$ is selected from the group comprising an OH, an OY, wherein Y is an alkaline cation, a halogen, or an —OR$^4$, —O—C(=O)R$^4$ or —NR$^4$R$^{4'}$ radical where R$^4$ and R$^{4'}$ are C$_{1-12}$ alkyl radicals.

The preparation of MOF materials can preferably be performed in presence of energy which can be supplied for example by heating, such as for example hydrothermal or solvothermal conditions, but also by microwaves, by ultrasound, by grinding, by a process involving a supercritical fluid, etc. The corresponding protocols are those known to those skilled in the art. Non-limiting examples of protocols usable for hydrothermal or solvothermal conditions are for example described in [ref. 18]. For the synthesis by the microwave method, non-limiting examples of usable protocols are for example described in [ref. 19, 20, 21, 22]. The conditions in the presence of a roller mill can for example refer to the publications [ref. 23, 24, 25].

The hydrothermal or solvothermal conditions, the reaction temperatures whereof can vary between 0 and 220° C., are generally effected in glass (or plastic) vessels when the temperature is lower than the boiling point of the solvent. When the temperature is higher or when the reaction is effected in presence of fluorine, teflon vessels inserted in metal bombs are used [ref. 22].

The solvents used are generally polar. In particular the following solvents can be used: water, alcohols, dimethylformamide, dimethyl sulfoxide, acetonitrile, tetrahydrofuran, diethylformamide, chloroform, cyclohexane, acetone, cyanobenzene, dichloromethane, nitrobenzene, ethylene glycol, dimethylacetamide or mixtures of these solvents.

One or more co-solvents can also be added at any step of the synthesis for better dissolution of the compounds of the mixture. They can in particular be monocarboxylic acids such as acetic acid, formic acid, benzoic acid, etc.

One or more additives can also be added in the course of the synthesis in order to modulate the pH of the mixture. These additives are selected from the mineral or organic acids or the mineral or organic bases. By way of example, the additive can be selected from the group comprising: HF, HCl, HNO$_3$, H$_2$SO$_4$, NaOH, KOH, lutidine, ethylamine, methylamine, ammonia, urea, EDTA, tripropylamine and pyridine.

Preferably, the mixing reaction step (i) can be effected according to at least one of the following reaction conditions:

with a reaction temperature of 0° C. to 220° C., preferably 50 to 150° C., with a stirring rate of 0 to 1000 rpm (or rotations per minute), preferably 0 to 500 rpm, with a reaction time of 1 minute to 144 hours, preferably 1 minute to 15 hours, with a pH of 0 to 7, preferably 1 to 5, with the addition of at least one co-solvent to the solvent, to the precursor, to the ligand or to the mixture thereof, said co-solvent being selected from the group comprising acetic acid, formic acid and benzoic acid, in presence of a solvent, which is selected from the group comprising water, the alcohols R$^S$—OH where R$^S$ is a C$_1$ to C$_6$ linear or branched alkyl radical, dimethylformamide, dimethyl sulfoxide, acetonitrile, tetrahydrofuran, diethylformamide, chloroform, cyclohexane, acetone, cyanobenzene, dichloromethane, nitrobenzene, ethylene glycol, dimethylacetamide or mixtures of these solvents, whether or not miscible, in a supercritical medium, for example in supercritical CO$_2$, under microwaves and/or under ultrasound, under conditions of electrochemical electrolysis, under condition using a roller mill, under gas flow.

As previously stated, according to one aspect, the invention relates to a process for separating a mixture of molecules having different unsaturation degrees and/or a different number of unsaturations by preferential adsorption of the molecules with a greater degree and/or number of unsaturations on a porous crystalline MOF solid as defined above, said process comprising at least one reaction step consisting (i) in mixing in a polar solvent:

at least one solution containing at least one inorganic metal precursor taking the form of a metal M, a metal salt of M or a coordination complex containing a metal ion of M, at least one ligand L' comprising a radical R containing q groups *—C(=O)—R$^3$, where M, q and R are as defined above,

* designates the point of attachment of the group to the radical R,

R$^3$ is selected from the group comprising an OH, an OY, wherein Y is an alkaline cation, a halogen or an —OR$^4$, —O—C(=O)R$^4$ or —NR$^4$R$^{4'}$ radical, where R$^4$ and R$^{4'}$ are C$_{1-12}$ alkyl radicals, to obtain an MOF material, (ii) in activating the MOF material obtained in (i), and (iii) in placing the MOF material obtained in step (ii) in contact with a mixture of molecules having different unsaturation degrees and/or a different number of unsaturations.

Thus, prior to the placing of the MOF material in contact with the mixture of molecules having different unsaturation degrees and/or a different number of unsaturations in step (iii), it is necessary that the material derived from step (i) be activated in step (ii).

In one particular implementation mode, the activation step (ii) can have two effects:

it can make it possible to empty the pores of the MOF material and make them accessible for the coordination of the molecule or molecules to be separated.

it can enable the reduction of metal centers M$^{z+}$ of the MOF material obtained in (ii) to M$^{(z-1)+}$ ions in which z represents 3 or 4.

The emptying can take place, for example, by the departure of molecules of water and/or solvents present in the reaction medium either by activation under primary or secondary vacuum or under a current of gas (helium, nitrogen, air . . . ), with or without heating of the solid at a temperature of 25 to 300° C., in particular 50 to 250° C., and more particularly 100 to 250° C. The heating can be effected for a period of time between 1 hour and 96 hours, typically between 3 and 15 hours. The activation is a kinetic phenomenon: the higher the activation temperature, the faster the dehydration, and the faster the reduction. Without wishing to be bound in any way to a particular theory, it seems that it can be proposed that the maximum degree of reduction at a given temperature is without doubt controlled by the thermodynamics.

The activation step (ii) makes it possible in particular to reduce some of the M$^{z+}$ ions of the MOF material obtained in (ii) to M$^{(z-1)+}$ ions. This activation step has the effect of rendering the MOF material more selective towards molecules containing at least one unsaturation. As previously stated, the reduced metal ion $M^{(z-1)+}$ has an additional d electron compared to $M^{z+}$, which reinforces the coordination bond to the molecules containing at least unsaturation and thus increases the stability of the complex formed.

It is understood that not all the metal sites $M^{z+}$ of the MOF material are reduced in this activation step (ii). Only the accessible metal sites are capable of being reduced.

"Accessible metal site" is understood to mean a metal site $M^{z+}$ or $M^{(z-1)+}$ which can coordinate with molecules.

Depending on the conditions of activation (ii), the accessible metal centers of the MOF material can be partially or even totally reduced. "Partially reduced" is understood to mean the reduction of less than 100% of the accessible metal sites $M^{z+}$ to corresponding $M^{(z-1)+}$ ions. According to one particular implementation mode, the fraction of reduced ions $M^{(z-1)+}$ relative to the metal ions $(y=M^{(z-1)+}/M^{z+})$ is strictly greater than zero.

In one implementation mode, the process according to the invention can further contain a step (i') of treatment of the MOF material obtained in step (i) with a source of $F^-$ ions, such as for example, KF, CsF, LiF, $MgF_2$, $CaF_2$, or an amine fluoride salt such as $NH_4F$. Advantageously, the source of ions $F^-$ is $NH_4F$, for example in aqueous solution. The material thus obtained can then be subjected to the steps (ii) and (iii) as previously defined. In that case, the temperature used in the activation step (ii) will generally be lower than that which is used when the material is not subjected to the treatment with a source of $F^-$ ions.

According to one implementation mode, M can represent $Fe^{3+}$ and not more than one third of the metal sites $Fe^{3+}$ are reduced to $Fe^{2+}$ ions. These are generally MOF solids not containing redox ligands (oxidation of which can lead to a charge compensation making it possible to obtain values of x greater than ⅓). In that scenario, y=⅓ corresponds to the theoretical maximum activation of the MOF material by reduction of the $Fe^{3+}$ sites by the auto-reduction phenomenon (i.e. in an initial period, a temperature <150° C., or even <100° C., makes it possible to remove the molecules of water and solvent coordinated onto the $M^{z+}$ sites. Above 100° C., in particular above 150° C., the $M^{z+}$ sites start to be reduced. The reduction can be accompanied by the elimination of a negatively charged ligand (−1) to preserve the electrical neutrality of the MOF solid). In other words, according to one particular mode of the invention, M=Fe and the ratio $y=M^{(z-1)+}/M^{z+}$ can be less than or equal to ⅓. Thus, in one particular implementation mode, M can represent Fe and the ratio $y=M^{(z-1)+}/M^{z+}$ can lie between 0<y≤⅓.

According to another implementation mode, M can represent Fe, the porous MOF solid contains at least one redox ligand capable of being oxidized and y can take any value lying between ⅓ and 1. For example, it can be a ligand of the hydroquinone (reduced form) or quinone (oxidized form) type. For example the ligand 2,5-dihydroxoterephthalic acid could be cited. An example of an MOF solid of this type is the iron carboxylate MIL-88B-2OH(Fe), $Fe_3O[C_6H_2(OH)_2-(CO_2)_2]_3 \cdot X \cdot nH2O$ (X=F, Cl, OH). See example 31 for a practical example.

The metal centers of the same MOF material can derive from identical or different metals, for example solely iron, or from several metals, such as iron in presence of manganese and/or of cobalt.

When the accessible metal centers are in part reduced, in particular if some of the iron is at the oxidation level +II (z=3), some of the manganese at the oxidation level +II (z=3) and/or some of the cobalt at the oxidation level +II (z=3) and/or some of the vanadium IV has been reduced to the oxidation level +III (z=4), some of the molecules of the mixture can then coordinate more strongly to the metal by a retrodonation effect.

Retrodonation is understood to mean the transfer of the electron density of the metal M into an anti-bonding orbital of the molecule containing at least one unsaturation. This leads to an increase in the number of molecules containing at least one unsaturation coordinated per metal center. The final MOF solid will then contain a greater quantity of molecules coordinated to the reduced metal ions. The resulting MOF solids will then possess greater selectivity in the separation of mixtures of molecules having different unsaturation degrees and/or a different number of unsaturations. The presence of the reduced ions $M^{(z-1)+}$ makes it possible in particular to increase the affinity of the MOF solid with regard to the molecules with a greater degree and/or number of unsaturations in a given mixture (for example, molecules containing two double bonds will be adsorbed on the MOF solid preferent-ially to those having one double bond).

The reduction step (ii) thus makes it possible to obtain an MOF material capable of being used for the differential separation of molecules having different unsaturation degrees and/or a different number of unsaturations, the molecules having comparatively greater degrees and/or number of unsaturations will reside longer in the material (due to a greater affinity of the reduced metal ions $M^{(z-1)+}$ for the molecules containing unsaturations).

Furthermore, the proportion of reduced metal centers has an influence on the residence time of the molecules of the mixture in the MOF solid, this increasing substantially. The greater the content of reduced ions in the MOF solid, the greater will be the residence time of the molecules with a greater degree and/or number of unsaturations in the MOF solid.

The activation step (ii) can be effected by any means making it possible to dehydrate the MOF material (removal of the molecules of water coordinated at the $M^{z+}$ sites) and to result in the reduction of at least some of the accessible $M_{z+}$ sites to $M^{(z-1)+}$ ions.

In one implementation mode, the activation step (ii) can be effected at a high temperature under a neutral or reducing atmosphere, or under reduced pressure.

In one implementation mode, the activation step (ii) can be effected at a high temperature under a current of inert gas, such as helium, argon, nitrogen, or a mixture thereof. For example, the activation step (ii) can take place between 25 and 400° C., more particularly between 100 and 300° C., and quite particularly between 150 and 280° C., under a current of helium In one implementation mode, the activation step (ii) can be effected at a high temperature under a reducing atmosphere, such as $H_2$, CO or NO. For example, the activation step (ii) can take place between 25 and 400° C., more particularly between 100 and 300° C., and quite particularly between 150 and 280° C., under a hydrogen gas atmosphere.

In one particular implementation mode, the activation step (ii) can be implemented at a high temperature and under reduced pressure. Reduced pressure is understood to mean a pressure ranging from 1 to $10^{-5}$ Pa, advantageously from 1 to $10^{-2}$ Pa or even from $10^{-3}$ to $10^{-5}$ Pa.

For example, the activation step (ii) can take place at 50-250° C. under a pressure of 1 to $10^{-2}$ Pa, or $10^{-3}$ to $10^{-5}$ Pa.

It is understood that the temperature conditions used will depend on the MOF material used. They may also depend on whether or not a possible pretreatment of the material with a source of $F^-$ ions (such as KF, CsF, LiF, $MgF_2$, $CaF_2$, or an amine fluoride salt such as $NH_4F$) has been performed. For example, this may be a treatment of the MOF material with an aqueous solution of $NH_4F$ at 70° C. for 24 hours.

In general, the aforesaid temperature and pressure conditions can also be used when the porous MOF solid has previously been subjected to treatment with a source of $F^-$ ions (such as KF, CsF, LiF, $MgF_2$, $CaF_2$, or an amine fluoride salt such as $NH_4F$). Thus, for an MOF previously treated with a source of $F^-$ ions, the activation step (ii) can take place at 50-250° C. under a pressure of 1 to $10^{-2}$ Pa, or $10^{-3}$ to $10^{-5}$ Pa.

Advantageously, the temperature in the activation step (ii) will not exceed the degradation temperature of the MOF solid. In one particular implementation mode, the activation step (ii) is performed at a temperature of 25 to 300° C., advantageously 50 to 250° C. From the industrial point of view, the selection of the activation conditions can be made on the basis of practical considerations (cost, availability of the gas selected, etc. . . . ).

Once the activation step (ii) has been effected, the partially reduced MOF solid can be stored under vacuum or under an inert atmosphere to protect it from possible reoxidation. Alternatively, the partially reduced MOF solid obtained at the end of step (ii) can be used directly for step (iii) of the process.

In step (iii) of the process of the invention, the MOF material activated in step (ii) is placed in contact with a mixture of molecules having different unsaturation degrees and/or a different number of unsaturations. The mixture can be in gaseous form or in the liquid phase.

When the mixture is in gaseous form, this can be separated as such, or mixed with an inert gas (the inert gas being able to act as a carrier gas).

When the mixture is in the liquid phase, the mixture can be solvated in a solvent or mixture of solvents. Preferably, the solvent(s) contain no unsaturations in the sense of the present invention so that contact with the solvent does not lead to poisoning of the unsaturated sites of the MOF solid. For example, they may be saturated hydrocarbons.

The contacting of the MOF solid with the mixture of molecules in step (iii) can be performed at a temperature ranging from −150 to 200° C.

Furthermore, step (iii) can be performed at a pressure ranging from $10^4$ to $10^7$ Pa.

Those skilled in the art will know how to select the temperature and pressure ranges to effect the separation of a given mixture, depending on the composition of the mixture, the nature of the MOF solid (MOF solid based on Fe, Mn, Co, Ni, V or mixed), the content of $M^{(z-1)+}$ ions, the separation conditions (gaseous or liquid phase, thermodynamic separation or under dynamic flow), and the desired separation profile (separation time, resolution). In general, the selection of the temperature and pressure conditions will depend on the separation process used (for example, fractionation of air by modulated pressure adsorption ("Pressure Swing Adsorption") or simulated moving bed) and the costs of implementation of the process. In the selection of the temperature and pressure conditions, those skilled in the art will be guided by considerations relating to the performance-energy cost compromises.

By way of example, temperature and pressure conditions are given below for some particular mixtures. In one particular implementation mode, the mixture of molecules is a mixture of at least one saturated hydrocarbon and at least one unsaturated hydrocarbon. This can for example be a mixture of at least one paraffin (alkane) and at least one olefin (alkene). It can also be a mixture of at least one olefin and at least one alkyne. For example, this can be mixtures of C2, C3, C4 or C5 hydrocarbons. By way of example, the following may be cited:

propane/propylene,
n-butane/isobutene,
n-butane/mixture of butenes,
acetylene/ethylene Propane/Propylene Propane-propylene mixture separation is of considerable industrial importance in the chemical and petrochemical industry. For nearly 60 years, propane/propylene separation has been performed by an energetically very costly process of cryogenic distillation at −30° C. (243 K) and 30 psig (0.308 MPa) in a column containing nearly 100 plates. The reason for these extreme conditions derives from the very close boiling points of these two hydrocarbons.

Propylene is one of the basic precursors of a large number of polymers. Its recovery from the streams derived from refineries is used intensively to meet the needs of industrial manufacturers of polymers based on propylene. To meet the corresponding specifications, the industrial stream must contain at least 99.5% of propylene and be free from traces of diolefins and acetylene.

Butane/Isobutene

Isobutene is reagent for polymerization. Isobutene must have a purity level greater than 99% and no longer contain more than traces of 1-butene and 2-butenes (a few hundred parts per million by weight, ppm). In fact, if the impurity level in the isobutene is too high, the polymers obtained are of less good quality and the polymerization yield is lower. It is therefore necessary to eliminate the other olefinic hydrocarbons from a hydrocarbon cut containing isobutene.

The difficulty in this case is that since 1-butene and isobutene have very similar boiling points, it is not possible to separate them economically by distillation.

The main problem which arises for producing isobutene of high purity is thus the separation of the 1-butene from the isobutene (see WO 98/006684 [ref. 45]).

Acetylene/Ethylene

Acetylene is a secondary product obtained during the production of ethylene, and acts as a poison for the catalysts used to manufacture polyethylene from ethylene. Consequently, the ethylene-based polymer must not contain more than 5 ppm of acetylene. Removing these traces of acetylene is thus a real challenge for the manufacturers of ethylene and the suppliers of catalysts on account of the low concentrations of acetylene in the reactors and their almost total conversion under these conditions.

Further, acetylene can form metal acetylides which are explosive contaminants. It is therefore essential to reduce the concentration of acetylene in the ethylene stream to an acceptable extent. (For further information, the reader can refer to http://kolmetz.com/Article-039.htm)

A particularly important use of the MOF materials of the invention relates to the separation of olefins and paraffins. As aforesaid, the recovery of olefins from mixtures of olefins and paraffins is one of the most important problems in the separation field. Let us mention for example ethylene and propylene which are fundamental precursors for the synthesis of many polymers such as polyethylene or polypropylene. The current separation technologies are very costly and have many disadvantages. In view of their ease of implementation, relatively low cost and the structural and electronic properties disclosed in the present, the MOF materials of the invention constitute a valuable alternative for olefin/paraffin separation on the industrial scale.

Thus, in one particular implementation mode, the mixture to be separated is a mixture of propane and propene. In this implementation mode, step (iii) can be performed at a temperature of 0° C. to +150° C. In this implementation mode, step (iii) can be performed at a pressure of $10^4$ to $10^6$ Pa. In this implementation mode, the MOF material obtained in step (ii) advantageously has an adsorption capacity for propane and/or for propene lying between 0.5 and 20 mmol/g.

In one particular implementation mode, the mixture to be separated is a mixture of ethane and ethylene. In this implementation mode, step (iii) can be performed at a temperature of 0° C. to +150° C. In this implementation mode, step (iii) can be performed at a pressure of $10^4$ to $10^6$ Pa. In this implementation mode, the MOF material obtained in step (ii) advantageously has an adsorption capacity for ethane and/or for ethylene lying between 0.5 and 20 mmol/g.

In one particular implementation mode, the mixture to be separated is a mixture of isobutane and isobutene. In this implementation mode, step (iii) can be performed at a temperature of 0° C. to +150° C. In this implementation mode, step (iii) can be performed at a pressure of $10^4$ to $10^6$ Pa. In this implementation mode, the MOF material obtained in step (ii) advantageously has an adsorption capacity for isobutane and/or for isobutene lying between 0.5 and 20 mmol/g.

In one particular implementation mode, the mixture of molecules is a mixture of at least one compound containing one or more free electron pair(s) and of at least one compound not containing a free electron pair. In one particular implementation mode, the mixture of molecules is a mixture of at least one saturated hydrocarbon and at least one unsaturated hydrocarbon or carbon dioxide. For example, it can be a mixture of acetylene and carbon dioxide, or else a mixture of hydrogen ($H_2$) and carbon monoxide and/or dioxide.

It can also be a mixture of propane and propene, a mixture of n-butane and isobutene, a mixture of n-butane and butenes, a mixture of acetylene and ethylene, a mixture of acetylene and carbon dioxide, a mixture of CO and hydrogen ($H_2$), a mixture of $CO_2$ and hydrogen ($H_2$), a mixture containing hydrogen ($H_2$) and at least one unsaturated hydro-carbon and/or at least one compound containing one or more free electron pair(s) or a mixture of hydrogen ($H_2$) and other gases (olefins, alkynes, carbon monoxide, carbon dioxide, . . . ).

In one particular implementation mode, the mixture of molecules is selected from:
- a mixture of at least one saturated hydrocarbon and at least one unsaturated hydrocarbon,
- a mixture of at least one compound containing one or more free electron pair(s) and at least one compound not containing a free electron pair, and
- a mixture of hydrogen ($H_2$) and carbon monoxide and/or dioxide.

In one particular implementation mode, the mixture of molecules is selected from:
- a mixture of at least one paraffin and at least one olefin.
- a mixture of at least one olefin and one alkyne.
- a mixture of acetylene and carbon dioxide.
- a mixture of hydrogen ($H_2$) and carbon monoxide and/or dioxide.

In fact, a particularly interesting use of the MOF materials of the present invention is the purification of hydrogen ($H_2$) by elimination of traces of CO and/or $CO_2$. At present the demand for hydrogen ($H_2$) is very great for fuel cell applications, this technology being considered as one of the most promising for meeting the energy needs of the future [ref. 26]. Hydrogen ($H_2$) is generally produced by steam-reforming from a natural gas or other fossil fuels. Reforming is a thermochemical process by which fuels containing hydrogen ($H_2$) are transformed into a gaseous mixture rich in $H_2$.

The steam-reforming reaction is generally performed at a high temperature of 400 to 700° C. over catalysts based on nickel deposited on an alumina support, and is accompanied by the formation of carbon monoxide. Generally, the steam-reforming is followed by a reaction in presence of water (water-gas reaction) to oxidize the carbon monoxide to carbon dioxide.

For the requirements of fuel cells, it is necessary to purify the hydrogen ($H_2$) produced industrially by the aforesaid processes. The purification methods currently used are based on platinum sponge membranes, which are extremely expensive and increasingly rare. The MOF materials of the present invention can be used for this purpose, namely to separate the traces of CO and $CO_2$ from the hydrogen ($H_2$). In fact, CO and $CO_2$ can be separated from the hydrogen ($H_2$), which contains no unsaturation, by the process of the invention.

Thus, the present invention extends to the use of the MOF solids and the process according to the invention for the purification of hydrogen ($H_2$). According to one aspect, the present thus relates to a process for purifying hydrogen. Thus, in one implementation mode, the mixture of molecules at step (iii) of the process of the invention can be a mixture of $H_2$, CO and $CO_2$.

Another use of the MOF materials of the present invention of considerable industrial interest is the separation of acetylene from carbon dioxide. Acetylene is an instrumentation gas used as a combustion gas in atomic absorption spectrometry for elemental analysis and in optical spectrometry.

It is a synthetic gas derived from the reaction between calcium carbide and water:

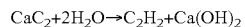

$$CaC_2+2H_2O \rightarrow C_2H_2+Ca(OH)_2$$

It can also be obtained by partial combustion of methane:

$$3CH_4+3O_2 \rightarrow C_2H_2+CO+5H_2O$$

Acetylene and carbon dioxide, which are most often present in $CO_2$ recovery processes, have very similar characteristics (size), hence they are difficult to separate by distillation (whether or not cryogenic). For more details on the problem of $CO_2$ recovery, the reader can for example refer to the U.S. Pat. No. 6,024,781 [ref. 44].

Thus, the present invention extends to the use of the MOF solids and of the process according to the invention for the separation of acetylene from carbon dioxide. According to one aspect, the present thus relates to a process for separating acetylene from carbon dioxide. Thus, in one implementation mode, the mixture of molecules at step (iii) of the process of the invention can be a mixture of acetylene and carbon dioxide.

The invention also relates to the use of the MOF materials as defined above for:
- air purification (in particular to reduce the level of, or even remove the traces of, $CO_2$, $H_2O$, $N_2O$ and oil in air streams),
- the separation of mixtures of $CO_2$ and hydrocarbons (for example $CO_2$/ethylene mixtures),
- trapping traces of water in gaseous mixtures (use as a desiccating agent).

In one particular implementation mode, the process of the invention can further comprise a step (iv) of desorption of the molecules with a greater degree and/or number of unsaturations on the porous crystalline MOF solid of the invention. The desorption can be effected by any means known in the field of separations on solid phase. For example, the desorption can be effected by a desorption technique selected from displacement with another gas, a pressure change, a temperature change, or a combination thereof. For example, the desorption can be effected by displacement with a pure or essentially pure gas (for example at least 98% pure) at low pressure, between 1 and 8 bars for example. The desorption can also be effected by the combination of a temperature change and a pressure change. Those skilled in the art will know how to select the temperature/pressure combination depending on the process used and the mixture to be separated.

Thus, in one aspect, the present invention is based on the activation of porous metal carboxylate MOF materials having unsaturated reducible metal centers (Fe, Mn, Ni, V and/or Co) in order to improve their separation properties for molecules having at least one unsaturation (for example paraffin/olefin mixtures).

In practice, it is a matter of partially reducing the metal center beforehand by activation under vacuum (or under a reducible or neutral atmosphere) in order to increase the affinity of the metal, by a retrodonation effect, for the molecules of a given mixture having a greater degree and/or number of unsaturations (for example the alkenes (or alkynes)) compared to molecules of the same mixture having a lower degree and/or number of unsaturations (for example the alkanes).

In one particular implementation mode, the MOF materials in question are porous iron(III) carboxylates, of rigid structure, based on trimers of octahedra which possess a substantial quantity of unsaturated metal centers (1-3 mmol·g$^{-1}$). The activation makes it possible to lead to reduction of up to 33% of the iron initially present in the form of iron(III).

The MOF materials of the present invention thus enable the separation of said mixtures of molecules having different unsaturation degrees and/or numbers of unsaturations (for example, alkene/alkane (or alkyne/alkene) mixtures) in dynamic flow under pressure. The separation is based on the differences in affinity between the molecules of the mixture to be separated and the MOF material, in particular the unsaturated metal sites $M^{(z-1)+}$ which have a strong affinity for unsaturations.

A unique property of the MOF materials of the invention is the modulation of the level of reduced ions $M^{(Z-1)+}$ in the MOF material by carefully controlled prior activation (for example, given activation time and/or temperature) also makes it possible to optimize and/or adapt the performance of the MOF material (selectivity, regeneration, diffusion) depending on the industrial process chosen, in particular depending on the mixture of molecules to be separated.

One advantage of the MOF materials of the present invention is that they can be obtained in pure, and homogeneous, crystalline form, in a reduced number of steps and in high yields. This reduces the duration of the synthesis and the production costs.

On the other hand, the MOF materials of the present invention are characterized by the fact that the structure of the MOF material remains stable after reduction of metal ions $M^{z+}$ of the material to $M^{(z-1)+}$ ions. This is not the case with the MOF materials based on Cu(II) hitherto studied in the context of the purification of olefins [ref. 14 and 16]. In fact, in these MOF of the prior art, the reduction of the Cu(II) to Cu(I) would entail the destruction of the structure (framework) of the complex. In contrast, the inventors have demonstrated the MOF materials of the invention conserve their structure undamaged when all or some of the accessible $M^{z+}$ ions of the MOF material are reduced to corresponding $M^{(z-1)+}$ ions. This property is demonstrated in the "Examples" section and confers on the MOF materials of the invention specific properties particularly suitable for the separation of mixtures of molecules having different unsaturation degrees and/or a different number of unsaturations.

Furthermore, the inventors have demonstrated that the content of reduced ions $M^{(z-1)+}$ could be modulated depending on the activation temperature and/or time conditions used in the activation step (ii) of the process of the invention (see the "Examples" section, in particular example 5). Thus, higher contents of reduced ions $M^{(z-1)+}$ can be obtained at higher temperature ranges and/or longer activation time.

The inventors have also demonstrated that this content of reduced ions $M^{(z-1)+}$ the selectivity of the MOF material in the separation of mixtures containing molecules having an electron donor (Lewis base) nature. The greater the content of reduced ions $M^{(z-1)+}$, the more affinity the MOF material has for Lewis bases and consequently the greater is the adsorption of molecules with unsaturations.

Thus, one important advantage of the MOF materials of the invention is that the content of reduced ions $M^{(z-1)+}$ can easily be modulated/adjusted depending on the mixture of molecules to be separated. In particular, this is a useful and readily exploitable parameter for modulating the selectivity of the MOF material in the separation of mixtures of molecules having different unsaturation degrees and/or a different number of unsaturations.

Further, since the reduced metal sites $M^{(z-1)+}$ form an integral part of the framework of the MOF material, the washing out or "lixiviation" effect which can be observed for certain materials used in olefin separation methods (for example the zeolites with a silver or copper constituent ("Ag-zeolites" or "Cu-zeolites") obtained by impregnation) does not occur. The term "lixiviation" is generally used to designate washing of solid deposits to extract the soluble compounds from them. In the context of the present invention, "lixiviation" is understood to mean the phenomenon of washing out, or loss of constituents of the separation material, which sometimes affects the separation processes.

Thus, not only does the structure (framework) of the MOF material of the invention remain undamaged after reduction of accessible metal sites $M^{z+}$, but also the reduced metal sites $M^{(z-1)+}$ are not lost/washed out when the separation process is implemented. This therefore avoids the economic costs due to the deterioration of the materials and also prevents possible environmental pollution phenomena.

On the other hand, as previously stated, the temperature required to activate the MOF materials according to step (ii) of the process of the invention is relatively low (from 25 to 300° C., more particularly 100 to 250° C.) compared to the activation temperature of the zeolites used in this field (around 400° C.). The process of the invention thus presents an economic advantage (lower implementation costs).

Another advantage of the MOF materials of the invention is also the possibility of directly shaping monoliths of adsorbents, a necessary step before envisaging the formation of membranes, in order to avoid the typical problems associated with shaping: damage to the porous structure and intra-crystalline mass transfer resistance. [ref. 27]

The inventors have moreover demonstrated that the MOF materials of the invention had an adsorption capacity superior to the zeolites. It will for example be noted that the adsorption capacity of the MOF material MIL-100(Fe) of formula Fe$_3$O[C$_6$H$_3$—(CO$_2$)$_3$]$_2$.X.nH$_2$O (X=F, Cl, OH) for propane and/or propylene is about 11 mmol/g (that is to say close to 172 cm$^3$/cm$^3$ STP ("Standard Temperature and Pressure")) of dry solid (FIG. 12). This is much greater than the adsorption capacity of a zeolite which is from 1 to 3 mmol/g.

On the other hand, a notorious disadvantage of the zeolites is that these have low diffusivity of hydrocarbons in their pores, due in part to the excessively small size of the pores of the zeolites. In contrast, it is expected that the diffusivity of hydrocarbons in the MOF materials of the present invention will be much better. It is well known that the zeolites have diffusivity problems as the pores are smaller [ref. 11].

Consider for example the case of the MIL-100(Fe) solid [ref. 28]. This is constituted of trimers of octahedra of iron linked by trimesic acids which associate to form hybrid supertetrahedra. The whole thus results in a crystallized mesoporous structure, whereof the cages of free dimensions 25 and 29 Å are accessible via microporous windows (FIG. 18). The resulting pore volume is very large, close to 1.2 g·cm$^{-3}$ for a specific BET surface area of 2200 m$^2$·g$^{-1}$. Thus, the removal of the molecules of water or fluorine coordinated onto the iron gives rise to sizes of access windows to the mesoporous cages of large dimension (25/29 Å): 8.5 Å for the pentagonal windows and 12 Å for the hexagonal windows (FIG. 19), that is to say a size greater than that of the large-size zeolite Faujasite (windows of 7 Å and cages of 12 Å). This, combined with the presence of mesoporous cages, the better diffusion of the hydrocarbons (in particular propane and propylene) in the pores of the MIL-100(Fe) compared to the small-sized ones of the zeolites. The separation of these olefins in a solid of such large pore size is no doubt explained by the presence of the unsaturated metal centers M$^{(z-1)+}$ in the windows, these latter "filtering" the molecules before they enter the mesopores. Thus, the MOF materials described in the present are particularly suitable for flow separations, for which the diffusivity properties are important.

On the other hand, it has been demonstrated that the integrity of the MOF materials according to the invention was maintained after several separation cycles (see example 10, and FIG. 14). The MOF materials can therefore be used several times after reactivation, without their structural and/or chemical properties being affected. This is an important aspect as regards their applicability in separation processes on the industrial scale.

Finally, the inventors have demonstrated that although the MOF materials of the invention possess unsaturated metal centers M$^{(z-1)+}$ which are Lewis acid centers, even if these can generate a Brønsted acidity by coordination of proton donor molecules such as water the acidity measured by CO adsorption is not very significant. Thus, in the case of the use of the MOF materials according to the invention for the separation of mixtures containing unsaturated hydrocarbons, the Brønsted acidity of the MOF material is not sufficient to trigger polymerization of the unsaturated hydrocarbon.

Thus, the MOF solids of the present invention represent a viable alternative to the materials conventionally used in separation processes, in particular for the separation/purification of olefins.

Other advantages may appear to those skilled in the art on reading the examples below, illustrated by the appended figures, given by way of illustration.

BRIEF DESCRIPTION OF THE FIGURES

FIG. 17A: propane/propylene mixture. FIG. 17B: n-butane/iso-butene mixture.

FIGS. 43B-43H show the crystallographic data of the MOF solid MIL-126(Fe).

EXAMPLES

Example 1

Figure 1:
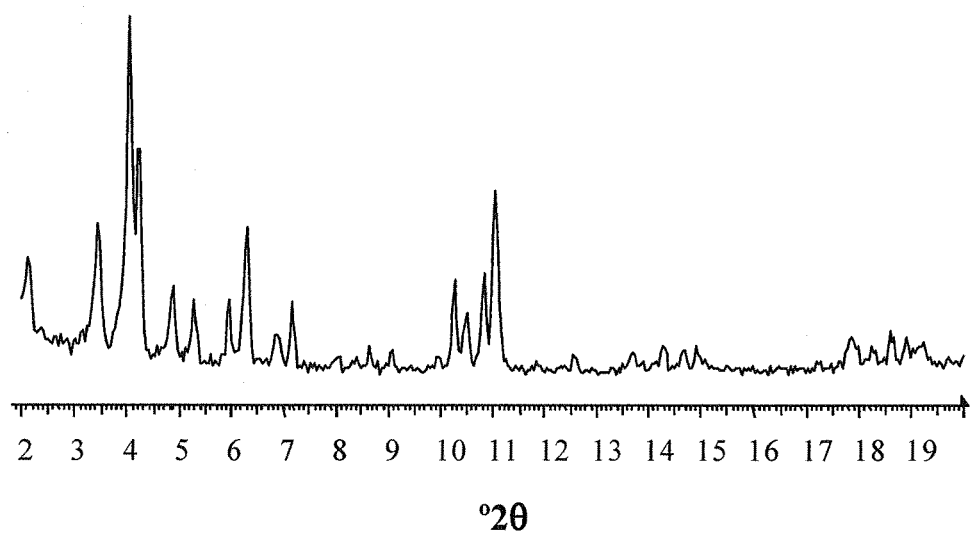
FIG. 1 shows an X-RAY diffraction diagram of the MIL-100(Fe) solid

Synthesis and Data on Iron Carboxylate MOF Materials of the Present Invention

This example describes the synthesis of various iron carboxylates. The solids obtained were then characterized according to the methods described below.

The analysis of the crystal structure of the iron carboxylate solids was performed by X-ray diffraction (X-RAY) using a Siemens D5000 diffractometer (CuKα radiation $\lambda_{Cu}$=1.5406 Å, mode θ-2θ), at ambient temperature in air. The diagrams presented are either in angular distances (2θ, in degrees°) or in inter-reticular distances (d, in Å or Angström).

The porosity (Langmuir specific surface area and pore volume) of the solids was characterized by nitrogen adsorption at 77 K on a Micromeretics ASAP-2010 instrument. The solids were previously dehydrated at 150° C. under primary vacuum for one night. The isotherm of nitrogen adsorption by the solids is given by a curve showing the volume of nitrogen adsorbed V (in cm$^3$/g) as a function of the ratio of the pressure P to the reference pressure P$_0$=1 atm.

Thermogravimetric analysis was performed in air using a TA-instruments 2050 TGA instrument. The heating rate was 2° C./minute. The curve resulting from the thermogravimetric analysis of the solids shows the weight loss Pm (in %) as a function of the temperature T (in ° C.).

Elemental analysis of the solids was performed by the CNRS Vernaison Central Analysis Service:

Organic Analysis:

C, H, N, O, S microanalyses in pharmaceutical products, polymers and the products of synthesis in general, by coulometric, catharometric or infra-red cell detection.

Inorganic Analysis:
Main techniques used:
- ICP-AES ("Inductive Coupled Plasma—Atomic Emission Spectroscopy") with different types of detectors
- ICP-MS ("Inductively Coupled Plasma-Mass Spectrometry") with quadrupole or magnetic sector mass spectrometers
- CVAAS ("Cold-Vapor Atomic Absorption Spectroscopy")
- ICP/MS/HPLC coupling ("Inductively Coupled Plasma/Mass Spectrometry High Performance Liquid Chromatography")
- X-ray fluorescence
- Wet, dry or microwave treatment of samples.

a) MIL-100(Fe) or $Fe_3O[C_6H_3—(CO_2)_3]_2 \cdot X \cdot nH_2O$ (X=F, Cl, OH)

The iron carboxylate MIL-100(Fe) was synthesized under two conditions: with and without hydrofluoric acid.

Conditions for Synthesis with Hydrofluoric Acid:

56 mg of powdered metallic iron (1 mmol, marketed by Riedel de Haen, 99%), 140 mg of 1,3,5-benzene-tricarboxylic acid (0.6 mmol, 1,3,5-BTC, marketed by Aldrich, 99%) are dispersed in 5 ml of distilled water with 0.6 ml of 2M nitric acid (marketed by VWR, 50%) and 0.4 ml of 5M hydrofluoric acid (marketed by SDS, 50%). This is all placed in a 23 ml Teflon vessel inserted into a metallic PAAR type bomb and left for 6 days at 150° C. with a temperature increase gradient over 12 hours and a temperature decrease gradient over 24 hours. The solid is recovered by filtration.

The solid (200 mg) is then suspended in 100 ml of distilled water under reflux for 3 hrs with stirring to eliminate the trimesic acid remaining in the pores. The solid is then recovered by hot filtration.

Conditions for Synthesis without Hydrofluoric Acid:

0.27 g of $FeCl_3 \cdot 6H_2O$ (1 mmol, marketed by Alfa Aesar, 98%) and 140 mg (0.6 mmol) of 1,3,5-benzene-tricarboxylic acid (1,3,5-BTC, marketed by Aldrich, 99%) are dispersed in 5 ml of distilled water. This is all left in a 23 ml Teflon vessel inserted into a metallic PAAR type bomb for 3 days at 130° C. The solid is then filtered and washed with acetone.

The solid (200 mg) is then suspended in 100 ml of distilled water under reflux with stirring for 3 hrs to eliminate the trimesic acid remaining in the pores. The solid is then recovered by hot filtration.

Characteristic Data of the Iron Carboxylate MIL-100(Fe) Solid:

Analysis of the crystal structure of the MIL-100(Fe) solid by X-ray diffraction gives the X-RAY diffraction diagram shown in FIG. 1.

The characteristics of the crystal structure are as follows:
the space group is Fd-3m (No. 227).
the cell parameters are: a=73.1 Å, cell volume V=393000 Å$^3$.

Figure 2:
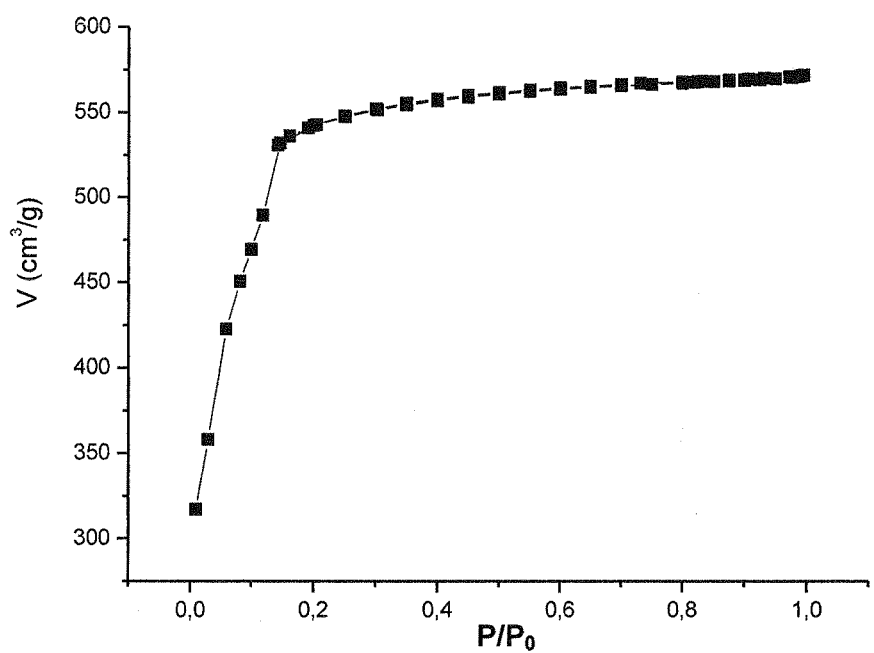
FIG. 2 shows a nitrogen adsorption isotherm at 77 K of the MIL-100(Fe) solid (Po=1 atm)

The nitrogen absorption isotherm at 77 K of the MIL-100 (Fe) solid (at pressure $P_0$=1 atm) is shown in FIG. 2. The specific surface area (Langmuir) of this solid is close to 2900 m$^2 \cdot$g$^{-1}$.

Figure 3:
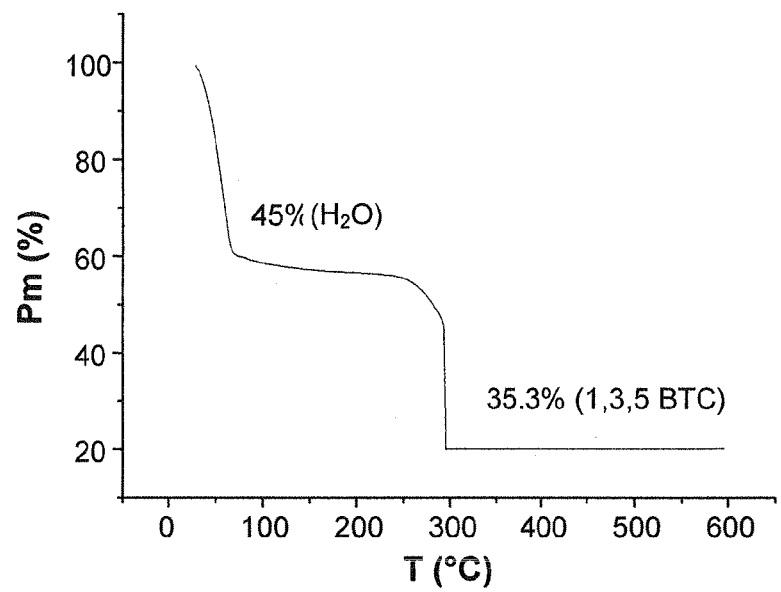
FIG. 3 shows a thermogravimetric analysis (in air, with a heating rate of 2° C./minute) of the compound MIL-100(Fe).

The curve resulting from thermogravimetric analysis of the compound MIL-100(Fe) is shown in FIG. 3. This diagram shows the weight loss Pm (in %) as a function of the temperature T (in ° C.).

The table below gives the elemental analysis of the MIL-100(Fe) solid or $Fe_3O[C_6H_3—(CO_2)_3]_2 \cdot X \cdot nH_2O$ in the case where X=F.

TABLE 1

| Element (weight %) | % Iron | % Carbon | % Fluorine |
|---|---|---|---|
| MIL-100 (Fe) | 13.8 | 23.5 | 1.3 | b) MIL-101(Fe) or $Fe_3O[C_6H_4—(CO_2)_2]_3 \cdot X \cdot nH_2O$ (X=F, Cl, OH)

Synthesis of MIL-101(Fe) Solid:

0.27 g (1 mmol) of $FeCl_3 \cdot 6H_2O$ and 249 mg (1.5 mmol) of 1,4-benzenedicarboxylic acid (1,4-BDC, marketed by Aldrich, 99%) are dispersed in 10 ml of dimethylformamide (DMF, marketed by Fluka, 98%). The mixture is left for 12 hours at 100° C. in a 23 ml Teflon vessel inserted into a metallic PAAR type bomb. The solid is then filtered and washed with acetone.

Figure 4:
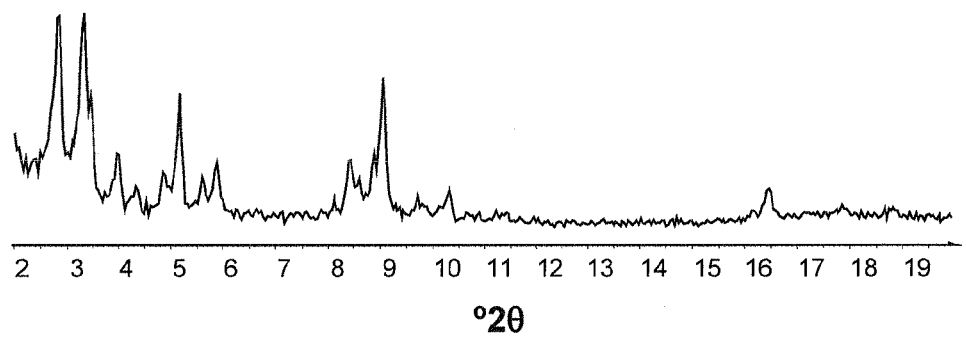
FIG. 4 shows the X-RAY diffraction diagram of the MIL-101(Fe) solid ($\lambda_{Cu}$=1.5406 Å)
Figure 5:
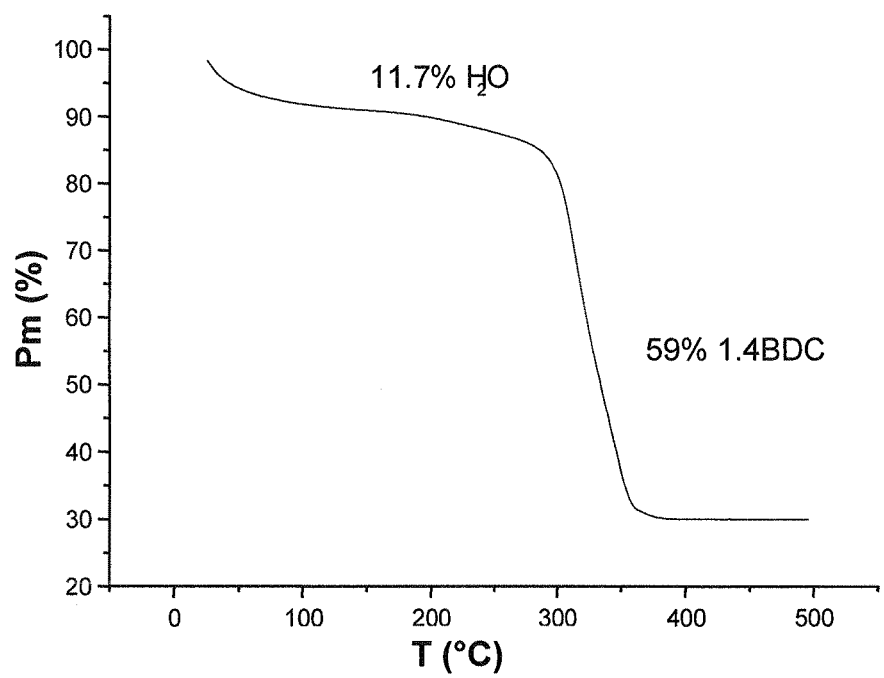
FIG. 5 shows a thermogravimetric analysis (in air, with a heating rate of 2° C./minute) of the compound MIL-101(Fe).

Characteristic Data of the MIL-101(Fe) Solid:
The X-RAY diffraction diagram of the solid MIL-101(Fe) is shown in FIG. 4.
The thermogravimetric analysis (in air, at a heating rate of 2° C./min) of the crude MIL-101(Fe) solid is shown in FIG. 5.
The characteristics of the crystal structure are as follows:
the space group is Fd-3m (No. 227).
the cell parameters of the MIL-101(Fe) solid at 298 K are:
a=89.0 Å, cell volume V=707000 Å$^3$.

The theoretical elemental composition of the dry solids (with X=F) is as follows: Fe 24.2%, C 41.4%, F 2.7%, H 1.7%.

c) MIL-102(Fe) or $Fe_6O_2X_2[C_{10}H_2—(CO_2)_4]_3 \cdot nH_2O$ (X=F, Cl . . . )

Synthesis of the Non-Fluorinated MIL-102(Fe) Solid:

270 mg (1 mmol) of $FeCl_3 \cdot 6H_2O$ (Alfa Aesar, 98%) and 268 mg (1 mmol) of 1,4,5,8-naphthalenetetracarboxylic acid are dispersed in 5 ml of distilled water. The mixture is left in a 23 ml Teflon vessel inserted into a metallic PAAR type bomb for 15 hours at 100° C. The solid is recovered by filtration.

Figure 6:
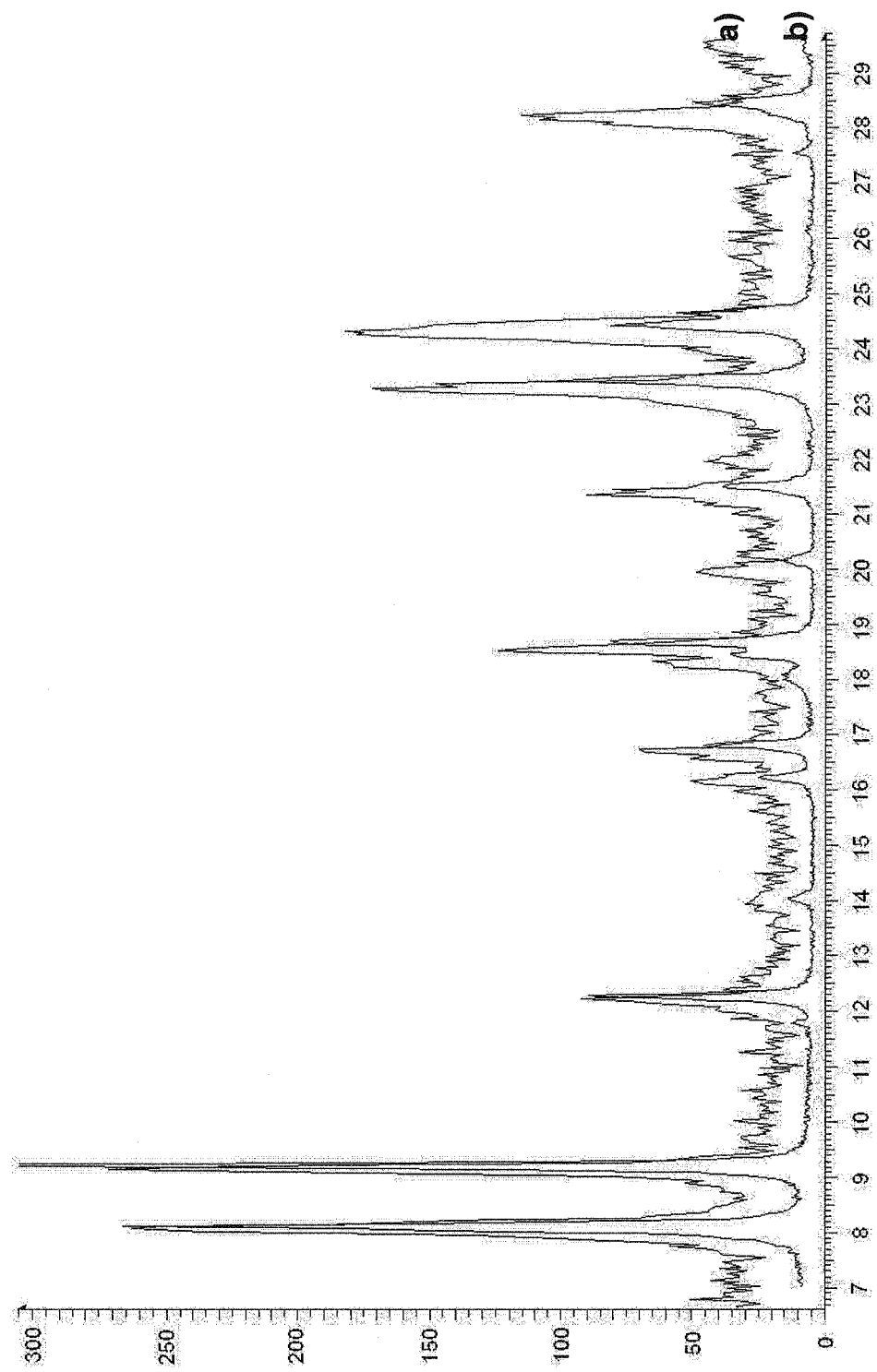
FIG. 6 shows X-RAY diffraction diagrams of the crude MIL-102(Fe) (curve (a)) and reference MIL-102(Cr) (curve (b)) solids
Figure 7:
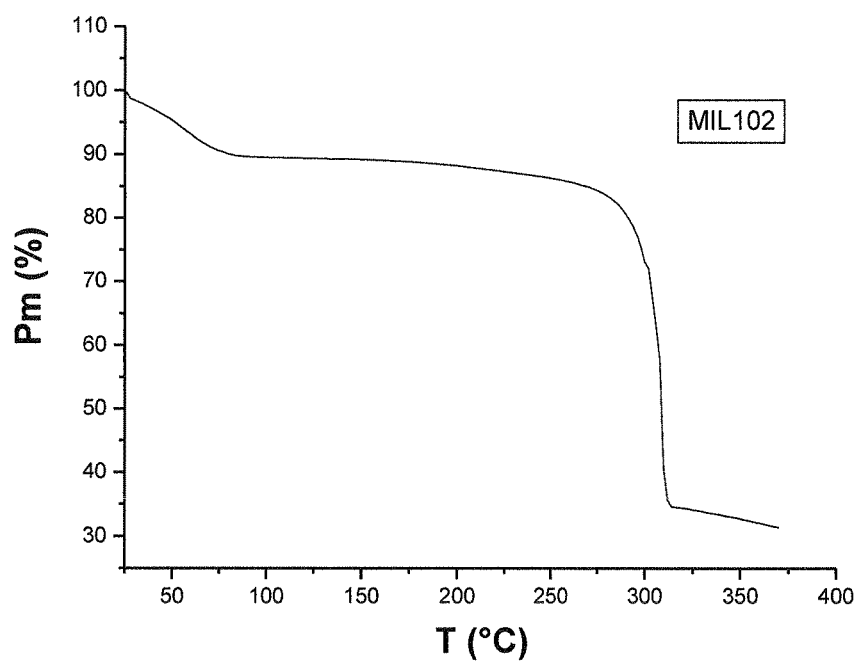
FIG. 7 shows a thermogravimetric analysis (in air) of the crude synthetic compound MIL-102 (Fe).

Characteristic Data of the MIL-102(Fe) Solid:
FIG. 6 shows the X-RAY diffraction diagram of the crude MIL-102(Fe) solid (curve (a)) and of the MIL-102(Cr) solid (curve (b)).
The thermogravimetric analysis (in air, at a heating rate of 2° C./min) of the crude MIL-102(Fe) solid is shown in FIG. 7.
This compound has a low specific surface area (Langmuir surface area: 101 m$^2$/g) in nitrogen at 77 K.

Preparation of the Fluorinated MIL-102(Fe) Solid 0.2 g of non-fluorinated MIL-102(Fe) solid of the formula $Fe_6O_2Cl_2[C_{10}H_4(CO_2)_4]_3 \cdot nH_2O$ obtained according to the method described above is contacted with 1 g of sodium fluoride NaF in 100 ml of distilled water. The mixture is left with stirring in a 125 ml Teflon vessel for 15 hours at ambient temperature. The solid is recovered by filtration and washed five times in distilled water to eliminate traces of NaF. Semi-quantitative analysis by EDX indicates a fluorine content of 0.17 fluorine atom per iron atom. The solid thus treated has an approximate formula of the type $Fe_6O_2F(OH)[C_{10}H_4(CO_2)_4]_3 \cdot nH_2O$.

d) MIL-88B-4CH$_3$ (Fe) or $Fe_3O[C_6 (CH_3)_4—(CO_2)_2]_3 \cdot X \cdot nH_2O$ (X=F, Cl, OH)

Synthesis of the MIL-88B-4CH$_3$ (Fe) Solid:

0.27 g (1 mmol) de $FeCl_3 \cdot 6H_2O$ (Alfa Aesar, 98%) and 222 mg (1 mmol) of 1,4-tetramethylterephthalic acid (Chem Service, 95%) are dispersed in 10 ml of DMF (Fluka, 98%) with 0.4 ml of 2M sodium hydroxide (Alfa Aesar, 98%). The mixture is left in a 23 ml Teflon vessel inserted into a metallic PAAR type bomb for 12 hours at 100° C. The solid is recovered by filtration.

200 mg of the solid are suspended in 100 ml of water with stirring at ambient temperature for 12 hours to eliminate the acid remaining in the pores. The solid is then recovered by filtration.

Figure 8:
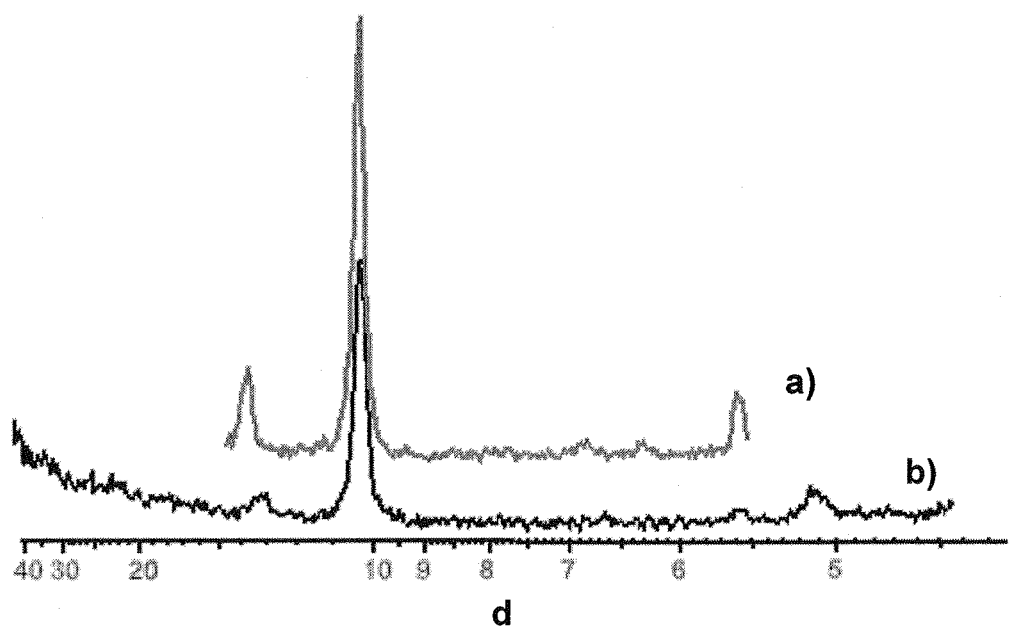
FIG. 8 shows X-RAY diffraction diagrams of the crude (curve (b) below) and hydrated (curve (a) above) MIL-88B-4CH$_3$(Fe) solid

Characteristic Data of the MIL-88B-4CH$_3$ (Fe) Solid:

FIG. 8 shows the X-RAY diffraction diagram of the crude solid (curve (b) below) and of the hydrated solid (curve (a) above).

Figure 9:
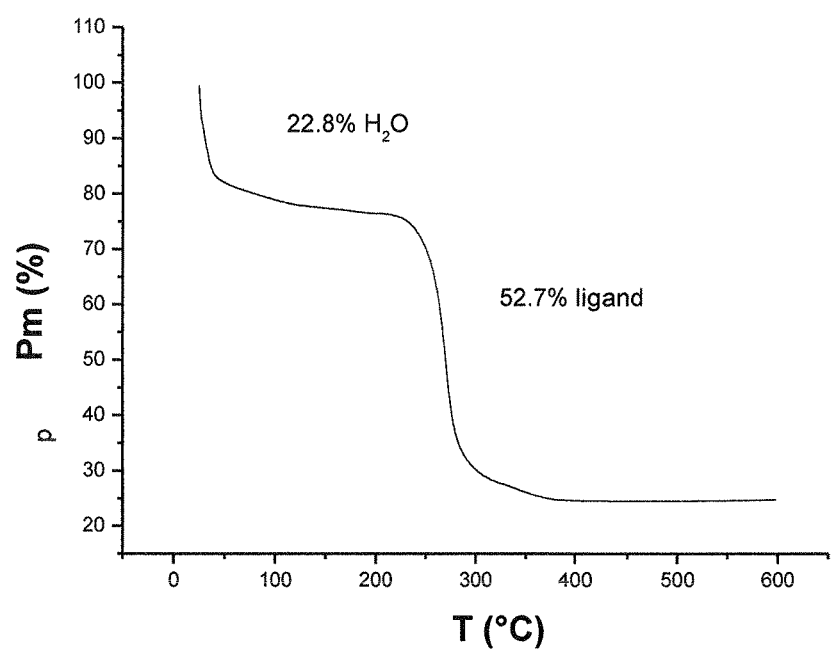
FIG. 9 shows a thermogravimetric analysis (in air, with a heating rate of 2° C./minute) of the hydrated compound MIL-88B-4CH$_3$(Fe).

The thermogravimetric analysis (in air, at a heating rate of 2° C./minute) of the hydrated MIL-88B-4CH$_3$(Fe) solid is shown in FIG. 9.

Figure 42:
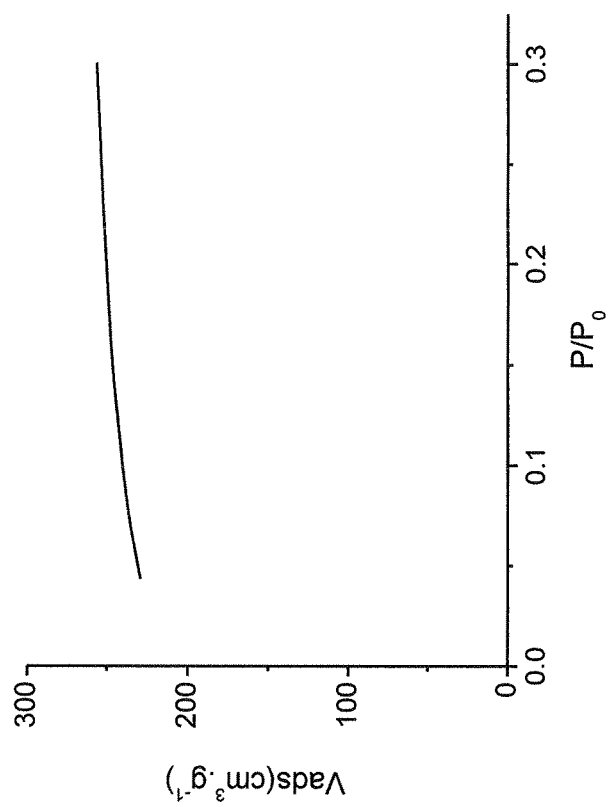
FIG. 42 shows a nitrogen adsorption isotherm at 77K of the MIL-88B_4CH$_3$ solid (degassed under primary vacuum at 100° C. for 16 hours). P0=1 atmosphere.

This compound presents an accessible surface area of the order of 1200 m$^2$/g (Langmuir model) to nitrogen at 77 K, since the dry structure has a pore size (6-7 Å) sufficient to incorporate nitrogen N$_2$ (FIG. 42).

d) MIL-88A(Fe) or Fe$_3$O[C$_2$H$_2$—(CO$_2$)$_2$]$_3$.X.nHO (X=F, Cl, OH)

Synthesis of the MIL-88A(Fe) Solid:

0.27 g (1 mmol) of FeCl$_3$.6H$_2$O (marketed by Alfa Aesar, 98%) and 116 mg (1 mmol) of fumaric acid (Aldrich, 99%) are dispersed in 5 ml of dimethylformamide (DMF, Fluka, 98%) with 0.4 ml of 2M NaOH (Alfa Aesar, 98%). The mixture is left in a 23 ml Teflon vessel inserted into a metallic PAAR type bomb for 12 hours at 100° C. The solid is then filtered and washed with acetone.

The solid (200 mg) is then suspended in 100 ml of distilled water with stirring for 12 hrs to eliminate the solvent remaining in the pores. The solid is then recovered by filtration.

Characteristic Data of the MIL-88A(Fe) Solid:

Analysis of the crystal structure of the solid gives the characteristics listed in the following table:

TABLE 2

Cell parameters of the dry and hydrated MIL-88A solid.

| Phase | a (Å) | c (Å) | Cell volume (Å$^3$) | Pore size (Å) | Space group |
|---|---|---|---|---|---|
| MIL-88A dry | 9.25 | 15.30 | 1135 | — | P-62c |
| MIL-88A hydrate (H$_2$O) | 13.9 | 12.66 | 2110 | 6-7 | P-62c |

A thermogravimetric analysis of the hydrated MIL-88A compound (in air, at a heating rate of 2° C./minute) was performed (results not presented).

The compound MIL-88A does not present an accessible surface area (greater than 20 m$^2$/g) to nitrogen at 77 K since the dry structure has a pore size too small to incorporate nitrogen N$_2$.

The elemental analysis is given in the table below:

TABLE 3

| Element (weight %) | % Iron | % Carbon |
|---|---|---|
| MIL-88A (crude) | 21.8 | 24.0 | e) MIL-88B(Fe) or Fe$_3$O[C$_6$H$_4$—(CO$_2$)$_2$]$_3$.X.nH$_2$O (X=F, Cl, OH)

Synthesis of the MIL-88B(Fe) Solid:

0.27 g (1 mmol) of FeCl$_3$.6H$_2$O (Alfa Aesar, 98%) and 116 mg (1 mmol) of 1,4-benzenedicarboxylic acid (Aldrich, 98%) are dispersed in 5 ml of dimethylformamide (DMF, Fluka, 98%) with 0.4 ml of 2M sodium hydroxide (Alfa Aesar, 98%). The mixture is left in a 23 ml Teflon vessel inserted into a metallic PAAR type bomb for 12 hours at 100° C. The solid is then filtered off and washed with acetone.

200 mg of the solid is suspended in 100 ml of distilled water with stirring for 12 hrs to eliminate the solvent remaining in the pores. The solid is then recovered by filtration.

Characteristic Data of the MIL-88B(Fe) Solid:

Analysis of the crystal structure of the solid gives the characteristics listed in the following table:

TABLE 4

Cell parameters of the dry and hydrated MIL-88B solid.

| Phase | a (Å) | c (Å) | Cell volume (Å$^3$) | Pore size (Å) | Space group |
|---|---|---|---|---|---|
| MIL-88B dry | 9.6 | 19.1 | 1500 | <3 | P-62c |
| MIL-88B hydrate (EtOH) | 15.7 | 14.0 | 3100 | 9 | P-62c |

A thermogravimetric analysis of the hydrated compound MIL-88B (in air, at a heating rate of 2° C./minute) was performed (results not presented).

The compound MIL-88B does not present an accessible surface area (greater than 20 m$^2$/g) to nitrogen at 77 K, since the dry structure has a pore size too small to incorporate nitrogen N$_2$.

f) MIL-89(Fe) or Fe$_3$O[C$_4$H$_4$—(CO$_2$)$_2$]$_3$.X.nH$_2$O (X=F, Cl, OH)

Synthesis of the MIL-89(Fe) Solid:

172 mg (1 mmol) of iron acetate (prepared according to the synthesis described by Dziobkowski et al., *Inorg. Chem.* 1982, 20, 671 [ref. 29]) and 150 mg (1 mmol) of muconic acid (Fluka, 97%) are dispersed in 10 ml of methanol (Fluka, 98%) with 0.35 ml of 2M sodium hydroxide (Alfa Aesar, 98%). The mixture is left in a 23 ml Teflon vessel inserted into a metallic PAAR type bomb for 3 days at 100° C. The solid is then filtered off and washed with acetone.

200 mg of the solid is suspended in 100 ml of distilled water with stirring for 12 hrs to eliminate the solvent remaining in the pores. The solid is then recovered by filtration.

Characteristic Data of the MIL-89(Fe) Solid:

X-ray diffraction analysis of the dry MIL-89(Fe) solid, the MIL-89(Fe) solid solvated with DMF and of the hydrated MIL-89(Fe) solid was performed (results not presented).

The compound MIL-89(Fe) does not present an accessible surface area (greater than 20 m$^2$/g) to nitrogen at 77 K, since the dry structure has a pore size too small to incorporate nitrogen N$_2$.

g) MIL-88C(Fe) or $Fe_3O[C_{10}H_6—(CO_2)_2]_3.X.nH_2O$ (X=F, Cl, OH)

Preparation of Iron Acetate(III)

Iron acetate(III), used in the examples below for the synthesis of MOF materials according to the invention, is synthesized by following method. Reference to this synthesis can be found in the publication by Dziobkowski et al., *Inorg. Chem.*, 1982, 21, 671 [ref. 14].

6.72 g of powdered metallic iron (Riedel-de Haen, 99%), 64 ml of deionized water and 33.6 ml of 70% perchloric acid in water (Riedel-de Haen) are mixed with magnetic stirring and heated at 50° C. for 3 hours. The heating is stopped, and then the solution is stirred for hours. The residual metallic iron is eliminated by decantation followed by transfer into another vessel. 20.6 ml of aqueous hydrogen peroxide solution (marketed by Alfa Aesar, 35%) is added dropwise with stirring, the whole being maintained at 0° C. in an ice-bath. 19.7 g of sodium acetate (Aldrich, 99%) is added to the blue solution with stirring while maintaining the solution at 0-5° C. The solution is allowed to evaporate for 3 days under the hood in a glass crystallizer (Volume=0.5 l). Finally the red crystals of iron acetate are recovered by filtration and washed very rapidly with deionized ice water. The crystals are then dried in air.

Synthesis of the MIL-88C(Fe) Solid:

172 mg (1 mmol) of iron acetate (synthesized by the above method) and 140 mg (1 mmol) of 2,6-naphthalene-dicarboxylic acid (Aldrich, 95%) are dispersed in 5 ml of dimethylformamide (DMF, Fluka, 98%). The mixture is left in a 23 ml Teflon vessel inserted into a metallic PAAR type bomb for 3 days at 150° C. with an increase gradient over 12 hours and a decrease gradient over 24 hours. The solid is recovered by filtration. The solid is dried at 150° C. in air for 15 hours.

Characteristic Data of the MIL-88C(Fe) Solid:

Analysis of the crystal structure of the solid gives the characteristics listed in the following table:

TABLE 5

Cell parameters of dry and solvated MIL-88C solid.

| Phase | a (Å) | c (Å) | Cell volume (Å$^3$) | Pore size (Å) | Space group |
|---|---|---|---|---|---|
| MIL-88C dry | 9.9 | 23.8 | 2020 | 3 | P-62c |
| MIL-88C solvated (Pyridine) | 18.7 | 18.8 | 5600 | 13 | P-62c |

A thermogravimetric analysis of the crude synthetic compound MIL-88C (in air, at a heating rate of 2° C./minute) was performed (results not presented).

This compound does not present an accessible surface area (greater than 20 m$^2$/g) to nitrogen at 77 K, since the dry structure has a pore size too small to incorporate nitrogen N$_2$.

h) MIL-88D(Fe) or $Fe_3O[C_{12}H_8—(CO_2)_2]_3.X.nH_2O$ (X=F, Cl, OH)

Synthesis of the MIL-88D(Fe) Solid:

270 mg (1 mmol) of FeCl$_3$.6H$_2$O (Alfa Aesar, 98%) and 140 mg (0.6 mmol) of 4,4'-biphenyldicarboxylic acid (Fluka, 95%) are dispersed in 5 ml of dimethylformamide (DMF, Aldrich, 99%). The mixture is left in a 23 ml Teflon vessel inserted into a metallic PAAR type bomb for 12 hours at 100° C. with an increase gradient over one hour and a decrease gradient over one hour. The solid is recovered by filtration.

The solid is then dried at 150° C. in air for 15 hours.

Characteristic Data of the MIL-88D(Fe) Solid:

Analysis of the crystal structure of the solid gives the characteristics listed in the following table:

TABLE 6

Cell parameters of the MIL-88D solid, dry and solvated (pyridine).

| Phase | a (Å) | c (Å) | Cell volume (Å$^3$) | Pore size (Å) | Space group |
|---|---|---|---|---|---|
| MIL-88D dry | 10.1 | 27.8 | 2480 | <3 | P-62c |
| MIL-88D solvated (pyridine) | 20.5 | 22.4 | 8100 | 16 | P-62c |

X-RAY diffraction analysis of the crude and hydrated MIL-88D solid was performed (results not presented).

Thermogravimetric analysis of the hydrated compound MIL-88D(Fe) (in air, at a heating rate of 2° C./minute) was performed (results not presented).

This compound does not present an accessible surface area (greater than 20 m$^2$/g) to nitrogen at 77 K, since the dry structure has a pore size too small to incorporate nitrogen N$_2$.

i) MIL-88B-NO$_2$ (Fe) or $Fe_3O[C_6H_3NO_2—(CO_2)_2]_3.X.nH_2O$ (X=F, Cl, OH)

Synthesis of the MIL-88B-NO$_2$(Fe) Solid:

0.27 g (1 mmol) of FeCl$_3$.6H$_2$O (Alfa Aesar, 98%) and 211 mg (1 mmol) of 2-nitroterephthalic acid (Acros, 99%) are dispersed in 5 ml of distilled water. The mixture is left in a 23 ml Teflon vessel inserted into a metallic PAAR type bomb for 12 hours at 100° C. The solid is recovered by filtration.

200 mg of the solid are suspended in 10 ml of absolute ethanol in a 23 ml Teflon vessel inserted into a metallic PAAR type bomb for 12 hours at 100° C. to eliminate the acid remaining in the pores. The solid is then recovered by filtration and dried at 100° C.

Characteristic Data of the MIL-88B-NO$_2$(Fe) Solid:

X-RAY diffraction analysis of the crude and hydrated MIL-88B-NO$_2$ solid was performed (results not presented).

Thermogravimetric analysis (in air, at a heating rate of 2° C./minute) of the compound MIL-88B-NO$_2$(Fe), after washing and drying was performed (results not presented).

This compound does not present an accessible surface area (greater than 20 m$^2$/g) to nitrogen at 77 K, since the dry structure has a pore size too small to incorporate nitrogen N$_2$.

The elemental analysis is given in the table below:

TABLE 7

| Element (weight %) | % Iron | % Carbon | % Nitrogen |
|---|---|---|---|
| MIL-88B-NO$_2$ | 20.6 | 39.3 | 4.6 | j) MIL-88B-2OH(Fe) or $Fe_3O[C_6H_2 (OH)_2—(CO_2)_2]_3.X.nH_2O$ (XF, Cl, OH)

Synthesis of the MIL-88B-2OH(Fe) Solid:

354 mg (1 mmol) of Fe(ClO$_4$)$_3$.xH$_2$O (Aldrich, 99%) and 198 mg (1 mmol) of 2,5-dihydroxoterephthalic acid (obtained by hydrolysis of the corresponding diethyl ester, Aldrich 97%) are dispersed in 5 ml of DMF (Fluka, 98%). The mixture is left in a 23 ml Teflon vessel inserted into a metallic PAAR type bomb for 12 hours at 85° C. The solid is recovered by filtration.

To eliminate the acid remaining in the pores, the product is calcined at 150° C. under vacuum for 15 hours.

Characteristic Data of the MIL-88B-2OH(Fe) solid:

X-RAY diffraction analysis of the crude, hydrated and vacuum-dried solid MIL-88B-2OH was performed (results not presented).

Thermogravimetric analysis (in air, at a heating rate of 2° C./minute) of the compound MIL-88B-2OH(Fe), after washing and drying, was performed (results not presented).

This compound does not present an accessible surface area (greater than 20 m$^2$/g) to nitrogen at 77 K, since the dry structure has a pore size too small to incorporate nitrogen $N_2$.

The elemental analysis is given in the table below:

TABLE 8

| Element (weight %) | % Iron | % Carbon |
|---|---|---|
| MIL-88B-2OH | 15.4 | 36.5 | k) MIL-88B-NH$_2$ (Fe) or Fe$_3$O[C$_6$H$_3$NH$_2$—(CO$_2$)$_2$]$_3$.X.nH$_2$O (X=F, Cl, OH)

Synthesis of the MIL-88B-NH$_2$(Fe) Solid:

0.27 g (1 mmol) of FeCl$_3$.6H$_2$O (Alfa Aesar, 98%) and 180 mg (1 mmol) of 2-aminoterephthalic acid (Fluka, 98%) are dispersed in 5 ml of pure ethanol. The mixture is left in a 23 ml Teflon vessel inserted into a metallic PAAR type bomb for 3 days at 100° C. The solid is recovered by filtration.

To eliminate the acid remaining in the pores, the solid is calcined at 200° C. for 2 days.

Characteristic Data of the MIL-88B-NH$_2$(Fe) Solid:

X-RAY diffraction analysis of the crude and vacuum-dried MIL-88B-NH$_2$ solid was performed (results not presented).

Thermogravimetric analysis (in air, at a heating rate of 2° C./minute) of the hydrated MIL-88B-NH$_2$(Fe) solid was performed (results not presented).

This compound does not present an accessible surface area (greater than 20 m$^2$/g) to nitrogen at 77 K, since the dry structure has a pore size too small to incorporate nitrogen $N_2$.

l) MIL-88B-CH$_3$ or Fe$_3$O[C$_6$H$_3$CH$_3$—(CO$_2$)$_2$]$_3$.X.nH$_2$O (X=F, C OH)

Synthesis of the MIL-88B-CH$_3$(Fe) Solid:

354 mg (1 mmol) of Fe(ClO$_4$)$_3$.xH$_2$O (Aldrich, 99%) and 180 mg (1 mmol) of 2-methylterephthalic acid (prepared according to the synthesis described by Anzalone et al., *J. Org. Chem.* 1985, 50, 2128 [ref. 30]) are dispersed in 5 ml of methanol (Fluka, 99%). The mixture is left in a 23 ml Teflon vessel inserted into a metallic PAAR type bomb for 3 days at 100° C. The solid is recovered by filtration.

200 mg of the solid are suspended in 10 ml of DMF with stirring at ambient temperature to replace the acid present in the pores by DMF, then the DMF is eliminated by heating at 150° C. under vacuum for 12 hours.

Characteristic Data of the MIL-88B-CH$_3$ (Fe) Solid:

X-RAY diffraction analysis of the crude, hydrated and DMF-solvated MIL-88B-CH$_3$ solid was performed (results not presented).

This compound does not present an accessible surface area (greater than 20 m$^2$/g) to nitrogen at 77 K, since the dry structure has a pore size too small to incorporate nitrogen $N_2$.

m) MIL-88B-Cl (Fe) or Fe$_3$O[C$_6$H$_3$Cl—CO$_2$)$_2$].X.nH$_2$O (X=F, Cl, OH)

Synthesis of the MIL-88B-Cl(Fe) Solid:

354 mg (1 mmol) of Fe(ClO$_4$)$_3$.xH$_2$O (Aldrich, 99%) and 200 mg (1 mmol) of 2-chloroterephthalic acid (synthesized according to synthesis A from example 2) are dispersed in 10 ml of DMF with 0.1 ml of 5M HF (SDS, 50%) and 0.1 ml of 1M HCl (Aldrich, 37%). The mixture is left in a 23 ml Teflon vessel inserted into a metallic PAAR type bomb for 5 days at 100° C. The solid is recovered by filtration.

The solid obtained is calcined at 150° C. under vacuum.

Characteristic Data of the MIL-88B-Cl (Fe) Solid:

X-RAY diffraction analysis of the crude, hydrated and DMF-solvated MIL-88B-Cl solid was performed (results not presented).

Thermogravimetric analysis (in air, at a heating rate of 2° C./minute) of the hydrated MIL-88B-Cl(Fe) solid was performed (results not presented).

This compound does not present an accessible surface area (greater than 20 m$^2$/g) to nitrogen at 77 K, since the dry structure has a pore size too small to incorporate nitrogen $N_2$.

n) MIL-88B-4F (Fe) or Fe$_3$O[C$_6$F$_4$—CO$_2$)$_2$]$_3$.X.nH$_2$O (X=F, Cl, OH)

Synthesis of the MIL-88B-4F (Fe) Solid:

270 mg (1 mmol) of FeCl$_3$.6H$_2$O (Alfa Aesar, 98%) and 230 mg (1 mmol) of tetrafluoroterephthalic acid (Aldrich, 98%) are dispersed in 10 ml of distilled water. The mixture is left in a 23 ml Teflon vessel inserted into a metallic PAAR type bomb for 12 hours at 85° C. The solid is recovered by filtration.

200 mg of the solid are suspended in 20 ml of water with stirring at ambient temperature for 2 hours to eliminate the acid remaining in the pores. The solid is then recovered by filtration.

Characteristic Data of the MIL-88B-4F (Fe) Solid:

X-RAY diffraction analysis of the crude solid, the hydrated solid and the ethanol-solvated solid was performed (results not presented).

Thermogravimetric analysis (in air, at a heating rate of 2° C./minute) of the hydrated MIL-88B-4F(Fe) solid was performed (results not presented).

This compound does not present an accessible surface area (greater than 20 m$^2$/g) to nitrogen at 77 K, since the dry structure has a pore size too small to incorporate nitrogen $N_2$.

o) MIL-88B-Br (Fe) or Fe$_3$O[C$_6$H$_3$Br—(CO$_2$)$_2$]$_3$.X.nH$_2$O (X=F, Cl, OH)

Synthesis of the MIL-88B-Br (Fe) Solid:

270 mg (1 mmol) of FeCl$_3$.6H$_2$O (Alfa Aesar, 98%) and 250 mg (1 mmol) of 2-bromoterephthalic acid (Fluka, 95%) are dispersed in 10 ml of DMF (Fluka, 98%) with 0.2 ml of 5M hydrofluoric acid (SDS, 50%). The mixture is left in a 23 ml Teflon vessel inserted into a metallic PAAR type bomb for 12 hours at 150° C. The solid is recovered by filtration.

To eliminate the acid remaining in the pores, the solid is calcined at 150° C. under vacuum for 15 hours.

Characteristic Data of the MIL-88B-Br (Fe) solid:

X-RAY diffraction analysis of the crude solid and the hydrated solid was performed (results not presented).

Thermogravimetric analysis (in air, at a heating rate of 2° C./minute) of the hydrated MIL-88B-Br(Fe) solid was performed (results not presented).

This compound does not present an accessible surface area (greater than 20 m²/g) to nitrogen at 77 K, since the dry structure has a pore size too small to incorporate nitrogen $N_2$.

p) MIL-88E (Fe) or $Fe_3O[C_4H_3N_2-(CO_2)_2]_3 \cdot X \cdot nH_2O$ (X=F, Cl, OH)

Synthesis of the MIL-88E (Fe) Solid:

270 mg (1 mmol) of $FeCl_3 \cdot 6H_2O$ (Alfa Aesar, 98%) and 204 mg (1 mmol) of 2,5-pyrazinedicarboxylic acid (Aldrich, 98%) are dispersed in 5 ml of DMF (Fluka, 98%) with 0.05 ml of 5M HF (SDS, 50%). The mixture is left in a 23 ml Teflon vessel inserted into a metallic PAAR type bomb for 3 days at 100° C. The solid is recovered by filtration.

Characteristic Data of the MIL-88E (Fe) Solid:

X-RAY diffraction analysis of the crude synthetic MIL-88E(Fe) solid was performed (results not presented).

This compound does not present an accessible surface area (greater than 20 m²/g) to nitrogen at 77 K, since the dry structure has a pore size too small to incorporate nitrogen $N_2$.

q) MIL-88F (Thio) (Fe) or $Fe_3O[C_4H_2S-(CO_2)_2]_3 \cdot X \cdot nH_2O$ (X=F, Cl, OH)

Synthesis of the MIL-88F(Fe) Solid:

354 mg (1 mmol) of $Fe(ClO_4)_3 \cdot xH_2O$ (Aldrich, 99%) and 258 mg (1 mmol) of 2,5-thiophenedicarboxylic acid (Aldrich, 99%) are dispersed in 2.5 ml of DMF (Fluka, 98%) with 0.1 ml of 5M HF (SDS, 50%). The mixture is left in a 23 ml Teflon vessel inserted into a metallic PAAR type bomb for 3 days at 100° C. The solid is recovered by filtration.

200 mg of the solid are suspended in 100 ml of water with stirring at ambient temperature for 12 hours to eliminate the acid remaining in the pores. The solid is then recovered by filtration.

Characteristic Data of the MIL-88F(Fe) Solid:

X-RAY diffraction analysis of the crude solid and the hydrated solid was performed (results not presented).

Thermogravimetric analysis (in air, at a heating rate of 2° C./minute) of the hydrated MIL-88F(Fe) solid was performed (results not presented).

This compound does not present an accessible surface area (greater than 20 m²/g) to nitrogen at 77 K, since the dry structure has a pore size too small to incorporate nitrogen $N_2$.

r) MIL-88D-4CH$_3$ (Fe) or $Fe_3O[C_{12}H_4(CH_3)_4-(CO_2)_2]_3 \cdot X \cdot nH_2O$ (X=F, Cl, OH)

Synthesis of the MIL-88D-4CH$_3$(Fe) Solid:

354 mg (1 mmol) of $Fe(ClO_4)_3 \cdot xH_2O$ (Aldrich, 99%) and 298 mg (1 mmol) of tetramethylbiphenyl-4,4'-dicarboxylic acid (synthesized according to synthesis B described in example 2) are dispersed in 5 ml of DMF (Fluka, 98%) with 0.2 ml of 2M sodium hydroxide (Alfa Aesar, 98%). The mixture is left in a 23 ml Teflon vessel inserted into a metallic PAAR type bomb for 12 hours at 100° C. The solid is recovered by filtration.

200 mg of the solid are suspended in 10 ml of DMF with stirring at ambient temperature for 2 hours to exchange the acid remaining in the pores. The solid is then recovered by filtration, and the DMF present in the pores eliminated by calcination at 150° C. under vacuum for 15 hours.

Characteristic Data of the MIL-88D-4CH$_3$(Fe)Solid:

X-RAY diffraction analysis of the crude solid and the hydrated solid was performed (results not presented).

Thermogravimetric analysis (in air, at a heating rate of 2° C./minute) of the hydrated MIL-88D-4CH$_3$(Fe) solid was performed (results not presented).

This compound does not present an accessible surface area (greater than 20 m²/g) to nitrogen at 77 K, since the dry structure has a pore size too small to incorporate nitrogen $N_2$.

s) MIL-88D-2CH$_3$(Fe) or $Fe_3O[C_{12}H_6(CH_3)_2-(CO_2)_2]_3 \cdot X \cdot nH_2O$ (X=F, Cl, OH)

Synthesis of the MIL-88D-2CH$_3$(Fe) Solid:

270 mg (1 mmol) of $FeCl_3 \cdot 6H_2O$ (Alfa Aesar, 98%) and 268 mg (1 mmol) of dimethylbiphenyl-4,4'-dicarboxylic acid (synthesized according to synthesis C described in example 2) are dispersed in 5 ml of DMF (Fluka, 98%) with 0.25 ml of 5M HF (SDS, 50%). The mixture is left in a 23 ml Teflon vessel inserted into a metallic PAAR type bomb for 12 hours at 150° C. The solid is recovered by filtration.

To eliminate the acid remaining in the pores, the solid is calcined at 150° C. under vacuum for 15 hours.

Characteristic Data of the MIL-88D-2CH$_3$(Fe) Solid:

X-RAY diffraction analysis of the crude solid, of the hydrated MIL-88D-2CH$_3$(H$_2$O) solid and the MIL-88D-2CH$_3$ solid suspended in water (H$_2$O droplet) was performed (results not presented).

Thermogravimetric analysis (in air, at a heating rate of 2° C./minute) of the crude MIL-88D-2CH$_3$(Fe) solid was performed (results not presented).

This compound does not present an accessible surface area (greater than 20 m²/g) to nitrogen at 77 K, since the dry structure has a pore size too small to incorporate nitrogen $N_2$.

t) MIL-88G (AzBz) (Fe) or $Fe_3O[C_{12}H_8N_2-(CO_2)_2]_3 \cdot X \cdot nH_2O$ (X=F, Cl, OH)

Synthesis of the MIL-88G(Fe) Solid:

118 mg (0.33 mmol) of $Fe(ClO_4)_3 \cdot xH_2O$ (Aldrich, 99%) and 90 mg (0.33 mmol) of 4,4'-azobenzenedicarboxylic acid (synthesized according to the method described by Ameerunisha et al., *J. Chem. Soc. Perkin Trans.* 2 1995, 1679 [ref. 31]) are dispersed in 15 ml of DMF (Fluka, 98%). The mixture is left in a 23 ml Teflon vessel inserted into a metallic PAAR type bomb for 3 days at 150° C. The solid is recovered by filtration.

200 mg of the solid are suspended in 10 ml of DMF with stirring at ambient temperature for 2 hours to exchange the acid remaining in the pores. The solid is then recovered by filtration and the DMF remaining in the pores eliminated by calcination at 150° C. under vacuum for 15 hours.

Characteristic Data of the MIL-88G(Fe) Solid:

X-RAY diffraction analysis of the crude MIL-88G solid, the DMF-solvated solid and the pyridine-solvated solid was performed (results not presented).

Thermogravimetric analysis (in air, at a heating rate of 2° C./minute) of the crude MIL-88G(Fe) solid was performed (results not presented).

This compound does not present an accessible surface area (greater than 20 m²/g) to nitrogen at 77 K, since the dry structure has a pore size too small to incorporate nitrogen $N_2$.

u) MIL-88G-2Cl (AzBz-2Cl) (Fe) or $Fe_3O[C_{12}H_6N_2Cl_2-(CO_2)_2]_3 \cdot X \cdot nH_2O$ (X=F, Cl, OH)

Synthesis of the MIL-88G-2Cl(Fe) Solid:

177 mg (0.5 mmol) of $Fe(ClO_4)_3 \cdot xH_2O$ (Aldrich, 99%) and 169 mg (0.5 mmol) of dichloro-4,4'-azobenzene-dicarboxylic acid (synthesized according to synthesis D described in example 2) are dispersed in 15 ml of DMF (Fluka, 98%). The mixture is left in a 23 ml Teflon vessel inserted into a metallic PAAR type bomb for 12 hours at 150° C. The solid is recovered by filtration.

200 mg of the solid are suspended in 10 ml of DMF with stirring at ambient temperature for 2 hours to exchange the acid remaining in the pores. The solid is then recovered by filtration, and the DMF remaining in the pores is eliminated by calcination at 150° C. under vacuum for 15 hours.

Characteristic Data of the MIL-88G-2Cl(Fe) Solid:

X-RAY diffraction analysis of the crude MIL-88G-201 solid and of the dry MIL-88G-2Cl solid was performed (results not presented).

Thermogravimetric analysis (in air, at a heating rate of 2° C./minute) of the crude MIL-88G-2Cl(Fe) solid was performed (results not presented).

This compound does not present an accessible surface area (greater than 20 m$^2$/g) to nitrogen at 77 K, since the dry structure has a pore size too small to incorporate nitrogen $N_2$.

v) MIL-126(Fe) or $Fe_6O_2X_2[C_{10}H_2—(CO_2)_4]_3.nH_2O$ (X=F, Cl . . . )

Synthesis of the MIL-126(Fe) Solid:

270 mg (1 mmol) of $FeCl_3.6H_2O$ (Alfa Aesar, 98%) and 140 mg (0.6 mmol) of 4,4'-biphenyldicarboxylic acid (Fluka, 95%) are dispersed in 5 ml of dimethylformamide (DMF, Aldrich, 99%). The mixture is left in a 23 ml Teflon vessel inserted into a metallic PAAR type bomb for 12 hours at 150° C. with an increase gradient over 1 hour and a decrease gradient over 1 hour. The solid is recovered by filtration.

The solid is then dried at 150° C. under primary vacuum for 15 hours.

Figure 43A:
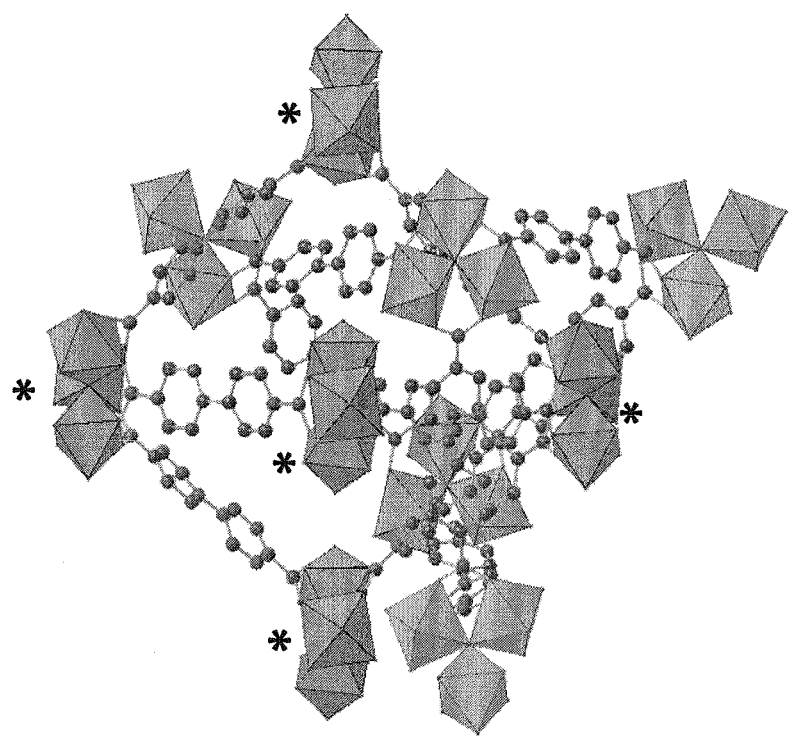
FIG. 43A shows the crystallographic structure of MIL-126 (Fe). The FeO$_6$ polyhedra are shown in orange or in green, each color representing an MIL-88D network. The carbon atoms are in black.

Characteristic Data of the MIL-126(Fe) Solid:

The crystallographic structure of the MIL-126(Fe) solid is an interpenetrated form of the MIL-88D(Fe) structure, that is to say that it has two entangled crystal sub-frameworks of the MIL-88D type (FIG. 43).

Analysis of the crystal structure of the solid gives the characteristics listed in the following table:

TABLE 9

Cell parameters of the dry and solvated (dimethylformamide) MIL-126 solid.

| Phase | a (Å) | c (Å) | Cell volume (Å$^3$) | Pore size (Å) | Space group |
|---|---|---|---|---|---|
| MIL-126 dry | 19.5 | 35.3 | 13500 | A to 10 | P 41 21 2 |
| MIL-126 solvated (DMF) | 21.8 | 36.1 | 17200 | 5 to 11 | P 41 21 2 |

The complete crystallographic data is given in FIGS. 43B-43H.

Figure 44:
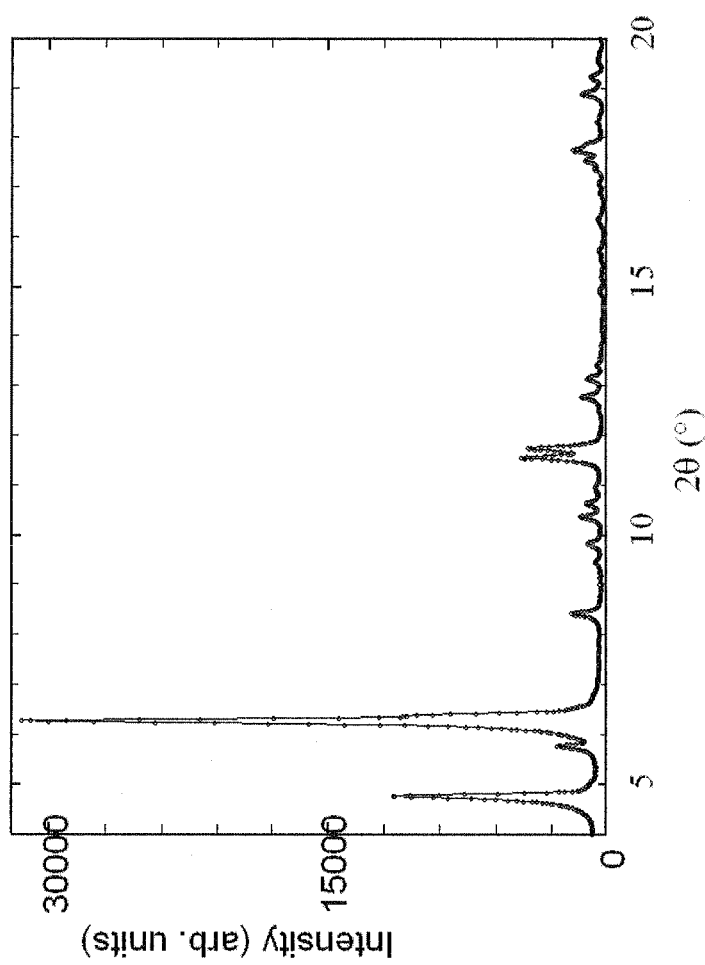
FIG. 44 shows an Xray diffraction diagram of MIL-126 (Fe) ($\lambda_{Cu}$=1.5406 Å)

FIG. 44 shows the X-RAY diffraction diagram of the crude MIL-126 solid.

Figure 45:
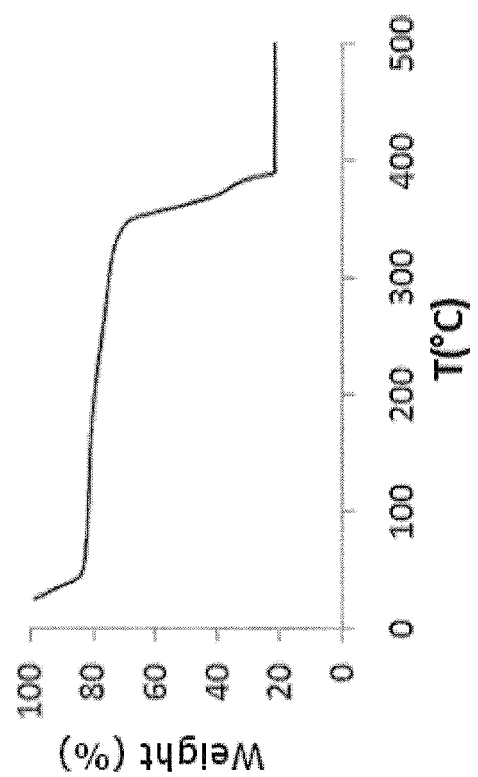
FIG. 45 shows a thermogravimetric analysis of MIL-126 (Fe) in air (heating rate of 2° C./min).

The results of the thermogravimetric analysis of the crude synthetic MIL-126(Fe) compound (in air, at a heating rate of 2° C./minute) are shown in FIG. 45 (weight loss Pm as a function of temperature T).

Figure 46:
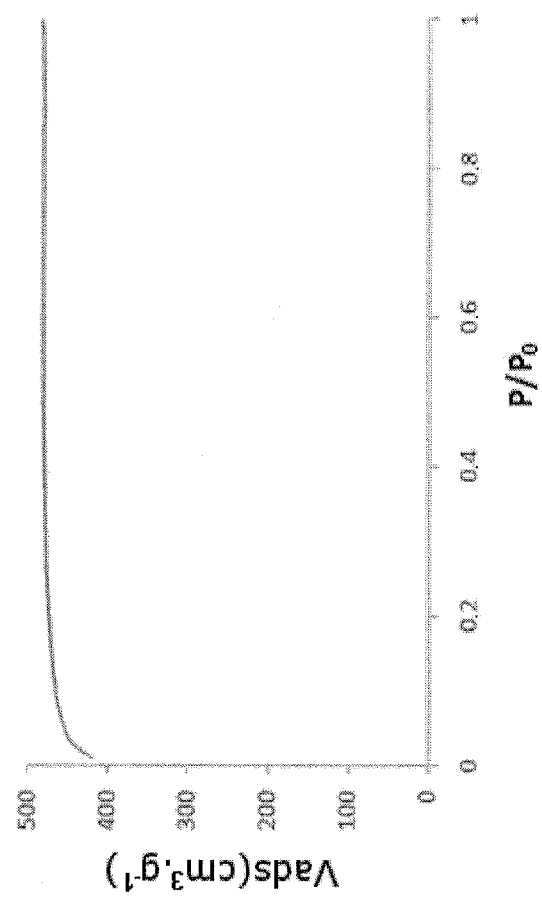
FIG. 46 shows nitrogen adsorption isotherms of MIL-126 (Fe) (P$_0$=1 atmosphere).

This compound presents a substantial accessible surface area (Langmuir) (greater than 2100 m$^2$/g) to nitrogen at 77 K (FIG. 46).

w) MIL-127(Fe) or $Fe_6O_2[C_{12}H_6N_2—(CO_2)_4]_3.X_2.nH_2O$ (X=F, Cl, OH)

In this example the phase isotypic with that of indium published by Y. Liu et al, Angew. Chem. Int. Ed. 2007, 46, 3278-3283 [ref 51] is created.

Synthesis of the MIL-127(Fe) Solid:

The solid is recovered by filtration and vacuum-dried at 90° C.

118 mg (0.3 mmol) of Fe(ClO4)3.nH2O (Aldrich, 98%) and 119 mg (0.6 mmol) of 3,3',5,5'-azobenzene-tetracarboxylic acid (synthesized according to the method of synthesis E described in example 3 below) are dispersed in 5 ml of dimethylformamide (DMF, Aldrich, 99%) with the addition of 0.1 ml of 5M hydrofluoric acid (HF, SDS 50%). The mixture is left in a 23 ml Teflon vessel inserted into a metallic PAAR type bomb for 3 days at 150° C. with an increase gradient over 1 hour. The solid is recovered by filtration.

The solid is then dried at 200° C. under primary vacuum for 15 hours.

Figure 47:
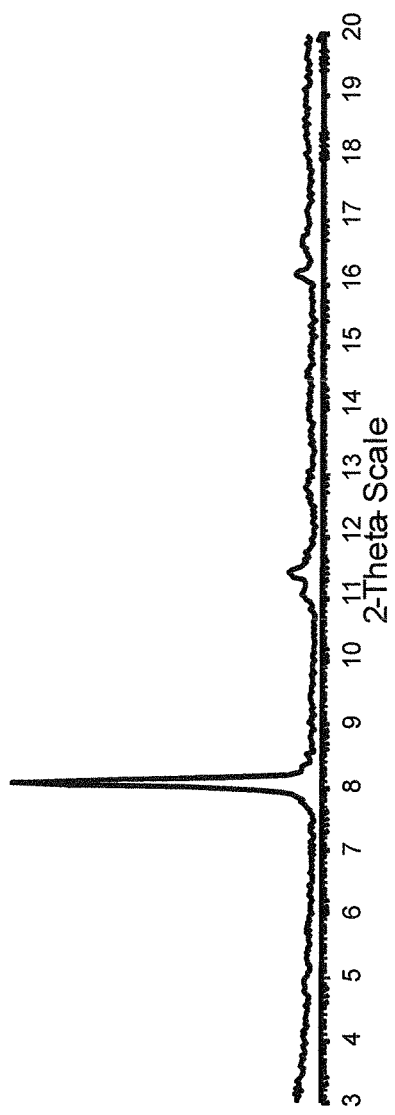
FIG. 47 shows an X-RAY diffraction diagram of the crude synthetic iron 3,3',5,5'-azobenzenetetracarboxylate(III) solid.

Characteristic Data of the MIL-127(Fe) Solid: Iron 3,3',5,5'-azobenzenetetracarboxylate FIG. 47 shows the X-RAY diffraction diagram of the crude synthetic 3,3',5,5'-azobenzenetetrairon carboxylate (III) solid.

The phase, of cubic symmetry, is isostructural with that published by the group of Prof. Eddaoudi [ref 51] for indium (space group Pa3).

Figure 48:
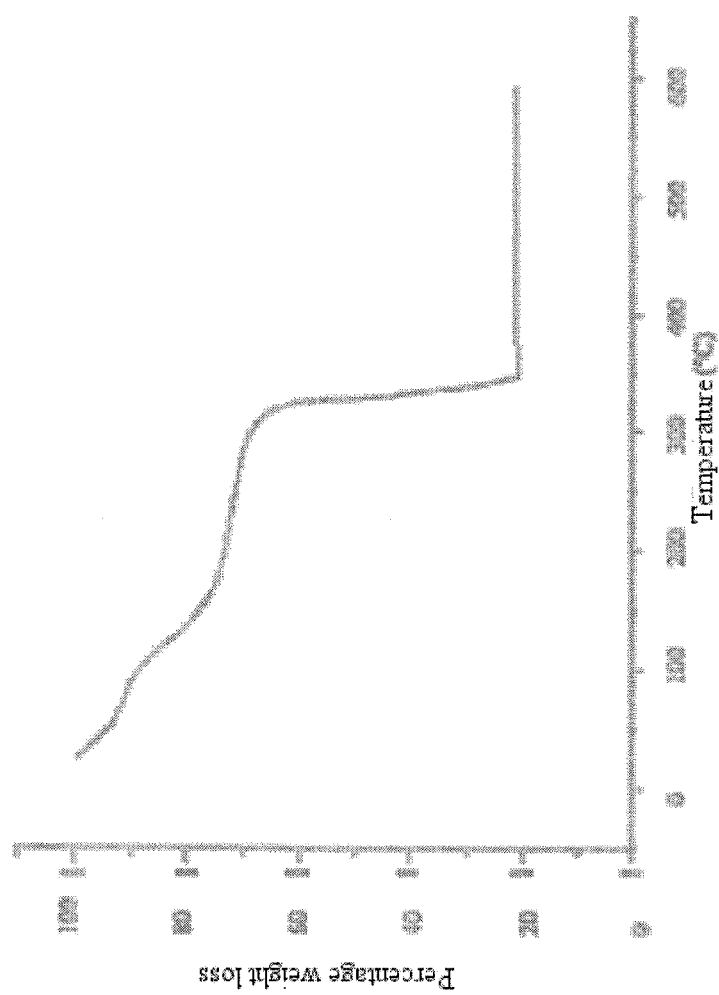
FIG. 48 shows the results of the thermogravimetric analysis of the crude synthetic compound iron 3,3',5,5'-azobenzenetetracarboxylate in air, at a heating rate of 2° C./minute (weight loss Pm as a function of the temperature T).

The results of the thermogravimetric analysis of the crude synthetic compound 3,3',5,5'-azobenzenetetrairon carboxylate (in air, at a heating rate of 2° C./minute) are shown in FIG. 48 (weight loss Pm as function of temperature T).

The observed weight losses at temperatures below 250° C. correspond to the solvent (water, dimethylformamide) present in the pores.

Decomposition of the product takes place at around 300° C. leading to iron oxide(III).

Figure 37:
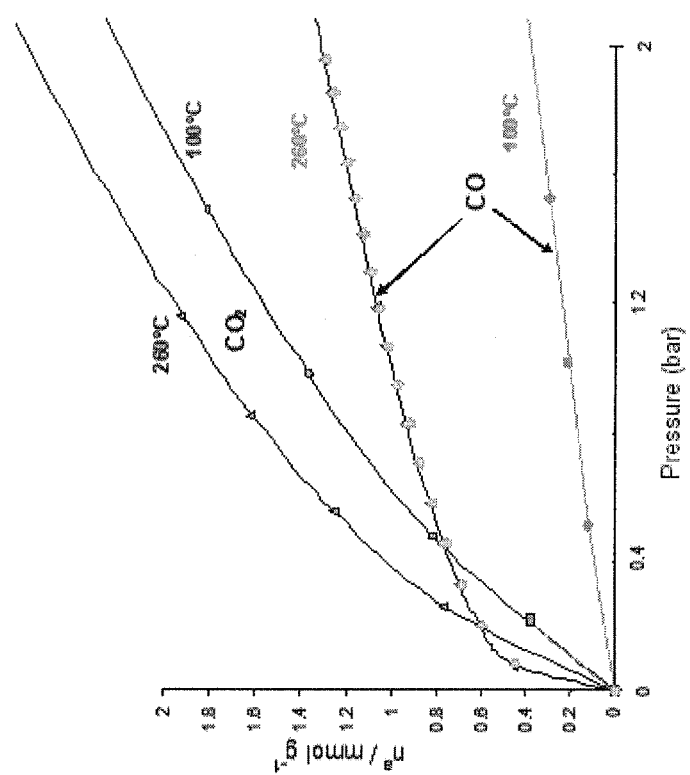
FIG. 37 shows CO/CO$_2$ adsorption isotherms at 303 K with MIL-100(Fe) activated at 100° C. (iron(III)) and MIL-100 (Fe) activated at 260° C. (Iron(II)/Iron(III)). (CO$_2$: two curves at top, CO: two curves at bottom).
Figure 49:
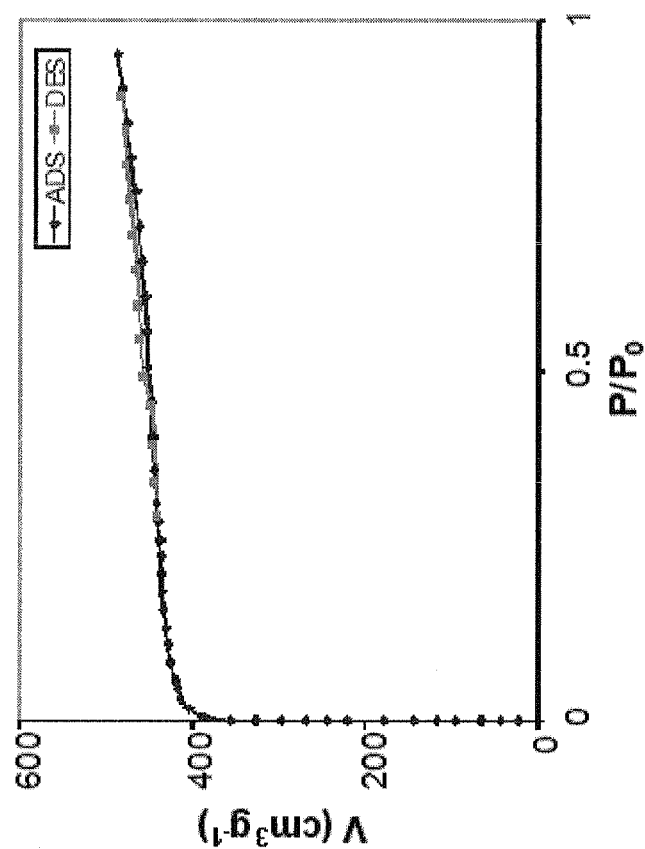
FIG. 49 shows a nitrogen adsorption isotherm of iron 3,3', 5,5'-azobenzenetetracarboxylate (P$_0$=1 atmosphere).

This compound presents a substantial accessible surface area (Langmuir) (greater than 2000 m$^2$/g) to nitrogen at 77 K (FIG. 37) (nitrogen porosimetry Micromeritics instrument ASAP 2010). FIG. 49 shows a nitrogen adsorption isotherm of the 3,3',5,5'-azobenzene-tetrairon carboxylate ($P_0$=1 atmosphere).

x) CPO-27(Fe) or iron 2,5-dihydroxoterephthalate or $Fe_2$ ($_2OC—C_6H_2$ $(OH)_2—CO_2$) $(H_2O).xH_2O$ Synthesis of the Iron 2,5-dihydroxoterephthalate Solid:

270 mg (1 mmol) of $FeClO_3.6H_2O$ (Alfa Aesar, 98%) and 200 mg (1 mmol) of 2,5-dihydroxoterephthalic acid (obtained by hydrolysis of corresponding diethyl ester, Aldrich, 97%) are dispersed in 5 ml of dimethylformamide (DMF, Aldrich, 99%). The mixture is left in a 23 ml Teflon vessel inserted into a metallic PAAR type bomb for 3 days at 150° C. with an increase gradient over 12 hours and a cooling gradient over 24 hours. The solid is recovered by filtration.

The solid is then dried at 150° C. under primary vacuum for 15 hours.

Figure 50:
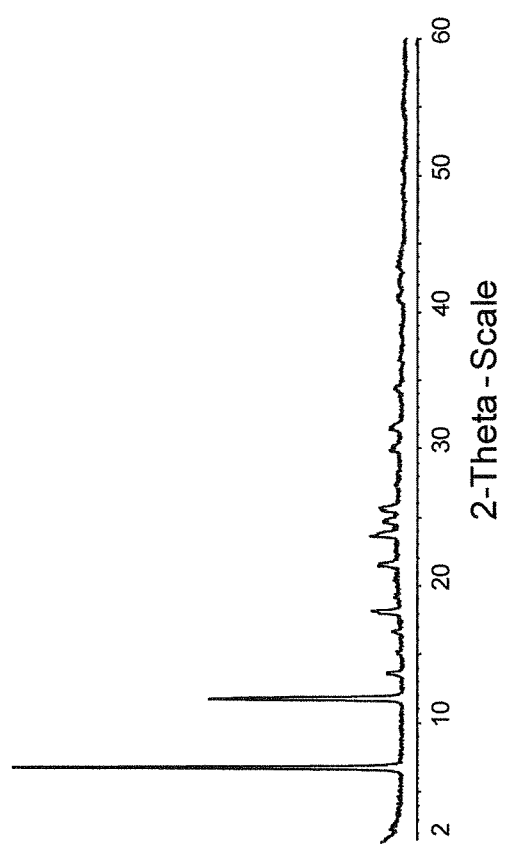
FIG. 50 shows an X-RAY diffraction diagram of the crude iron 2,5-dihydroxoterephthalate (CPO-27(Fe)) solid.

Characteristic Data of the Iron 2,5-dihydroxoterephthalate Solid:

FIG. 50 shows the X-RAY diffraction diagram of the crude iron 2,5-dihydroxoterephthalate solid. The phase, of trigonal symmetry, is an isotype of that published by Dietzel et al. for cobalt and nickel (space group R3) [P. D. C. Dietzel, B. Panella, M. Hirscher, R. Blom, H. Fjellvag, Chem. Commun., 2006, 956-961 [ref 53] and P. D. C. Dietzel, R. E. Johnsen, R. Blom, H. Fjellvag, P. Chem. Eur. J., 2008, 14, 2389-2397 [ref 54]].

y) Example of Synthesis of a Hybrid Mixed Porous MIL-100 Cr/Fe Solid

The hybrid bimetallic MIL-100 solid, containing two different metals, chromium and iron, in its structure was obtained using microwave synthesis (CEM µ Waves, Mars 5) at 200° C. for 1 hour starting from the following molar ratio: Fe:Cr:1,3,5-benzenetricarboxylic acid:HF:HNO$_3$:H$_2$O=X: Y:0.67:2:0.6:278 (X+Y=1).

The solid is recovered by filtration. The solid (200 mg) is then suspended in 100 ml of distilled water under reflux with stirring for 3 hours to eliminate the trimesic acid remaining in the pores. The solid is then recovered by hot filtration.

Figure 51:
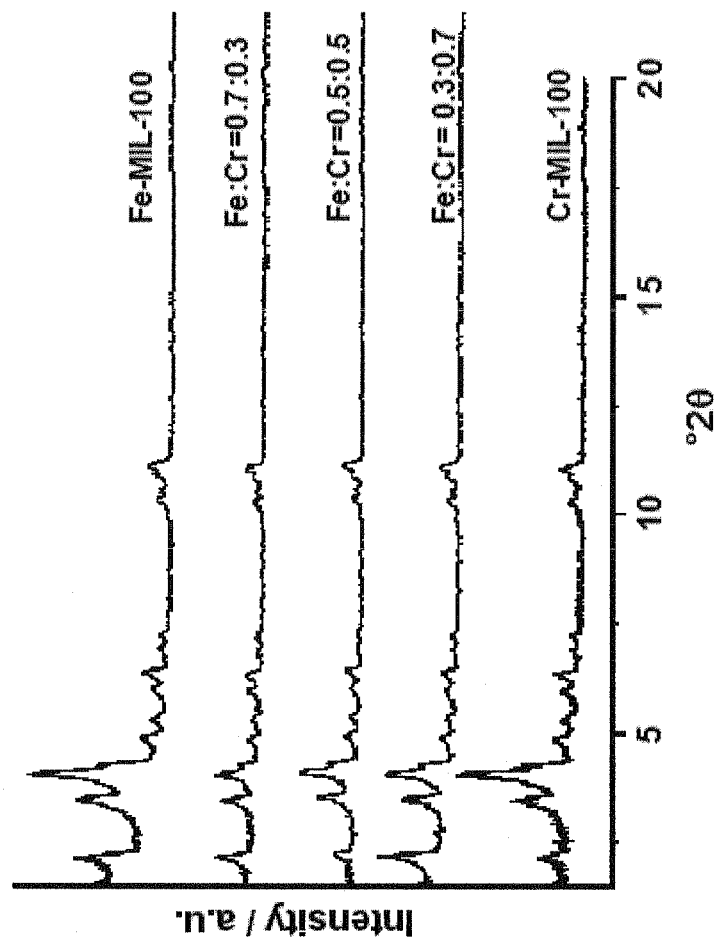
FIG. 51 shows an X-RAY diffraction diagram of MIL-100 solid synthesized from different proportions of Fe:Cr. (Top to bottom: 1:0, 0.7:0.3, 0.5:0.5, 0.3:0.7, 0:1)

FIG. 51 shows the X-RAY diffraction diagram of the MIL-100 solid synthesized starting from different proportions of Fe:Cr (top to bottom: 1:0, 0.7:0.3, 0.5:0.5, 0.3:0.7, 0:1).

Figure 52:
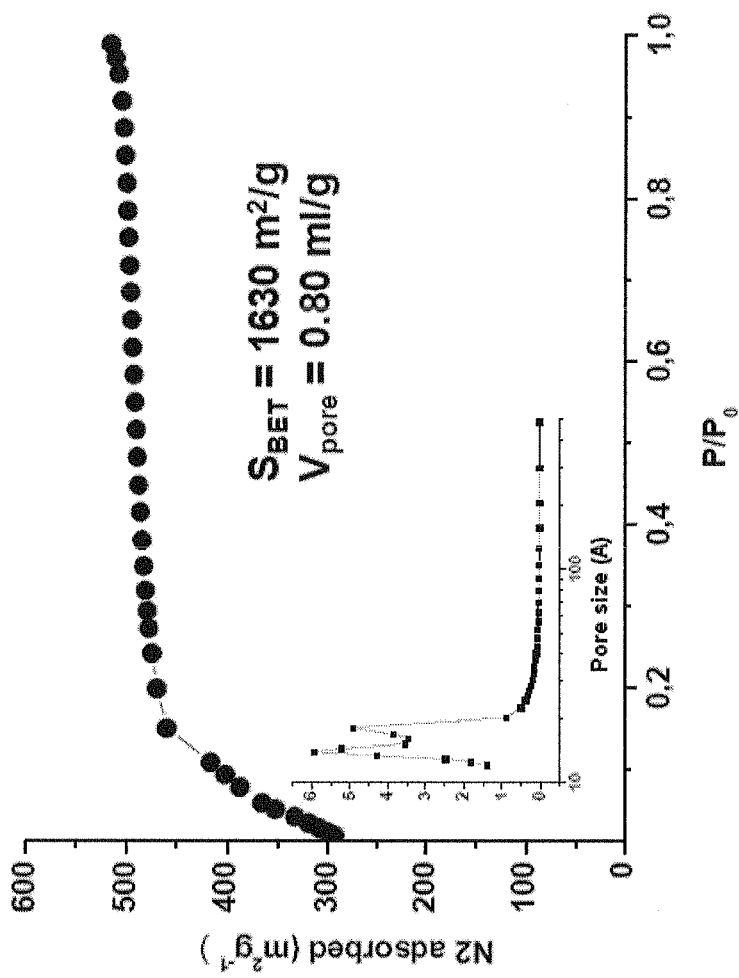
FIG. 52 shows a nitrogen adsorption isotherm of the compound MIL-100 Fe/Cr synthesized from the molar ratio Fe:Cr=0.5:0.5 (P$_0$=1 atmosphere).

The MIL-100 Fe/Cr compound synthesized starting from the molar ratio Fe:Cr=0.5:0.5 presents a substantial accessible surface area (BET) (greater than 1600 m$^2$/g) to nitrogen at 77 K (FIG. 52) (nitrogen porosimetry Micromeritics instrument ASAP 2010). FIG. 52 shows a nitrogen adsorption isotherm of the MIL-100 Fe/Cr compound synthesized starting from the molar ratio Fe:Cr=0.5:0.5 (P=1 atmosphere).

Example 2

Synthesis of Ligands a) Synthesis A: Synthesis of Chloroterephthalic Acid 6 g (0.043 mol) of chloroxylene (marketed by Aldrich, >99%), 16 ml of nitric acid (marketed by VWR, 70%) and 60 ml of distilled water are introduced into a 120 ml Teflon vessel. This is inserted into a metallic PAAR type bomb, heated to 170° C. for 12 hours. The product is recovered by filtration, then washed thoroughly in distilled water. A 75% yield is obtained.

Figure 20:
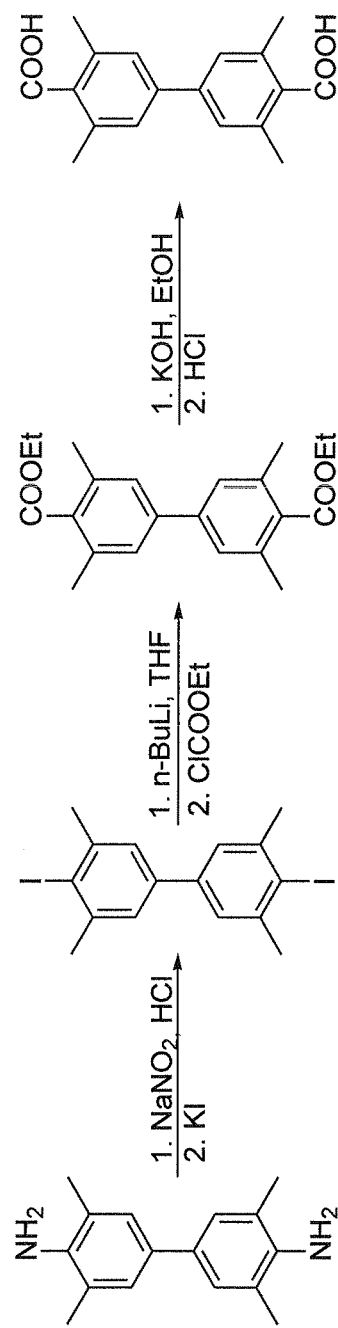
FIG. 20 shows a reaction scheme for the preparation of 3,5,3',5'-tetramethylbiphenyl 4,4'-dicarboxylic acid.

$^1$H NMR (300 MHz, d6-DMSO): δ (ppm): 7.86 (d, J=7.8 Hz), 7.93 (dd, J=7.8, 1.2 Hz), 7.96 (d, J=1.2 Hz)

b) Synthesis B: Synthesis of 3,5,3',5'-tetramethyl-biphenyl-4,4'-dicarboxylic acid The reaction scheme for this synthesis is shown in FIG. 20.
1$^{st}$ Step:
10.2 g of tetramethylbenzidine (98%, Alfa Aesar) are suspended in 39 ml of concentrated hydrochloric acid (37%, marketed by Aldrich) at 0° C. The diazotization was effected by addition of a solution of sodium nitrite (6 g in 50 ml of water). After stirring for 15 minutes at 0° C., a solution of potassium iodide (70 g in 200 ml of water) was slowly added to the resulting violet solution. On completion of the addition, the mixture is stirred for 2 hours at ambient temperature. The resulting black suspension is filtered to recover a black precipitate, which is washed in water. The solid is suspended in dichloromethane (DCM, 98%, marketed by SDS) and a saturated solution of sodium thiosulfate is added, causing decolorization. After stirring for 1 hour, the organic phase is decanted and the aqueous phase is extracted with DCM. The organic phase is dried over sodium sulfate, then evaporated to give the diiodo intermediate in the form of a grayish solid. Elution with pure pentane on a silica column (marketed by SDS) yields the mixture of monoiodo and diiodo compounds. The mixture of these was used directly in the following step.
2$^{nd}$ Step:
7.2 g of the crude iodo compound is dissolved in 100 ml of tetrahydrofuran (THF, distilled over sodium). After cooling to −78° C., 35 ml of n-butyllithium in cyclohexane (2.5 M, marketed by Aldrich) is added. The solution is allowed to return to ambient temperature, a white suspension appearing after 2 hours. It is cooled again to −78° C. and 12 ml of ethyl chloroformate are added. The mixture is allowed to stand at ambient temperature, a clear yellow solution being obtained after 1 hour. Partition between water and dichloromethane, followed by extraction with dichloromethane gives the crude diester. This is purified by chromatography on silica gel, with a 1/9 Et$_2$O/pentane mixture, (front retardation: R$_f$=0.3) as eluent. 6.3 g of diester are obtained in the form of a colorless solid (42% yield from benzidine).

Characterization of diester obtained: $^1$H NMR (300 MHz, CDCl$_3$): δ (ppm): 1.29 (t, J=7.2 Hz, 6H), 2.29 (s, 13H), 4.31 (q, J=7.2 Hz, 4H), 7.12 (s, 4H). $^{13}$C NMR (75 MHz, CDCl$_3$): δ (ppm): 14.3 (CH$_3$), 19.9 (CH$_3$), 61.0 (CH$_2$), 126.5 (CH), 133.2 (quadratic coupling), 135.5 (Quadratic coupling), 141.4 (Quadratic coupling), 169.8 (Quadratic coupling).
3$^{rd}$ Step:
Finally, the diester is saponified with 9.7 g of potassium hydroxide (marketed by VWR) in 100 ml of 95% ethanol (marketed by SDS) under reflux for 5 days. The solution is concentrated under vacuum and the product is dissolved in water. Concentrated hydrochloric acid is added up to pH 1, and a white precipitate is formed. It is recovered by filtration, washed in water and dried. 5.3 g of diacid are thus obtained in the form of a white solid (quantitative yield).

c) Synthesis C: synthesis of 3,3'-dimethylbiphenyl 4,4'-dicarboxylic acid

Figure 21:
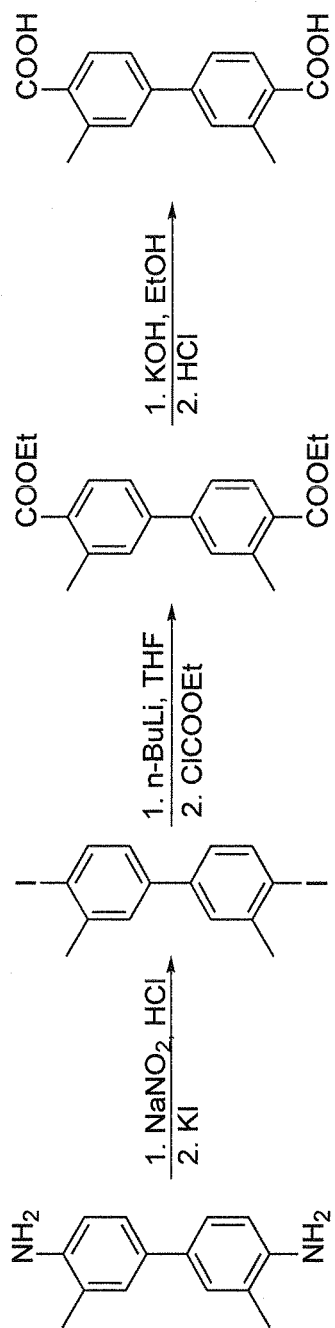
FIG. 21 shows a reaction scheme for the preparation of 3,3'-dimethylbiphenyl 4,4'-dicarboxylic acid.

The reaction scheme for this synthesis is shown in FIG. 21.
The same procedure as that described for synthesis B was used starting with 12.1 g of dimethylbenzidine. After the 1$^{st}$ step, 18.4 g of 3,3'-dimethyl-4,4'-diiodobiphenyl are obtained (yield: 74%).

Characterization of the diiodo compound obtained: $^1$H NMR (300 MHz, CDCl$_3$): δ (ppm): 2.54 (s, 6H), 7.10 (dd, J=2.2 and 8.1 Hz, 2H), 7.46 (d, J=2.2 Hz, 2H), 7.90 (d, J=8.1 Hz, 2H). $^{13}$C NMR (75 MHz, CDCl$_3$): δ (ppm): 28.3 (CH$_3$), 100.3 (Quadratic coupling), 126.0 (CH), 128.3 (CH), 139.4 (CH), 140.4 (Quadratic coupling), 141.9 (Quadratic coupling).

After the 2$^{nd}$ and 3$^{rd}$ steps, 6.9 g of 3,3'-dimethyl-biphenyl-4,4'-dicarboxylic acid are obtained from the 18.4 g of diiodo compound.

Characterization of the Compounds Obtained:
The diester obtained after the 2$^{nd}$ step and the diacid obtained after the 3$^{rd}$ step have identical spectroscopic signatures to those described in the literature (Shiotani Akinori, Z. Naturforsch. 1994, 49, 12, 1731-1736 [ref. 32]).

d) Synthesis D: synthesis of 3,3'-dichloro-4,4'-azobenzenedicarboxylic acid 15 g of o-chlorobenzoic acid (marketed by Aldrich, 98%) and 50 g of sodium hydroxide are placed in 225 ml of distilled water, and heated to 50° C. with stirring. 100 g of glucose (Aldrich, 96%) dissolved in 150 ml of water are added. The mixture is stirred for 15 minutes, then air is bubbled through for 3 hours, at ambient temperature. The disodium salt is recovered by filtration, washed in ethanol, then redissolved in 120 ml of water. Hydrochloric acid (marketed by Aldrich VWR, 37%) is added until a pH of 1 is obtained. The solid is recovered by filtration and vacuum-dried at 90° C.

e) Synthesis E: Synthesis of 3,3',5,5'-azobenzenetetracarboxylic acid 19 g of nitroisophtalic acid (marketed by Aldrich, 98%) and 50 g of sodium hydroxide are placed in 225 ml of distilled water, and heated at 50° C. with stirring. 100 g of glucose (Aldrich, 96%) dissolved in 150 ml of water is added. The mixture is stirred for 15 minutes, then air is bubbled through for 3 hours at ambient temperature. The tetrasodium salt is recovered by filtration, then redissolved in 300 ml of water. Hydrochloric acid (marketed by Aldrich VWR, 37%) is added until a pH of 1 is obtained. The solid is recovered by centrifugation (4000 rpm/10 min), washed in water and vacuum-dried at 90° C.

Example 3

Determination of the Flexibility of the MOF Materials

The flexibility of the Fe, Cr, V, Mn and/or Co carboxylate MOF materials can be determined by X-RAY diffraction. The paragraphs that follow indicate a method which can be used to demonstrate the possible flexibility of the MOF materials. In particular, the inventors have demonstrated the flexibility of certain MOF materials named "MIL-88".

On reading what follows, the reader will be in a position to adapt the method to establish which of the MOF materials containing a three-dimensional structure of moieties of formula (I) have a rigid structure, and are therefore capable of being used in the process of the invention.

Figure 23:
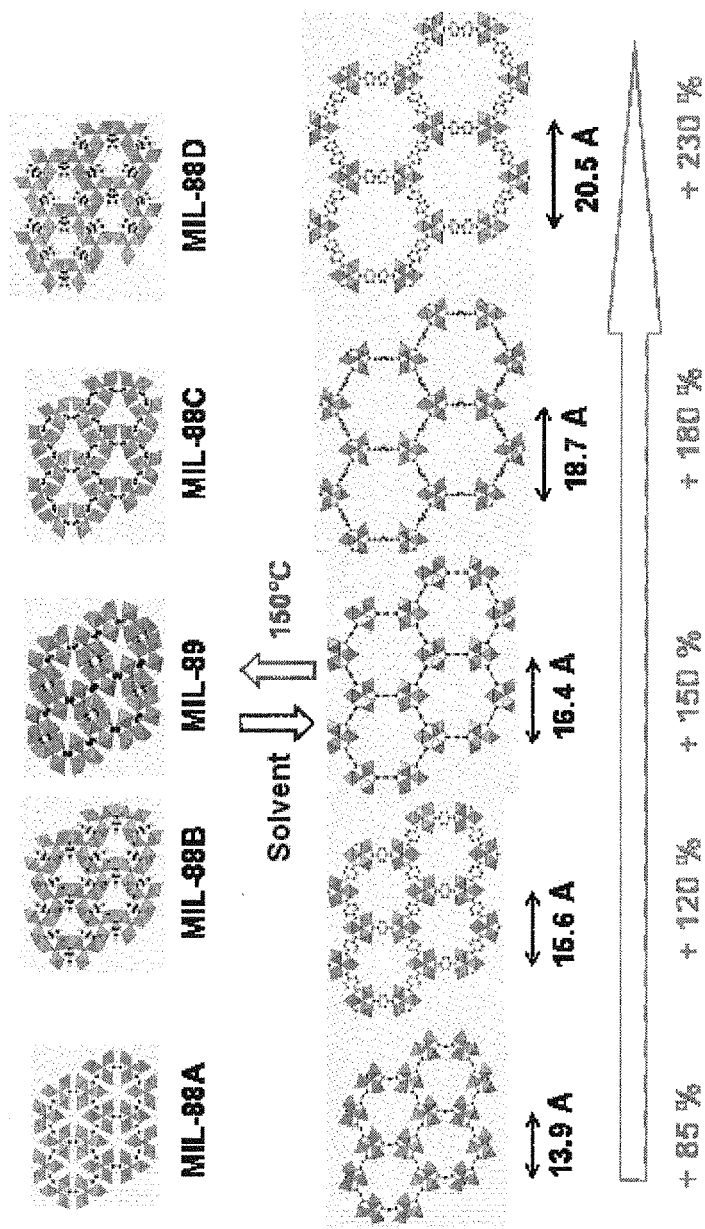
FIG. 23 shows a schematic view of the respiration (swelling and contraction) phenomenon in the MIL-88A, MIL-88B, MIL-88C, MIL-88D and MIL-89 solids. The amplitude of swelling between dry (above) and open forms (below) is shown in % at the foot of the figure.
Figure 24:
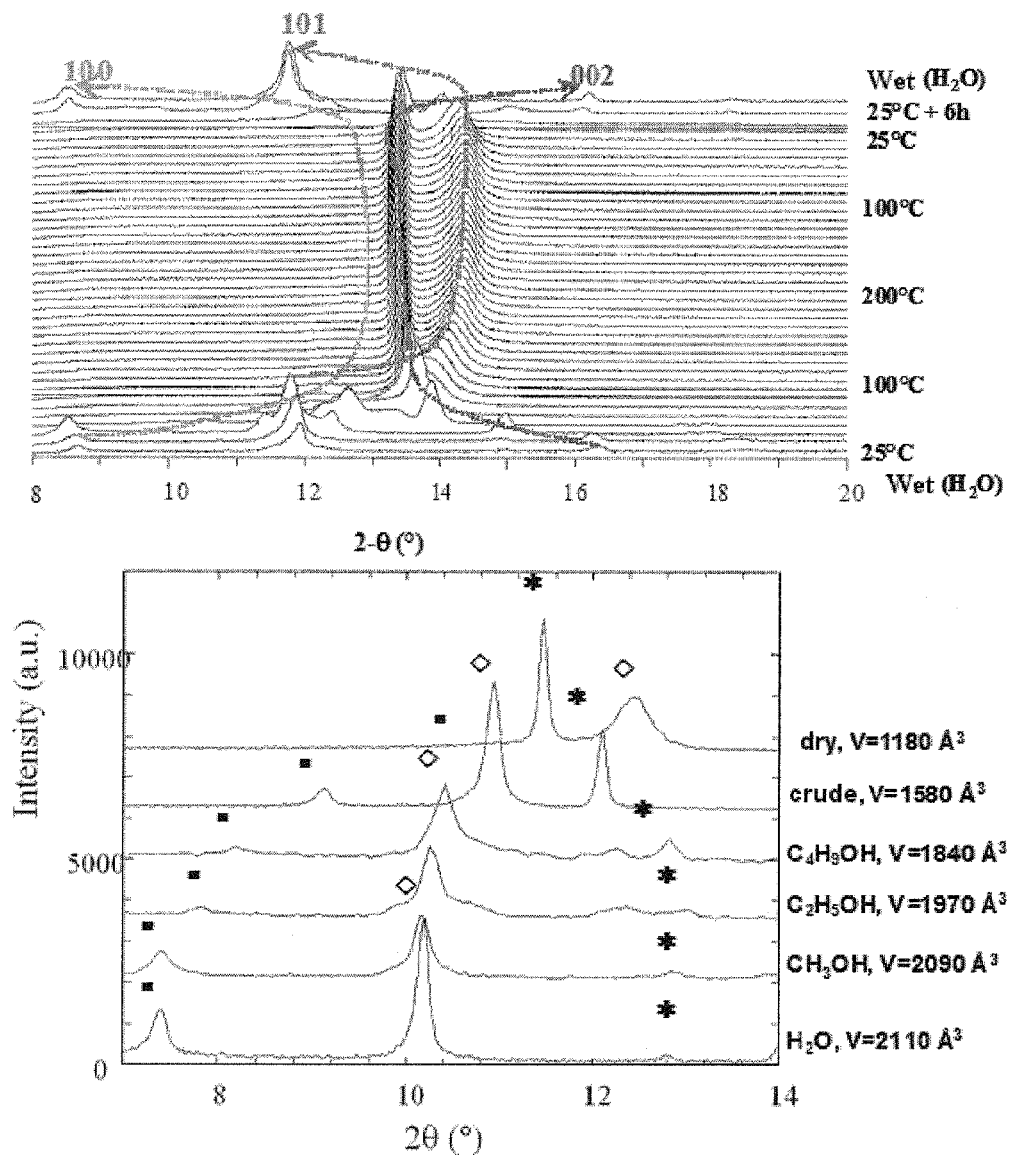
FIG. 24 shows, above, a study of the reversibility of the swelling of the MIL-88A solid by X-RAY diffraction ((~1.79 Å), and below, X-RAY diffraction diagrams of the MIL-88A solid in presence of solvents ((~1.5406 Å).

The category of flexible hybrid solids based on trimers of trivalent transition metals (Fe, Cr, V, Mn . . . ) is named MIL-88. These compounds are typically made up of trimers of iron octahedra, in other words three iron atoms connected by a central oxygen and by six carboxylate groups connecting the iron atoms two by two, and one terminal molecule of water coordinated at each iron atom then completes the octahedral coordination of the metal. These trimers are then linked together by aliphatic or aromatic dicarboxylic acids to form the MIL-88A, B, C, D and MIL-89 solids (-A for fumaric acid, —B for terephthalic acid, —C for 2,6-naphthalenedicarboxylic acid, -D for 4,4'-biphenyldicarboxylic acid and MIL-89 for trans,trans muconic acid), as described in the document by Serre et al., *Angew. Chem. Int. Ed.* 2004, 43, 6286 [ref. 17]. Other analogs with other carboxylic diacids have also been synthesized and are named MIL-88E, F, The study of the behavior of these solids by X-RAY diffraction made it possible to establish that these compounds are flexible with considerable "breathing" (in other words swelling or contraction) amplitudes between their dry form and their solvated from. This results in variations in cell volume between 85 and 230% depending on the nature of the organic spacer (FIG. 23), as described in the document Serre et al., *Science,* 2007, 315, 1828 [ref. 33]. The inventors noted that the dry forms are not porous, with an almost identical pore (tunnel) size whatever the carboxylic ligand used. In contrast, the swelling of the hybrid solid in the liquid phase is a function of the length of the organic spacer. Thus, the distance between trimers in the swelled form ranges from 13.8 Å with fumaric acid (MIL-88A) to 20.5 Å with the biphenyl ligand (MIL-88D). The size of the pores of the swelled forms thus varies between 7 Å (MIL-88A) and 16 Å (MIL-88D). The swelling is reversible, as is shown by the example of the MIL-88A solid in presence of water in FIG. 24) and also depends on the nature of the solvent used as described in the document Serre et al. *J. Am. Chem. Soc.,* 2005, 127, 16273-16278 [ref. 34]. The "breathing" takes place in a continuous manner, without apparent bond breakage during the breathing. Moreover, on returning to ambient temperature, the solid swells again by resolution, confirming the reversible nature of the breathing.

If one looks closely at the arrangement between the constituent trimers of the structure, each trimer is linked to six other trimers, three below and three above, by the dicarboxylates which results in the formation of bipyramidal cages of trimers. Within these cages, the connection between trimers is effected only along the axis c and the absence of any linkage in the plane (ab) is the reason for the flexibility (FIG. 25).

TABLE 10

| Solid | Condition | a (Å) | c (Å) | V (Å$^3$) | Expansion of the cell | Estimated pore size | Solvent |
|---|---|---|---|---|---|---|---|
| MIL-88A | 100° C. | 9.6 | 14.8 | 1180 | >80% | about 6 Å | Water |
|  | 25° C. | 11.1 | 14.5 | 1480 |  |  |  |
|  | Open form | 13.8 | 12.5 | 2100 |  |  |  |
| MIL-88B | 100° C. | 9.6 | 19.1 | 1500 | >100% | about 9 Å | Ethanol |
|  | 25° C. | 11.0 | 19.0 | 2000 |  |  |  |
|  | Open form | 15.7 | 14.0 | 3100 |  |  |  |
| MIL-88C | 100° C. | 9.9 | 23.8 | 2020 | >170% | about 13 Å | Pyridine |
|  | 25° C. | 10.2 | 23.6 | 2100 |  |  |  |
|  | Open form | 18.7 | 18.8 | 5600 |  |  |  |
| MIL-89 | 100° C. | 9.15 | 20 | 1470 | >160% | about 11 Å | Pyridine |
|  | 25° C. | — | — | — |  |  |  |
|  | Open form | 17.0 | 15.7 | 3900 |  |  |  |
| MIL-88D | 100° C. | 10.1 | 27.8 | 2480 | >220% | about 16 Å | Ethanol |
|  | 25° C. | 12.1 | 27.5 | 3500 |  |  |  |
|  | Open form | 20.5 | 22.4 | 8100 |  |  |  |

Figure 25:
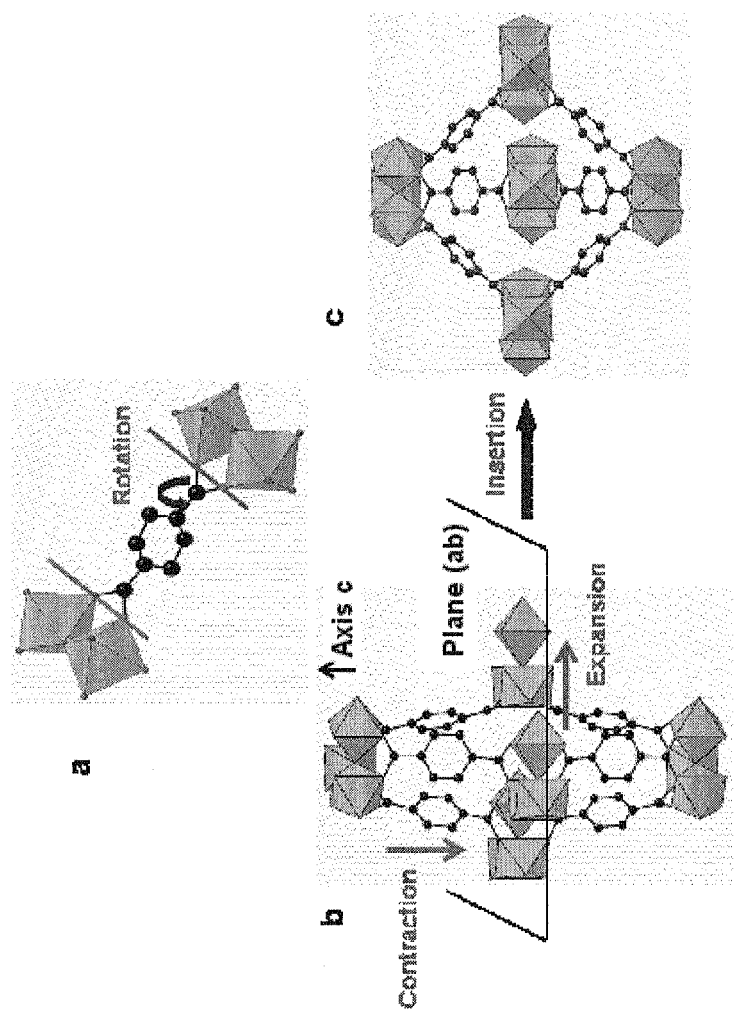
FIG. 25 shows an explanatory scheme of the flexibility in the hybrid phases MIL-53 (a) and MIL-88 (b and c).

In fact, when a solvent is inserted into the material the cage deforms with trimers moving together along the axis c and moving apart in the directions a and b, which causes an overall increase in the volume of the cage (FIG. 25). Finally, the flexibility of these hybrid solids is remarkable, but nonetheless comparable to that of certain polymers. The main difference relates to the crystallinity of the hybrid solids, the polymers being amorphous. Finally, in contrast to the polymers, the swelling takes place in the hybrid solids anisotropically.

TABLE 11

"MIL" structures of some iron(III) carboxylates.

| MIL-n solid | Organic fraction | Formula |
|---|---|---|
| MIL-88A | Fumaric acid | $Fe_3OX[O_2C-C_2H_2-CO_2]_3 \cdot nH_2O$ |
| MIL-88B_4CH3 | Terephthalic acid | $Fe_3OX[O_2C-C_6(CH_3)_4-CO_2]_3 \cdot nH_2O$ |
| MIL-89 | Muconic acid | $Fe_3OCl[O_2C-C_4H_4-CO_2]_3 \cdot nH_2O$ |
| MIL-100 | 1,3,5-benzene tricarboxylic acid (1,4-BTC acid) | $Fe_3OX[C_6H_3-[CO_2]_3] \cdot nH_2O$ |
| MIL-101 | Terephthalic acid | $Fe_3OX[O_2C-C_6H_4-CO_2]_3 \cdot nH_2O$ |
| MIL-102 | 1,4,5,8 naphthalenetetracarboxylic acid | $Fe_6O_2X_2[C_{10}H_2(CO_2)_4]_3$ |

TABLE 1

Characteristics of the "MIL" structures of iron(III) carboxylates.

| MIL-n | % iron* | Pore diameter (Å)** | Flexibility | Metallic base |
|---|---|---|---|---|
| MIL-88A | 30.8% | 6 | yes | Octahedron trimer |
| MIL-88B_4CH3 | 21.2% | 7 | yes | Octahedron trimer |
| MIL-96 | 29.9% | 4 and 8 | no | Trimer and chain |
| MIL-89 | 26.2% | 11 | yes | Octahedron trimer |
| MIL-100 | 27.3% | 25-29 | no | Octahedron trimer |
| MIL-101 | 24.2% | 29-34 | no | Octahedron trimer |
| MIL-102 | 25.8% | 4 | no | Octahedron trimer |

*theoretical % iron in the dry phase
**pore size calculated from crystallographic structures Example 4

MIL-100(Fe)

Figure 19:
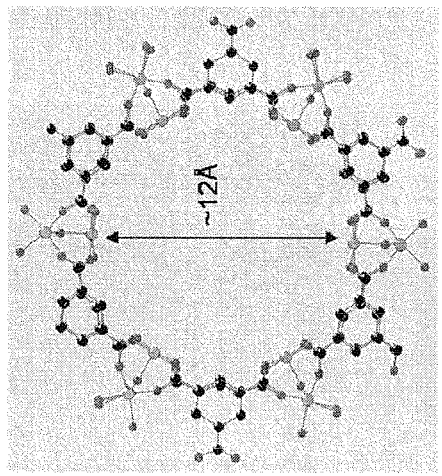
FIG. 19 shows the pentagonal and hexagonal windows of the MIL-100(Fe) solid after activation under vacuum.
Figure 19:
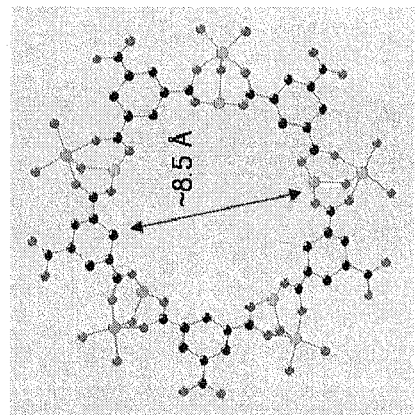

The iron carboxylate MOF material MIL-100(Fe) is made up of trimers of octahedra of chromium or iron linked by trimesic acids which associate to form hybrid super-tetrahedra [Horcajada et al., ref. 28]. The whole thus results in a crystallized mesoporous structure the cages of which, having a free size of 25 and 29 Å, are accessible via microporous windows (FIG. 19). The resulting pore volume is very large, close to 1.2 g·cm$^{-3}$ for a specific BET surface area of 2200 m$^2$·g$^{-1}$.

Figure 27A:
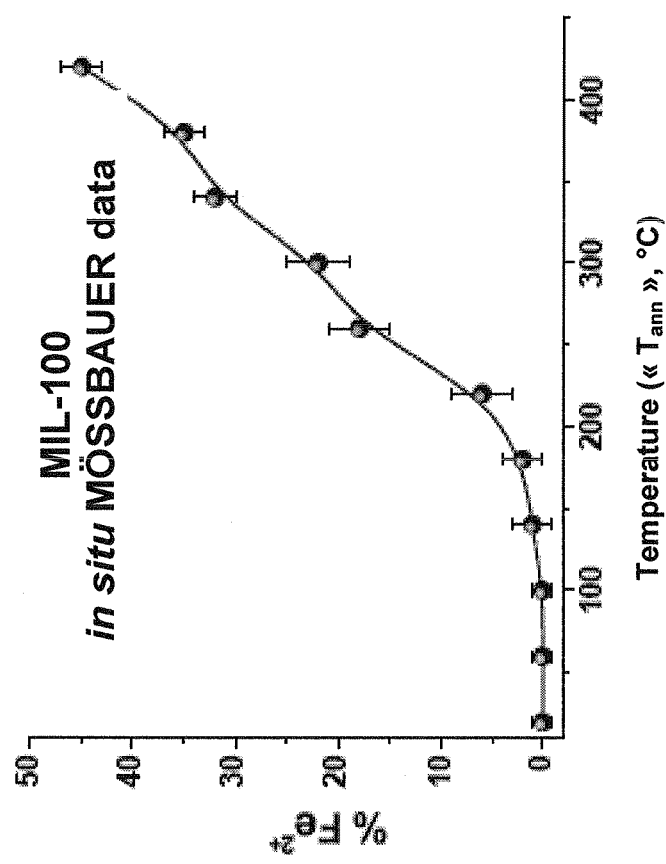
FIG. 27A shows a graph showing the variation in the level of iron(II) in MIL-100(Fe) as a function of the activation temperature under vacuum by Mossbauer spectroscopy.
Figure 27B:
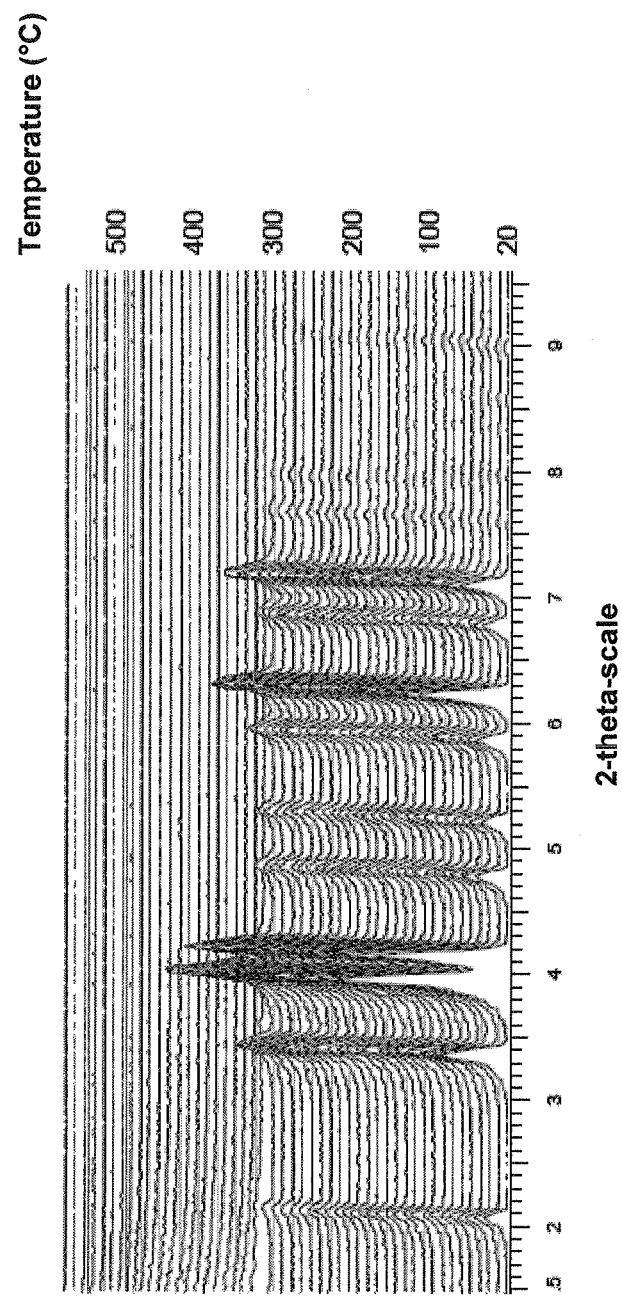
FIG. 27B shows an X-RAY diffraction diagram (X-RAY thermodiffraction under vacuum) of the MIL-100(Fe) solid ($\lambda_{Cu}$=1.5406 Å).

The distinctive feature of this solid is the stability of its structure after the departure of the water coordinated on the metal centers [ref. 35]. The latter is easily removed by heating under vacuum and gives way to unsaturated and accessible metal centers (metal at coordination level five). Moreover, when the activation temperature under vacuum exceeds 150° C., a partial reduction of the iron(III) to iron(II) takes place. This reduction takes place to an extent increasing with the temperature and does not destabilize the structure before 280° C., as is shown by X-RAY thermodiffractometry under vacuum (FIG. 27B). It is possible to reduce the iron(III) to iron(II) at a lower temperature than 150° C. by allowing the solid to activate for a sufficiently long time. Of course, the higher the activation temperature, the faster the dehydration takes place and the faster the reduction (kinetic effect). Indeed the C3 separation is much better when the MOF solid is activated for 12 hours under He at 15° C. compared to 3 hours.

As regards the maximal level of reduction at a defined temperature, without wishing to be bound in any way to one particular theory, it seems that it can be proposed that this is doubtless controlled by the thermodynamics.

The composition of the MIL-100(Fe) solid is $Fe^{III}_3O(H_2O)_2F.\{C_6H_3-(CO_2)_3\}_2.nH_2O$ (n~14.5). Its framework is cationic with one compensating anion per iron trimer. Here the anion is a fluoride which is coordinated onto the iron. The stability of the MIL-100(Fe) to partial reduction of the iron (III) to iron(II) could be explained by a departure of conjugated fluorine on reduction of the iron. Thus, it is entirely reasonable to think that one iron(III) per trimer may be reduced to iron(II) at the same time as a departure of fluoride ions to observe electrical neutrality. On return to ambient temperature, in air, the solid reoxidizes with probable coordination of OH anions onto the iron. This property is fundamental and to our knowledge unique in the field of the MOFs: the reduction of an unsaturated metal center under vacuum while maintaining the integrity of the structure.

Figure 26:
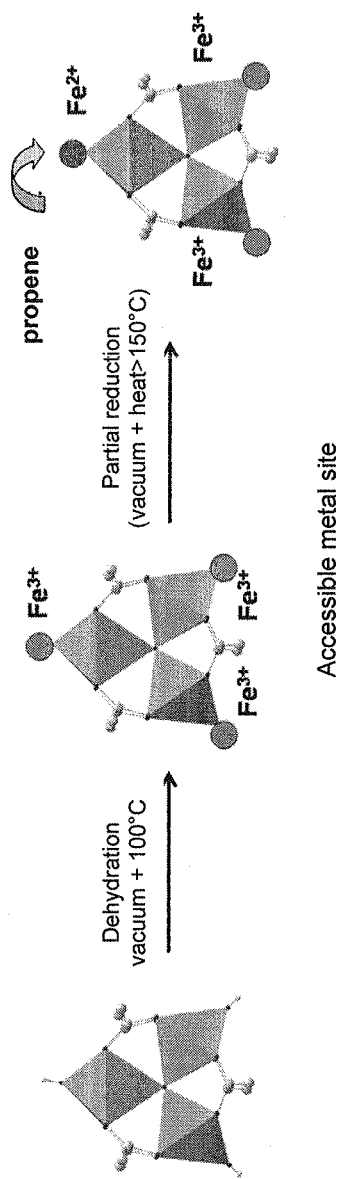
FIG. 26 shows a summarizing diagram of the activation of the MIL-100(Fe) solid.

The unsaturated iron(II) and iron (III) metal centers are electron accepting (Lewis acid) in nature and form π complexes with molecules which are electron donating (Lewis base) in nature, such as alkenes or alkynes. The stabilization of the complexes thus formed can be explained on the basis of the Dewar-Chatt-Duncanson model [ref. 9] by considering on the one hand the electronic structure of the double or triple carbon-carbon bond of the olefin and on the other the vacant orbitals of the adsorption site: the bond with the alkene or the alkyne involves (i) delocalization of the electrons of the bonding π orbitals of the unsaturated hydrocarbon towards the vacant orbitals of the adsorption site (donor-acceptor interaction by σ bond) and (ii) delocalization of the electrons of the partially filled d orbitals of the adsorption site towards the anti-bonding π* orbitals of the unsaturated hydrocarbon (π bond). Iron (II) has an additional d electron compared to iron(III), which reinforces the π bond with the hydrocarbon and thus increases the stability of the complex formed. Thus, the partially reduced MIL-100(Fe) will be able to interact more strongly with such molecules (FIG. 26).

Example 5

Determination of the Iron(II) Content in the Activated MIL-100(Fe) Solid

Activation:

In order to empty the pores of the material (solvents, residual acids) and to free the coordination sites of the metal, the activation of the MIL-100(Fe) material was effected by heating at 150° C. under primary vacuum for 15 hours. The resulting solid only contains iron at the oxidation level +III. $Fe^{3+}/Fe^{2+}$ reduction:

The partial reduction of the MIL-100(Fe) material was effected by heating at 250° C. under primary vacuum for hours. By infrared spectroscopy it was possible to quantify the relative iron(II)/iron(III) content at around 20/80% (FIG. 22).

Figure 22:
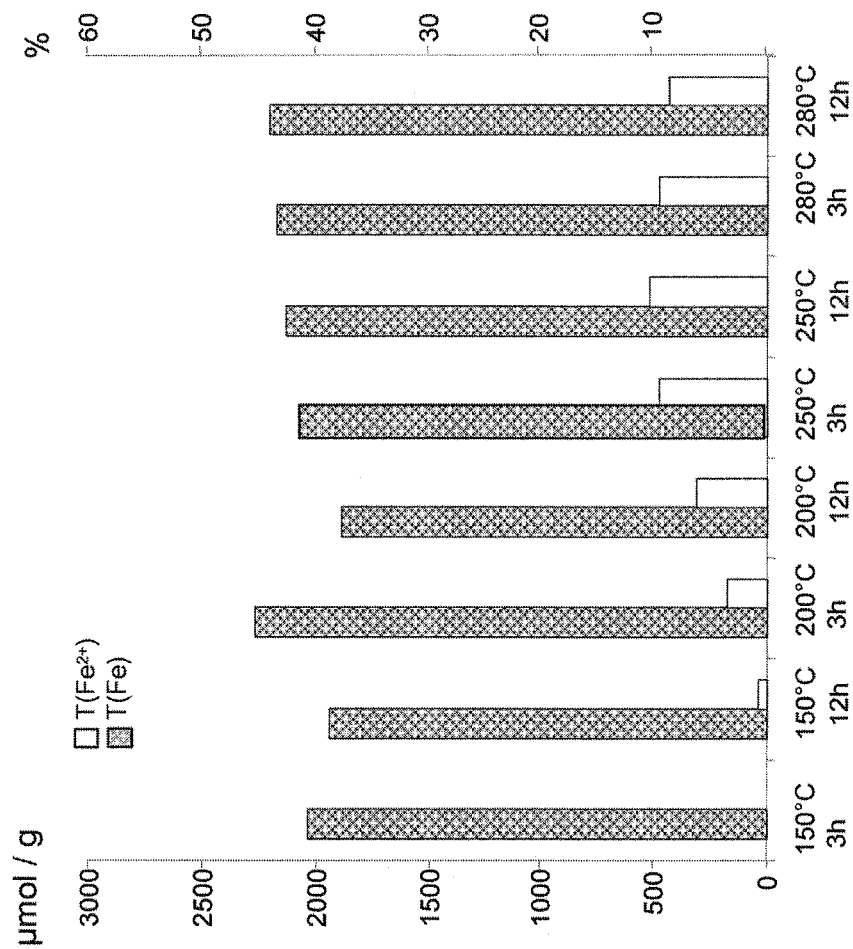
FIG. 22 shows a quantity of unsaturated iron sites present in the fluorinated MIL-100(Fe) (X=F) activated under vacuum at different temperatures.

FIG. 22 shows the quantity of coordinatively unsaturated iron sites present in the MIL-100(Fe) solid activated depending on the heat treatment performed. The MIL-100(Fe) solid is activated under residual vacuum (about $0.0075 \cdot 10^{-5}$ Pa ($10^{-5}$ mm Hg)) at different temperatures and for different periods. T(Fe) represents the content of coordinatively unsaturated iron sites and $T(Fe^{2+})$ represents the content of coordinatively unsaturated $Fe^{2+}$ sites (in µmole of unsaturated sites per gram of activated solid or in % unsaturated iron sites).

The quantities of unsaturated iron sites are determined by CO adsorption at 100 K followed by infrared spectroscopy. The uncertainty on the values is estimated at +/−10%.

Experimental Conditions Used for the Breakthrough and Thermodesorption Type Experiments of Examples 6 to 13

Figure 29:
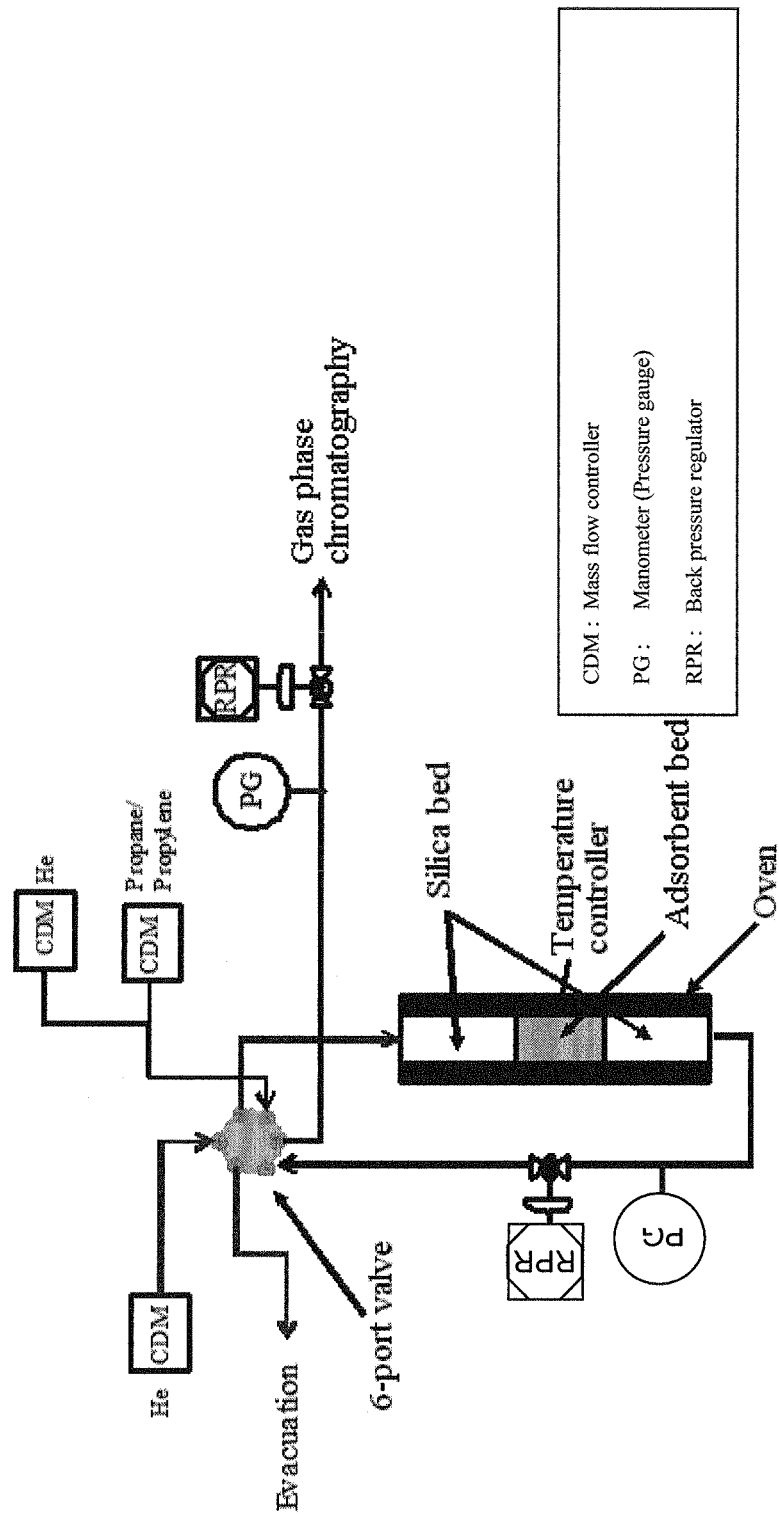
FIG. 29 shows a summarizing diagram of the experimental set-up used for the column separation tests of examples 6 to 13.

The gas separation properties of the MIL-100(Fe) solid were tested during breakthrough experiments using mixtures of $C_3H_8/C_3H_6$ and $C_2H_4/C_2H_2$ in equimolar proportion with helium as carrier gas. 1.3 gram of hydrated MIL-100(Fe) solid was introduced into and compacted in a stainless steel column (9.5 mm external diameter and 20 cm length). The column was then attached to a gas separation apparatus as described in FIG. 29. Prior to the separation tests, the sample was activated at the required temperature (between 120 and 300° C.) under a 30 ml/min current of helium for 10 hours. Next the sample was cooled to 40° C. (or other temperature if specified) and maintained at that temperature for 2 hours. For the experiments at atmospheric pressure (1 bar), an equimolar mixture of propane/propylene at 7.4 mol % in helium was introduced into the column containing the adsorbent MIL-100(Fe) activated at a constant flow rate of 30 ml/minute. The same conditions were applied to the experiments at higher pressure (5 and 8 bars). The composition emerging from the column was analyzed every minute with a gas phase chromatograph (Donam DS6200 GC) fitted with a flame ionization detector and a capillary column (J&W, Alumina, 30 m×0.55 mm). The concentration of each gas was standardized to the same level during the purge of the mixture of gases (specific outlet) before its passage through the column. After each breakthrough experiment, temperature-programmed desorption experiments (TPD) on the solid loaded with gas mixture were performed on the same instrument with a current of helium as carrier gas with a heating rate of 10K/min from the adsorption temperature up to 300° C.

Experimental Conditions Used for the Adsorption Experiments at Thermodynamic Equilibrium by Gravimetry (Examples 6 and 8)

Description of the Experimental Set-Up

The study of a coadsorbed binary mixture requires evaluation of the composition of the two gases and the adsorbed phases for each point at equilibrium. The set-up used here is made up of three parts: a manometric dose introduction system, a gravimetry instrument associated with in situ measurements of density, and a gas phase chromatograph which makes it possible to study the coadsorption of several types of gas.

Figure 30:
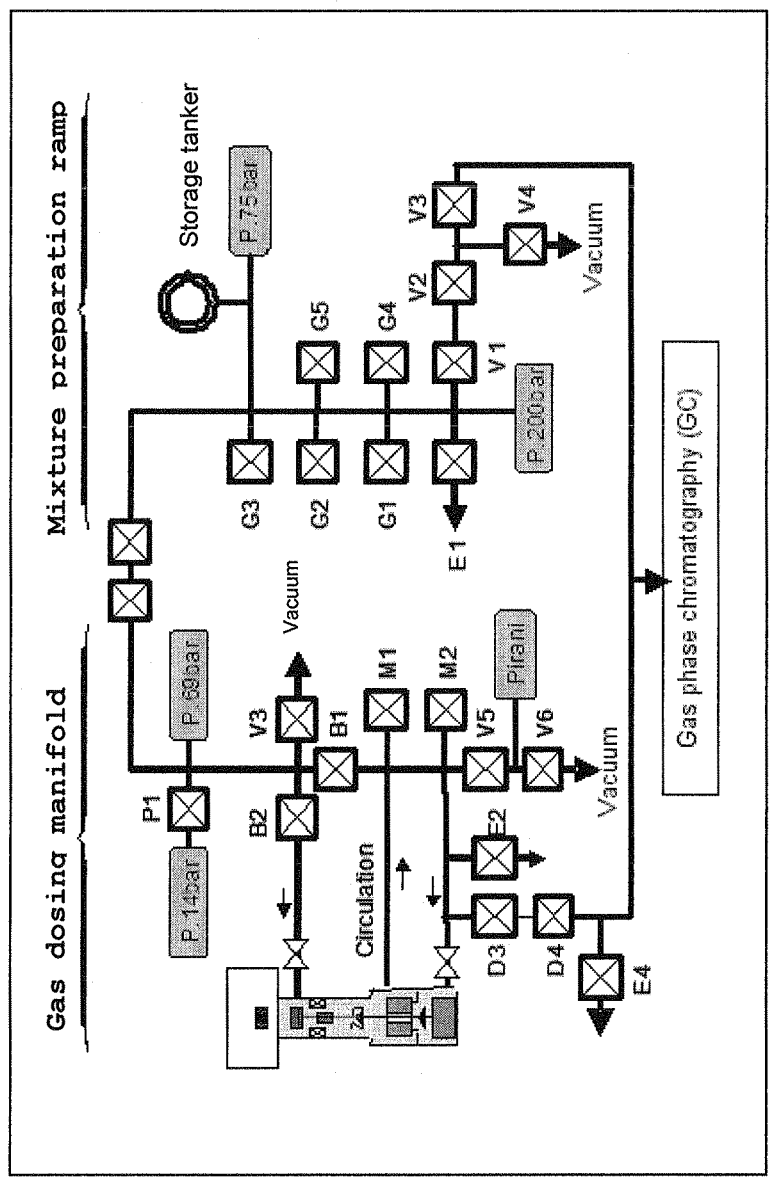
FIG. 30 shows a schematic diagram of the manometric system for introduction of doses of gas used for examples 6 and 8.
Figure 31:
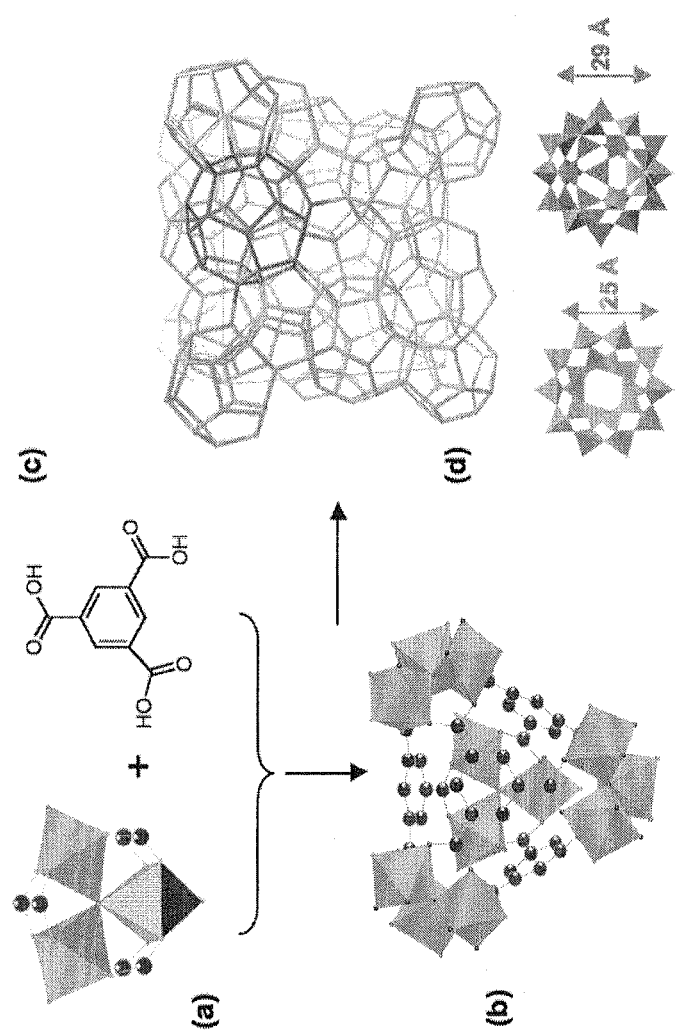
FIG. 31: Top: construction of the MIL-101 solid from trimers of octahedra of iron, and 1,4 benzene-dicarboxylic acid to form a hybrid supertetrahedron and finally a hybrid zeolite structure of large pore size. Bottom: schematic view of the porous framework and representation of the two types of mesoporous cage, with their free dimensions. The iron octahedra and the carbon atoms are in green and black respectively.
Figure 32:
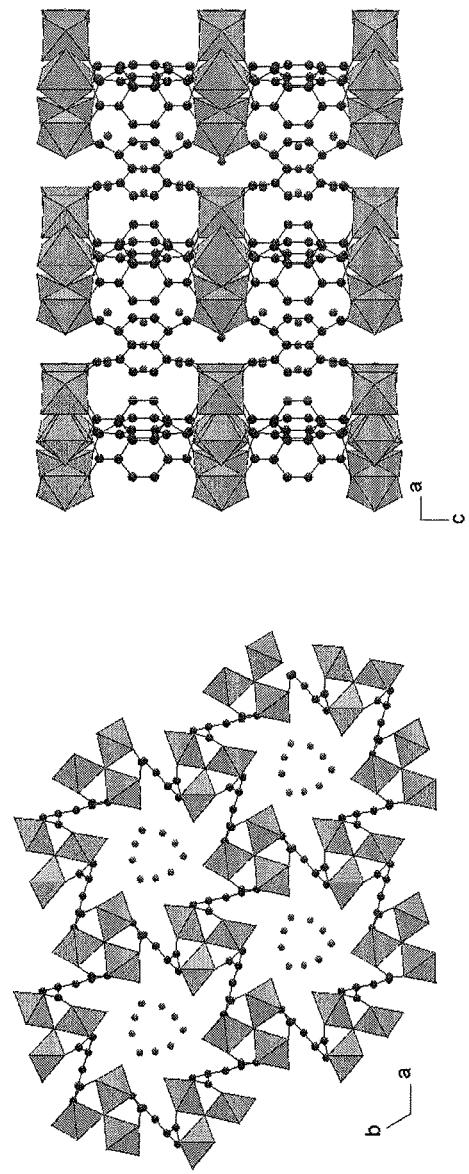
FIG. 32 shows the structure of the MOF solid MIL-102 (Fe). Left: view along the axis of the tunnels (axis c), right: view along the axis perpendicular to the tunnels (axis b, similar view along the axis a). The atoms of iron and carbon and the molecules of water are in green, black and red respectively.
Figure 33:
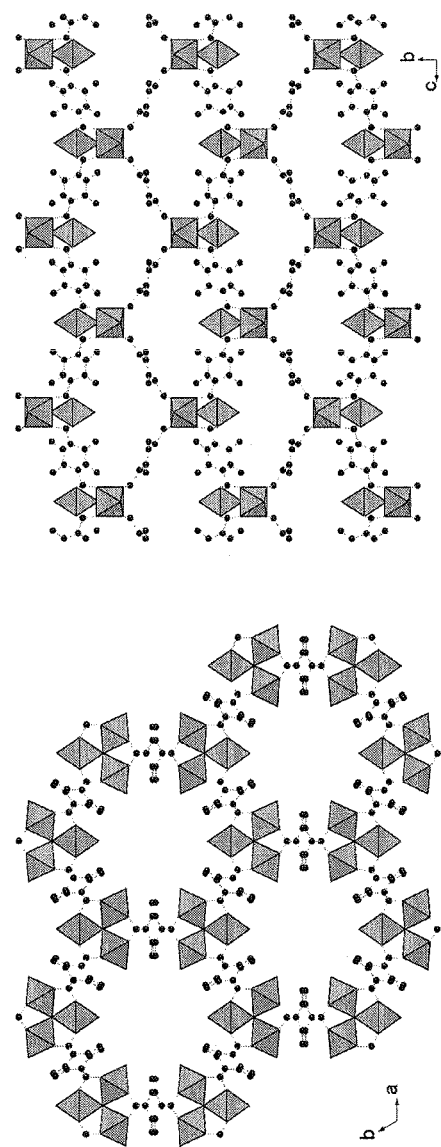
FIG. 33 shows the structure of the MOF solid MIL-88B_4CH$_3$(Fe). Left: view along the axis of the tunnels (axis c), right: view along the axis of the cages (axes a and b equivalent). The iron octahedra and the carbon atoms are in orange and black respectively.

A diagrammatic representation of the "home-made" manometric instrument is described in FIG. 30. It comprises two parts. On the first up to 5 cylinders of gas can be connected which enables the preparation of complex mixtures. The gases are introduced consecutively in a line and the mixtures stored in a container. To ensure the homogeneity of the mixture, a magnetic stirrer is placed in the vessel. The gases are of Standard quality (SQ) (Air Liquide). Next, a small quantity of gas is removed via the valves V1, V2 and V7 and then passes to the chromatograph for analysis of the composition.

The mixture thus prepared can be injected into the gas metering system through valves D1 and D2. Pressures below 10 bar are detected by the gauge P14 (Mensor brand with a full scale sensitivity of 0.01%), whereas at higher pressures, P1 is automatically closed to protect the gauge. Once in the metering system, the mixture is introduced into the gravimetric system. During the equilibration, the gas can be transported around the metering system and for this purpose the two circulators using a piston effect and an electromagnetic control. The metering system can operate up to 50 bars. At each equilibrium point, about 0.8 cm³ of gas can be removed and again sent to the chromatograph. Finally, the two valves M1 and M2 allow a supplementary option of sending the gas towards a second instrument containing the same sample, such as for example a microcalorimeter.

The gravimetric measurement system was purchased from Rubotherm Präzisionsmeßtechnik GmbH. This system has previously been described [De Weireld et al., ref. 38, Dreisbach et al., ref. 39]. In the present case, the equilibrium time was considered satisfactory when the sample weight does not vary by more than 80 mg over a period of 5 minutes. At each equilibrium point, the sample and charge weights are both recorded before extraction in the direction of the chromatograph. The temperature of the experiment was maintained constant by means of a cryo-thermostat with a precision of 0.01 K.

The degassing system uses the method named "Sample Controlled Thermal Analysis (SCTA)" making it possible to degas the solid in situ up to a defined temperature (T<620 K) and pressure (0.02 mbar) for 16 hours [Sorensen et al., ref. 40].

The gas phase chromatograph is of the Agilent 3000, micro-cpg brand. The carrier gas here was helium. At each equilibrium point, the extracted gas is introduced into a volume of 1 cm³ then passed to the chromatograph. The program Cerity made it possible to control the system and to calibrate and analyze the results.

In this study, the experiments were performed at 303K and up to P=30 bar. For each point, it was possible to measure $m^{tot}$, the total quantity adsorbed $n^{tot}$, the total pressure $p^{tot}$ and the density of the gaseous phase.

Experimental Description for the Infrared Experiments of Examples 6, 11 and 14

Preparation of the Sample

The samples are compressed in the form of self-supporting disks. The disk has a diameter of 1.6 cm and a weight of 13 to 20 milligrams. The pelletting pressure is of the order of $10^9$ Pa.

Equipment Used

The pelleted sample is placed in an infrared cell designed in the laboratory. The cell can be of metal for studies under a current of gas (the description of the cell is given in the following article T. Lesage, C. Verrier, P. Bazin, J. Saussey, M. Daturi, Phys. Chem. Chem. Phys. 5 (2003) 4435) or in quartz for studies under vacuum or at gas pressures lower than atmospheric pressure.

The infrared spectra are recorded by means of a Fourier transform infrared spectrometer of Nexus® or Magna-550® brand manufactured by Thermo Fisher Scientific. The spectrometer is fitted with an infrared detector of the MCT/A type. The infrared spectra are recorded at a resolution of 4 cm$^{-1}$.

Gases Used

The gases used for the infrared experiments are of high purity:

Carbon monoxide: supplier alphagaz type N47 purity (>99.997%)

Nitrogen monoxide: supplier Air Liquide, France purity >99.9%

Helium, nitrogen, argon: supplier air liquide, purity >99.9%

All the gases are dried beforehand over molecular sieve and/or by cryogenic trapping using liquid nitrogen. The nitrogen monoxide is purified by distillation.

Example 6

Propane and Propylene Adsorption Isotherms

Figures 10A, 10B:
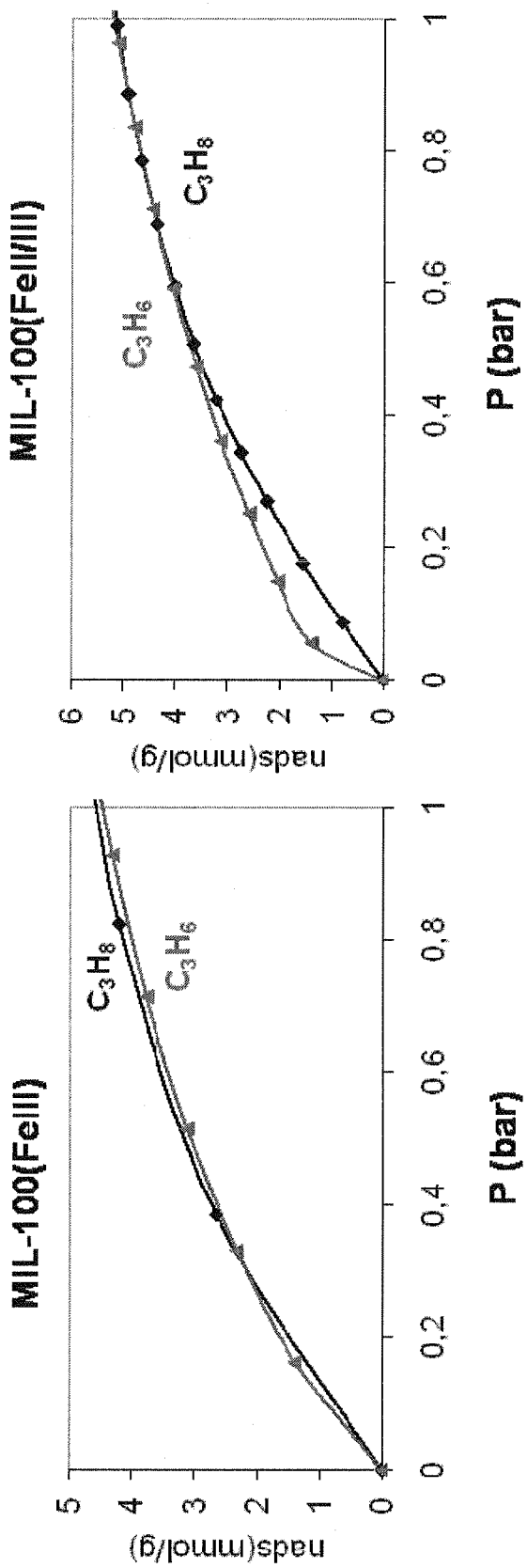
FIG. 10A shows propane/propylene adsorption isotherms at 303 K with the MIL-100(Fe) activated at 120° C. (iron (III)).
FIG. 10B shows propane/propylene adsorption isotherms at 303 K with the MIL-100(Fe) activated at 260° C. (Iron(II)/Iron(III)).

Measurements of propane and propylene adsorption were performed at thermodynamic equilibrium (FIG. 10) at ambient temperature from 1 g of MIL-100(Fe) solid. An initial measurement was first performed on the solid activated at 120° C. under primary vacuum (P=1 Pa for 16 hours) followed by a second measurement on the same solid but activated at higher temperature (260° C. under primary vacuum (P=1 Pa for 16 hours). IR spectroscopy showed (example 5) that the activation of this solid at 120° C. under vacuum (or in a current of helium) results in a solid containing only iron at the oxidation level +III whereas activation at 260° C. under vacuum (or in a current of helium) results in a solid containing both iron(III) and iron(II) (Fe(II)/Iron(III) proportion about 20%). In the absence of reduction of the iron (activation at 120° C.), there is no difference in the adsorption isotherms for propane and propylene whereas the partially reduced solid (activation at 260° C.) exhibits a significant difference in adsorption at low levels of recovery (P<0.4 bar) with a markedly greater quantity of propylene adsorbed, which indicates a greater affinity of the iron(II) for propylene.

Example 7

Separation Tests

Figure 11:
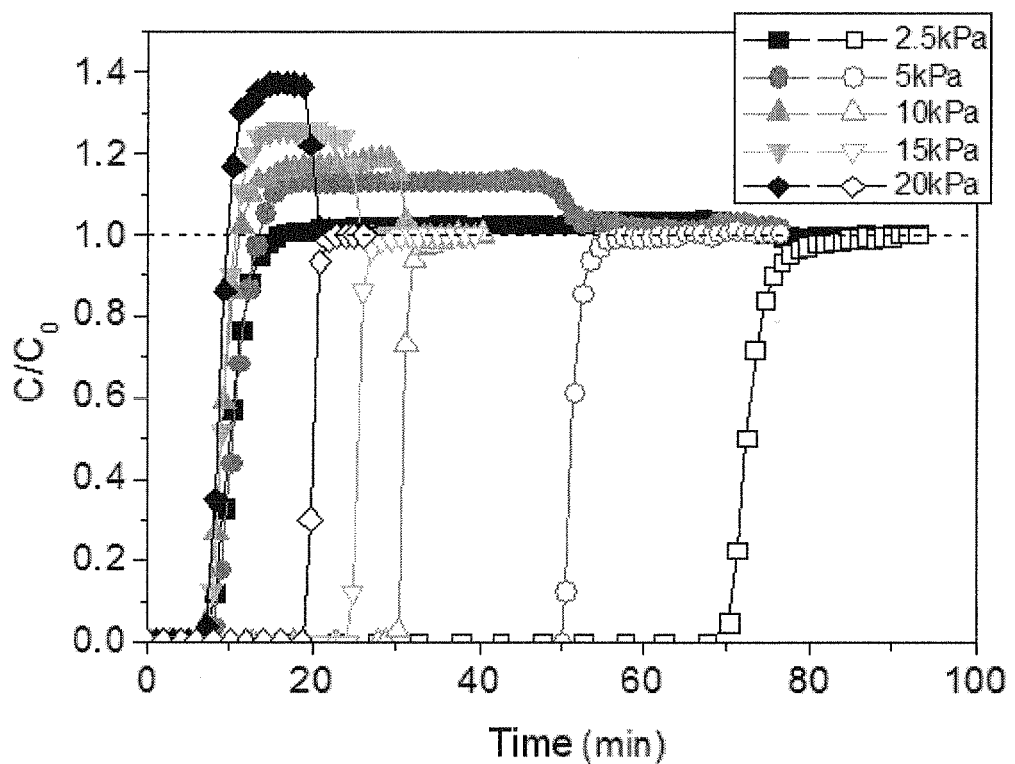
FIG. 11 shows breakthrough curves at 2.5, 5, 10, 15 and 20 kPa of 50/50 mixtures of propane and propylene at 40° C. with the MIL-100(Fe) solid pretreated with NH$_4$F, and activated at 250° C. under helium (3 hours): effect of the partial pressure on the propane/propylene separation (open: propylene, solid: propane).

Dynamic separation tests (current of helium, % propane=% propylene=3.7 mol %) from a 50/50 propane/propylene mixture were then performed on columns (dimensions: 2 meters 0.3125 cm ($1/8^{th}$ of an inch)) packed with 1 gram of MIL-100(Fe) solid previously activated in a current of helium at 280° C. (P=100000 Pa, 16 hours) at different total pressures (1, 3 and 5 bars) (FIG. 11).

There is a very clear differentiation between the behavior of propane and propylene. Propane is practically not retained in the column in view of its low retention time, while the retention times of propylene are much higher. In addition, the difference in retention time between the two gases is maintained when the pressure increases, which indicates that the apparent selectivity is maintained in this pressure range.

Example 8

Influence of the Temperature at Thermodynamic Equilibrium

Figure 12:
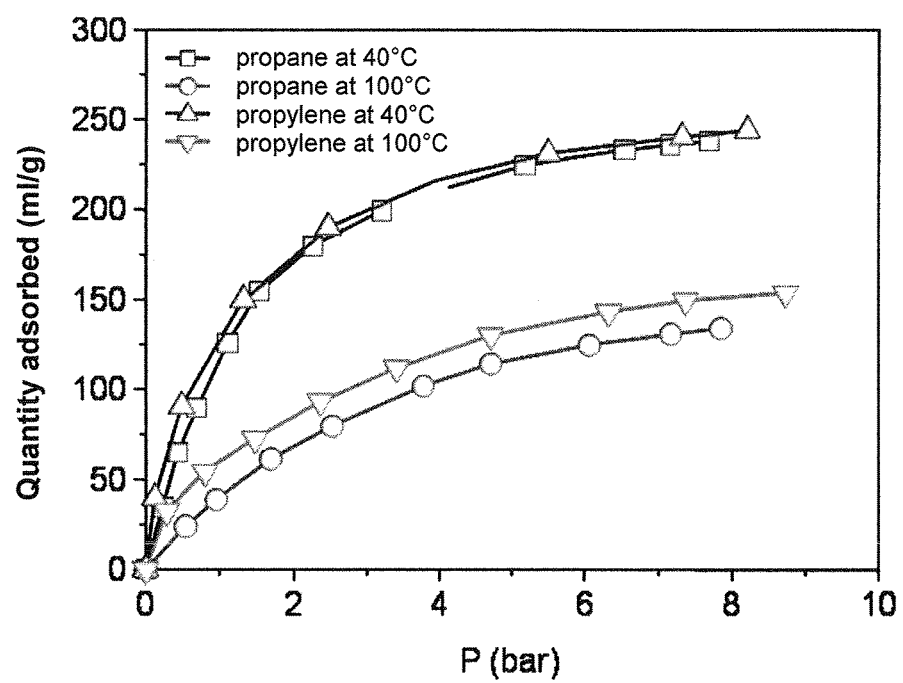
FIG. 12 shows adsorption isotherms of propane and propylene at 40° C. and 100° C. in the MIL-100(Fe) solid activated at 250° C. under vacuum.

Measurements of propane and propylene adsorption (current of helium, % propane=% propylene=3.7 mol %) at two different temperatures (40 and 100° C.) were performed at thermodynamic equilibrium (FIG. 10) on the MIL-100(Fe) solid activated at 250° C. under primary vacuum (P=1 Pa for 16 hours) (FIG. 12).

Example 9

Influence of the Temperature in Column Separation

Figure 13:
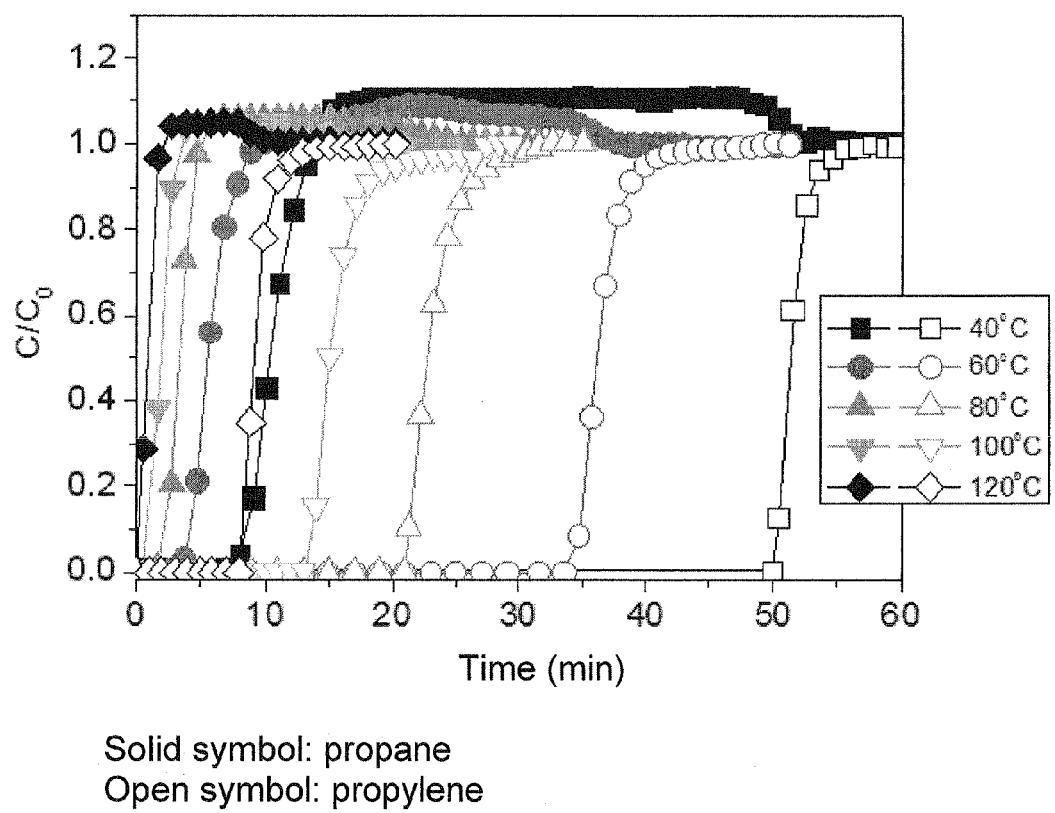
FIG. 13 shows breakthrough curves at 5 kPa of 50/50 mixtures of propane and propylene at different temperatures with the MIL-100(Fe) solid pretreated with NH$_4$F, and activated at 250° C. under helium (3 hours): propane/propylene separation as a function of the temperature (equimolar propane/propylene mixture P=5 kPa, in He) in the propane/propylene separation (open: propylene, solid: propane).

The influence of the temperature on propane/propylene separation (current of helium, % propane=% propylene=3.7 mol %) was studied in a column (dimensions: 2 meters 0.3125 cm ($1/8^{th}$ of an inch)) on one gram of MIL-100(Fe) partially reduced solid under a current of helium at 280° C. (P=10000 Pa, 16 hours) (FIG. 13). While the retention times of the two gases decrease as expected with increasing temperature, it is interesting to see the differentiation between low retention times for propane and high for propylene is maintained even at 120° C.

Example 10

Cyclability Tests

Figure 14:
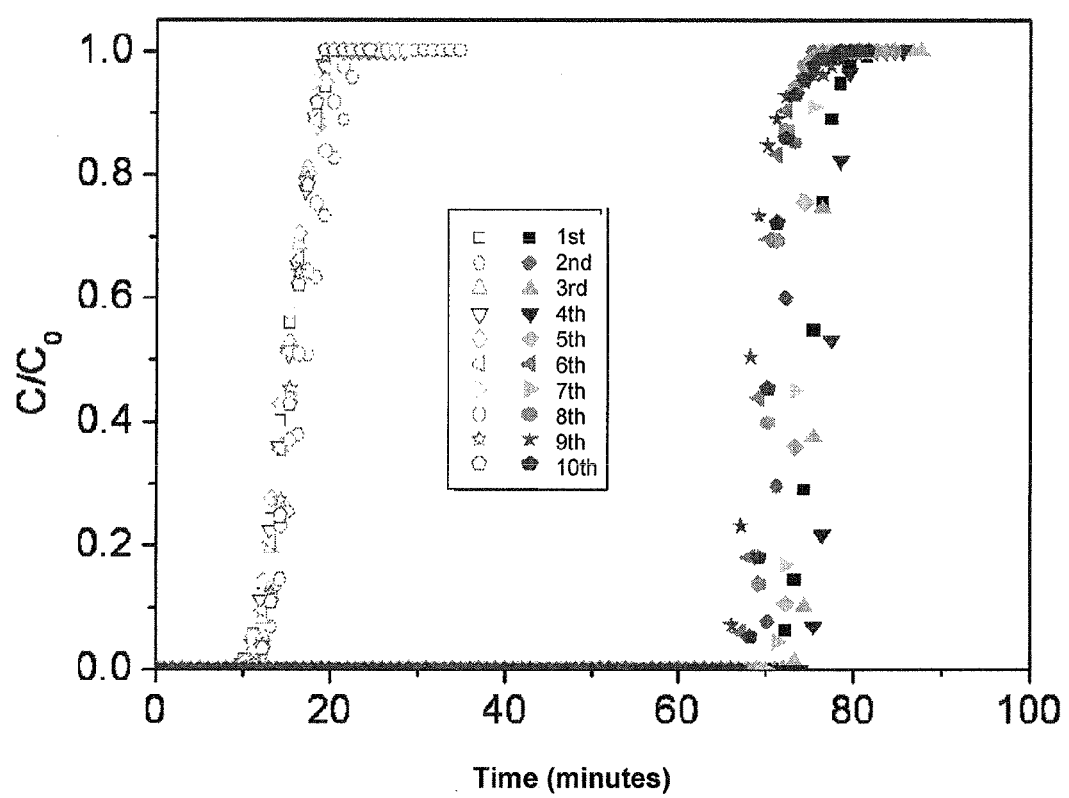
FIG. 14 shows breakthrough curve cyclability tests at 1 bar of a 50/50 mixture of propane and propylene at 298 K with the MIL-100(Fe) solid activated at 280° C. in a current of helium (open: propane, solid: propylene).

In order to check that the integrity of the MIL-100(Fe) solid is maintained after the separation tests, the dynamic separation test (current of helium, % propane=% propylene=3.7 mol %) from a 50/50 propane/propylene mixture was repeated 10 times, under the same conditions, on a column (dimensions: 2 meters*0.3125 cm ($1/8^{th}$ of an inch)) packed with 1 gram of MIL-100(Fe) solid previously activated in a current of helium at 280° C. (P=10000 Pa, 16 hours). The solid was reactivated between each experiment by passing helium at 200° C. between each adsorption cycle (P=10000 Pa, 16 hours). The breakthrough curves superimpose entirely satisfactorily (FIG. 14), which indicates very good cyclability of the adsorbent MIL-100(Fe) for propane/propylene mixtures under pressure.

Example 11

Influence of the Iron(II) Content

Figure 15:
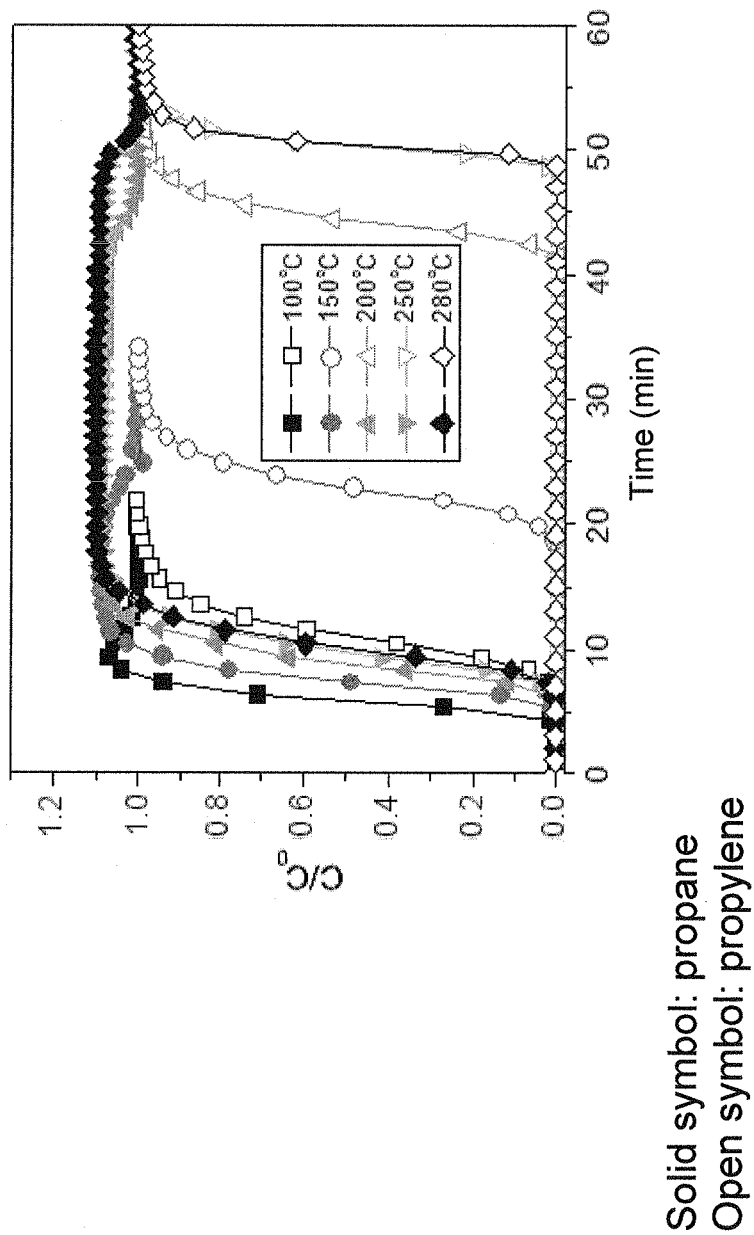
FIG. 15 shows breakthrough curves at 5 kPa of a 50/50 mixture of propane and propylene at 40° C. with the MIL-100(Fe) solid pretreated with NH$_4$F, and activated at different temperatures under helium: effect of the activation temperature under helium (3 hours) on the propane/propylene separation at 40° C. (total propane+propylene partial pressure (equimolar mixture)=5 kPa) (open: propane, solid: propylene).

The influence of the iron(II) content on the dynamic separation properties for propane/propylene mixtures (current of helium, % propane=% propylene=3.7 mol %) was tested on a column (dimensions: 2 meters*0.3125 cm ($1/8^{th}$ of an inch)) packed with 1 gram of MIL-100(Fe) solid, activated in a current of helium at different temperatures, between 100° C. and 300° C. (FIG. 15). It will be recalled that the level of iron(II) varied almost linearly with the activation temperature (under vacuum) when the latter is greater than 150° C. (cf example 5, FIG. 22).

The solid activated at 100° C., containing no or very little iron(II), does not exhibit a significant difference in the retention times of propane and propylene, which confirms the results obtained at thermodynamic equilibrium (example 6). The solid activated at higher temperature (150-280° C.) exhibits an increase of the difference between the retention times of propane and propylene with the temperature, which is consistent with an increase in the affinity of the MIL-100 (Fe) for propylene following the increase in the iron(II) content in the MIL-100(Fe) solid. The selectivity between propane and propylene varies as a function of the activation temperature of this material. Activation of the solid at 300° C. shows practically no difference between the retention times for propane and propylene and hence an absence of selectivity. X-RAY thermodiffraction under vacuum previously showed (cf FIG. 4) that the framework of MIL-100(Fe) degrades beyond an activation temperature of 280° C. (primary vacuum), which explains the absence of adsorption under these conditions.

Example 12

Regeneration

Figure 16:
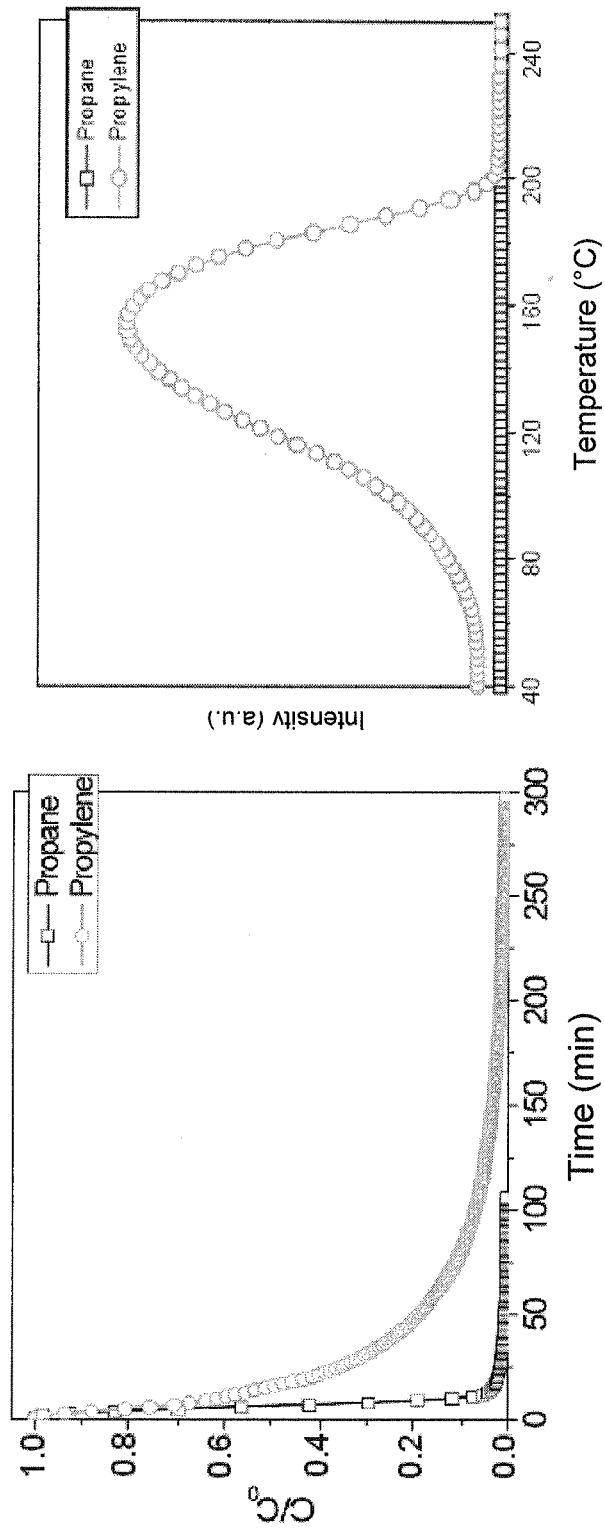
FIG. 16 shows the thermodesorption of propane/propylene in the MIL-100(Fe) solid pretreated with NH$_4$F, and a) activated at 250° C. under helium (3 hours) or b) under secondary vacuum for 12 hours (partial pressure equimolar propane/propylene mixture in He=5 kPa)

The regeneration of the MIL-100(Fe) solid, activated at 280° C. in a current of helium, after adsorption of the propane/propylene mixture (current of helium, % propane=% propylene=3.7 mol %) on a column (dimensions: 2 meters*0.3125 cm ($1/8^{th}$ of an inch)) was studied by thermodesorption. The propane, present in very small quantity, is desorbed at low temperature (<100° C.). The propylene, the more strongly adsorbed species, is liberated between 70 and 200° C. (FIG. 16), which confirms a stronger interaction between the partially reduced MIL-100(Fe) and the propylene.

Example 13

Pulse Separation of Mixtures of Gaseous Hydrocarbons

Figure 17:
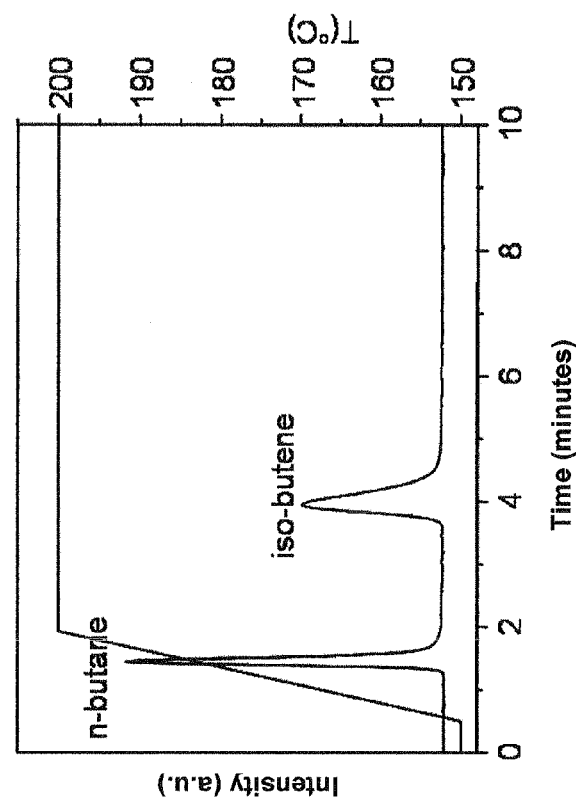
FIG. 17 shows the separation of pulses of 50/50 mixtures of alkanes and alkenes (1% by weight in a current of nitrogen) at 298 K on MIL-100(Fe) activated at 280° C.
Figure 17:
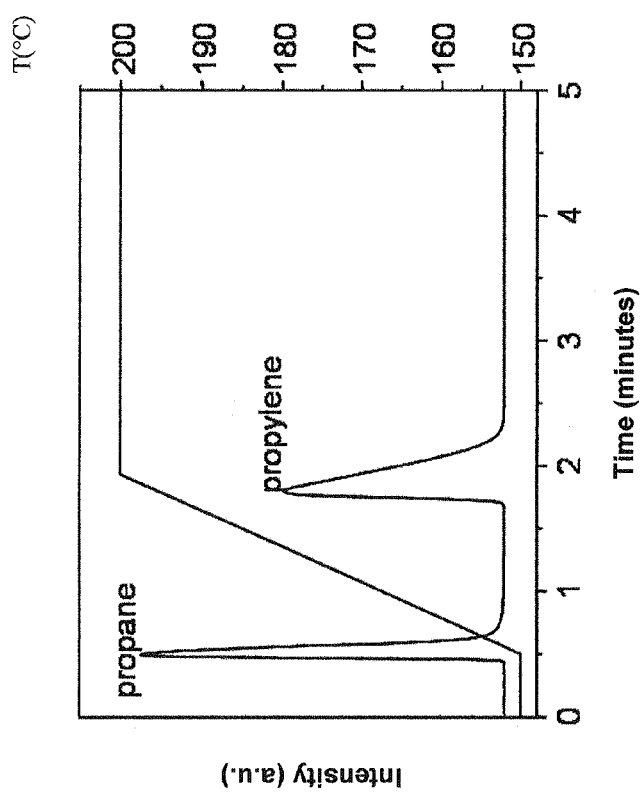
Figure 18:
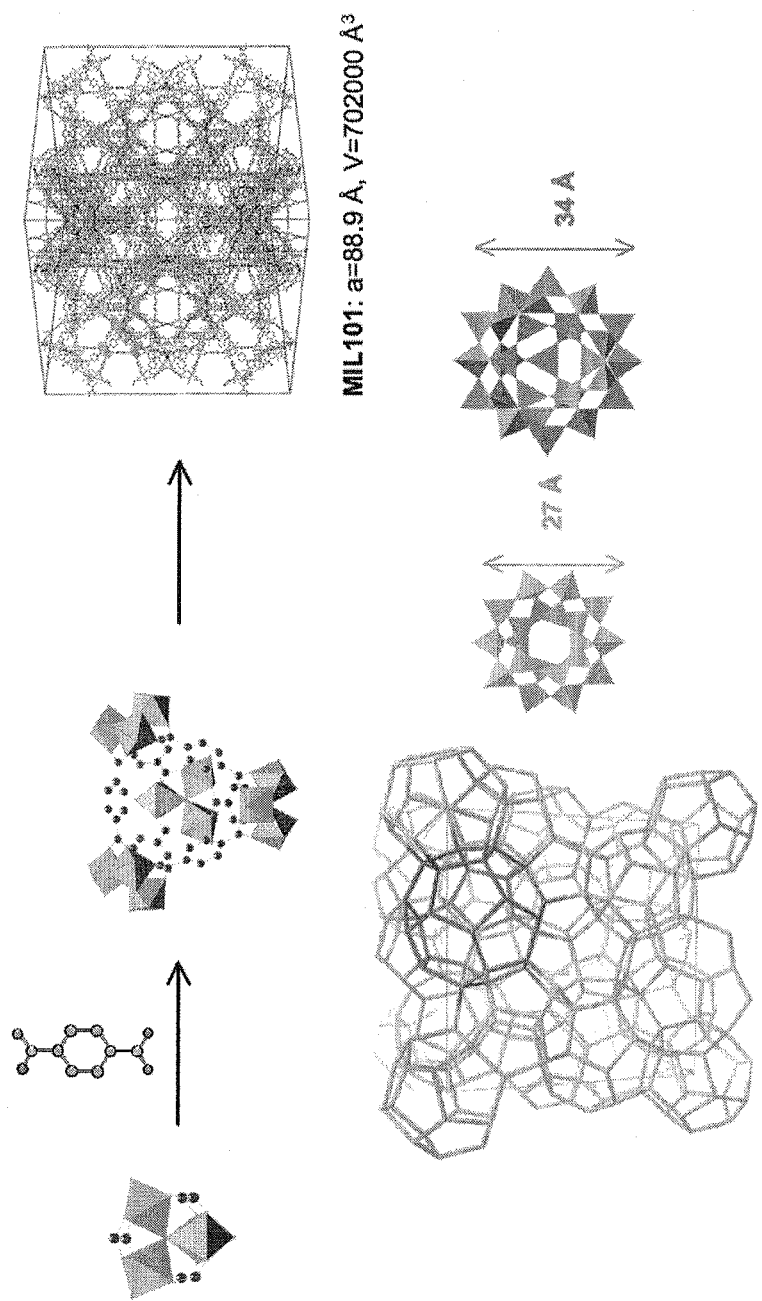
FIG. 18 shows the structure of the MIL-100(Fe) solid. (a): trimer of octahedron and trimesic ligand, (b): supertetrahedron, (c): schematic 3d structure, (d): the two types of mesoporous cage.

50/50 propane/propylene and 50/50 n-butane/iso-butene mixtures in a carrier gas (1% by weight in nitrogen) were introduced in the form of a pulse at ambient temperature into a column (dimensions: 2 meters*0.3125 cm ($1/8^{th}$ of an inch)) packed with 1 gram of MIL-100(Fe) solid previously reduced in a current of helium at 280° C. (P=10000 Pa, duration: 16 hours). The proportion of each gas was analyzed by gas chromatography on emergence from the column. For these two mixtures, it appears that the alkanes exhibit lower retention times than the alkenes with a difference which increases with the size of the olefin (FIG. 17). In fact, the n-butane/iso-butene mixture (pulsed) is separated in the same way as the propane/propylene mixture, but with higher retention times, consistently with the stronger interactions typically generated by a hydrocarbon with four carbons compared to a hydrocarbon with three carbons [ref. 43: (a) Denayer, J. F. M., De Meyer, K., Martens, J. A., Baron, G. V. *Angew. Chem., Int. Ed.* 2003, 42, 2774-2777. (b) Denayer, J. F. M., Ocakoglu, R. A., Arik, I. C., Kirschhock, C. E. A., Martens, J. A., Baron, G. V. *Angew. Chem., Int. Ed.* 2005, 44, 400-403].

Further, the relative quantity of propane and propene adsorbed in the MIL-100(Fe) solid was determined as a function of the activation temperature of this solid (same conditions, in a current of helium, P=10000 Pa, 16 hours) (FIG. 15). It can clearly be seen that the relative proportion of propene to propane increases as a function of the temperature, between 100 and 280° C., with a maximum of propene retained in the solid when the activation temperature is 280° C., and at 300° C., consistently with a destruction of the framework, the solid almost no longer adsorbs propane and propene.

Example 14

Low Brønsted Acidity

Figure 28:
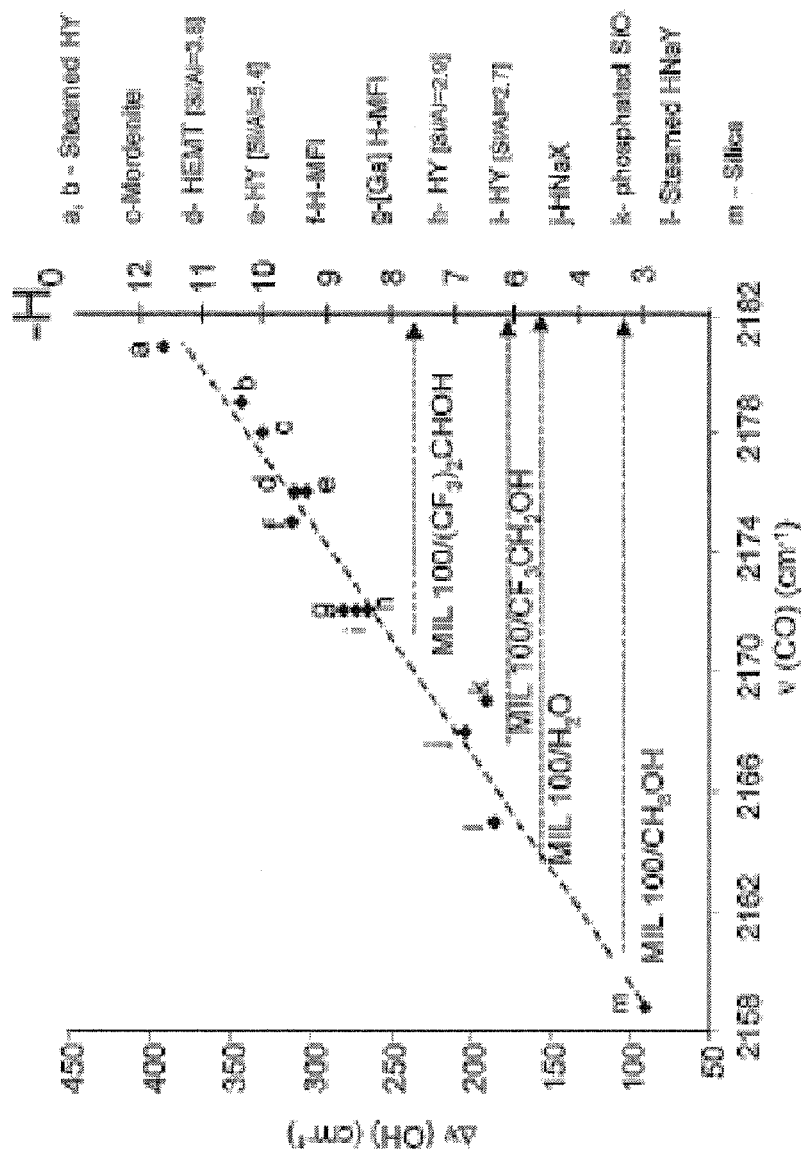
FIG. 28 shows a graph of the Brønsted acid strength of the OH groups of different species grafted on a MIL-100(Cr) sample analyzed by IR after adsorption of CO: correlation between the v(OH) displacement, the values of $H^0$ and the v(CO) position.

Previous studies on a MIL-100(Cr) system showed the presence of a large number of Lewis acid sites (Vimont et al., ref. 35 (a)) which are transformed into Brønsted acid sites by adsorption of water. The addition of small calibrated doses of CO confirmed the existence of two types of water molecule of similar acid strength, overall rather weak. The introduction of alcohols of different basicity established that the strength of the Brønsted acid sites depends on the nature of the coordinated molecule and increases with the basicity of the protic species (FIG. 28).

Complementary studies have shown that the MIL-100(Fe) solid is a little less acidic (Brønsted acidity) than the MIL-100(Cr) solid (cf. Vimont et al. ref. 35(b)).

Thus, although the MIL-100 solid possesses unsaturated metal centers (iron, vanadium) which are Lewis acid centers, even if these can be transformed into Brønsted acidity by coordination of proton donor molecules such as water (Vimont et al., ref. 35 (b)), the acidity measured by CO adsorption in the homologous MOF material MIL-100(Cr) not being very strong, it is expected that the same is the case for MIL-100(Fe). This Brønsted acidity is not sufficient to trigger or provoke any polymerization of unsaturated hydrocarbons (for example propylene) in the pores of the MOF material. Tests of non-polymerization of propene as a function of the temperature confirm the absence of polymerization for temperatures lower than 200° C.

Example 15

Acetylene/Ethylene Separation

Figure 34:
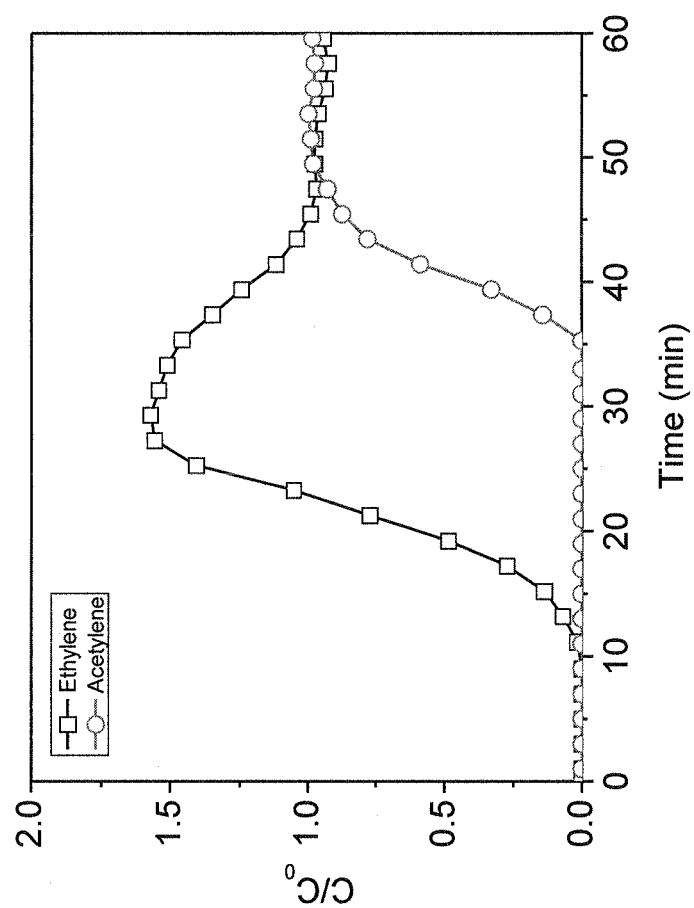
FIG. 34 shows the breakthrough curves at 1 bar and 40° C. of a 50/50 mixture of acetylene and ethylene with the MIL-100(Fe) solid activated at 270° C. in a current of helium.

At the start of the separation (time <20 minutes) it is observed that the acetylene emerges from the column later than the ethylene, which indicates greater retention of the alkyne compared to the alkene (FIG. 34). At longer times (t>20 minutes), the two species are retained in the same way indicating competitive adsorption.

To understand the difference in behavior between acetylene and ethylene, a thermodesorption experiment (desorption as a function of the temperature) was performed (FIG. 35) taking the MIL-100(Fe) solid after passage of the acetylene/ethylene gas mixture under the conditions defined above.

Example 16

Acetylene/Ethylene Thermodesorption Curve

Figure 35:
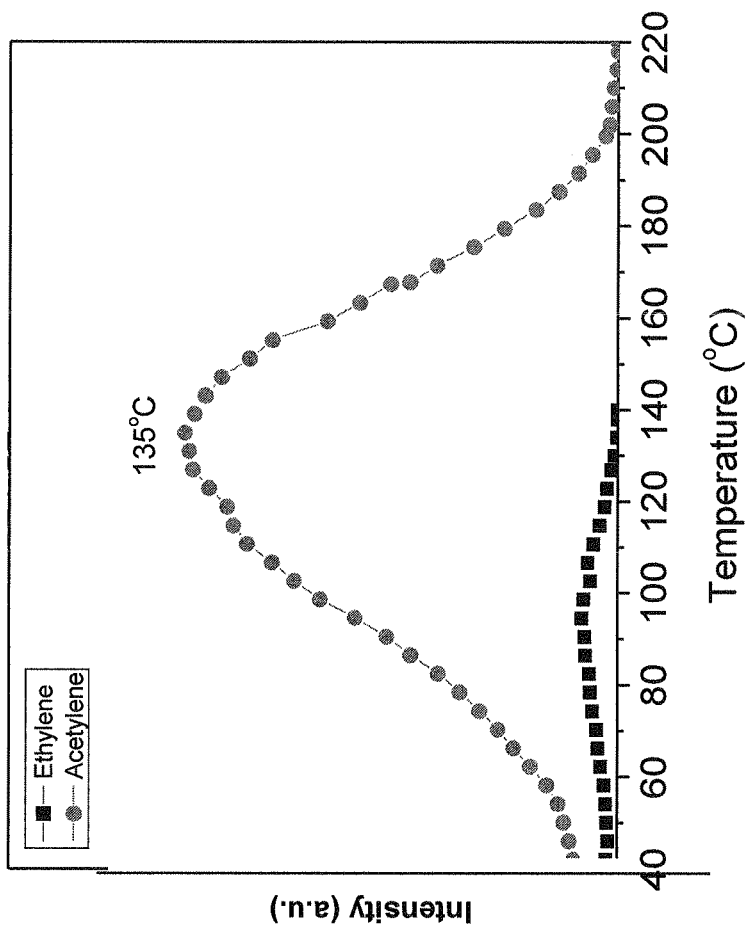
FIG. 35 shows a thermodesorption curve of an acetylene/ethylene mixture from the MIL-100(Fe) solid activated at 270° in a current of helium and subjected to 1 bar of acetylene and ethylene in 50/50 proportion at 40° C.

Here we observe that a considerable part of the acetylene adsorbed in the MIL-100(Fe) leaves the material at higher temperatures than the ethylene, even though a non-negligible proportion of the acetylene is desorbed at the same time as the majority of the ethylene (FIG. 35). This indicates heterogeneity of the adsorption sites. Doubtless the strong adsorption sites interact by retrodonation effect on the alkyne and correspond to the unsaturated Fe(II) sites and the Lewis acid sites, Fe(III), adsorb the alkene and the alkyne with the same strength of interaction.

Example 18

Acetylene/Ethylene Separation

The experiment of example 15 was repeated using different experimental conditions: namely 0.5 g of MIL-100(Fe) solid in a tube of diameter 3/8" (instead of 0.15 g in a 1/8" tube) (FIG. 34).

At the start of separation (time <35 minutes) it is observed that the acetylene emerges from the column later than the ethylene, which indicates very high retention of the alkyne compared to the alkene. At longer times (t>40 minutes), the two species are retained in the same way indicating competitive adsorption (FIG. 34).

Example 19

Acetylene/Ethylene Thermodesorption Curve

To understand the difference in behavior between acetylene and ethylene, a thermodesorption experiment (desorption as a function of the temperature) was performed taking the MIL-100(Fe) solid after passage of the acetylene/ethylene gas mixture under the conditions defined above (FIG. 35).

FIG. 35 indicates that a very considerable part of the acetylene adsorbed in the MIL-100(Fe) leaves the material at temperatures greater than the ethylene (T=40-200° C. with a desorption maximum at 135° C.), whereas the small proportion of acetylene initially adsorbed is desorbed at lower temperature (T=40-140° C. with a desorption maximum at 90° C.). This simultaneously indicates good acetylene/ethylene selectivity but also heterogeneity of the adsorption sites. Doubtless the strong adsorption sites interact by retrodonation effect on the alkyne and correspond to the unsaturated Fe(II) sites and the Lewis acid sites, Fe(III), adsorb the alkene and the alkyne with less good selectivity.

Example 17

Pulse Separation of Gaseous Mixtures of C4 Hydrocarbons

Figure 36:
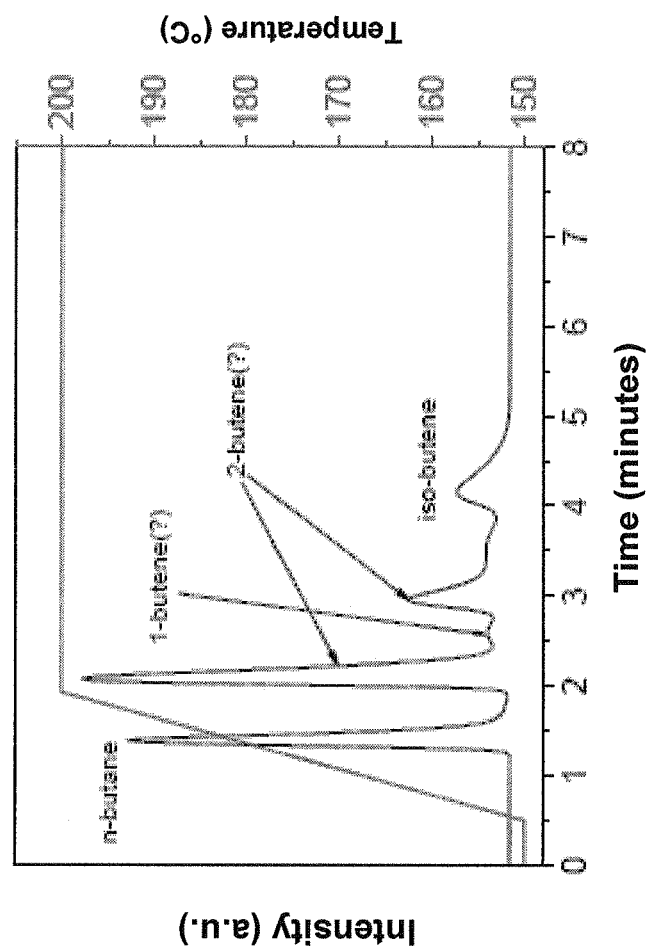
FIG. 36 shows a pulse separation of mixtures of C4 isomers (40° C.)

50/50 propane/propylene and 50/50 n-butane/iso-butene mixtures in a carrier gas (1% by weight in nitrogen) were introduced in the form of a pulse at ambient temperature into a column (dimensions: 2 meters 0.3125 cm ($\frac{1}{8}^{th}$ of an inch)) packed with 2.2 gram of MIL-100(Fe) solid previously dehydrated and reduced in a current of helium at 280° C. (P=10000 Pa, duration: 16 hours). The proportion of each gas was analyzed by gas chromatography on emergence from the column. For this mixture, it appears that not only is the alkane (butane) the species least retained in the column but that it is also possible to separate the different isomers of butene, with significant differences in retention time (FIG. 36).

Example 18

Adsorption isotherms of CO and $CO_2$

Measurements of CO and $CO_2$ adsorption were performed at thermodynamic equilibrium (FIG. 37) at ambient temperature from 1 g of MIL-100(Fe) solid. An initial measurement was first performed on the solid activated at 100° C. under primary vacuum (P=1 Pa for 16 hours) followed by a second measurement on the same solid but activated at higher temperature (260° C. under primary vacuum (P=1 Pa for 16 hours). In the absence of reduction of the iron (activation at 100° C.), the quantities of $CO_2$ adsorbed are much greater than those of CO whereas the partially reduced solid (activation at 260° C.) exhibits a very considerable increase in the quantity of CO, and a smaller increase in that of $CO_2$. At low pressure (P<0.2 bar), the quantity of CO adsorbed is even greater than or equal to that of $CO_2$.

Example 19

Selectivity as a Function of the Activation Temperature of the MIL-100(Fe)

Figure 38:
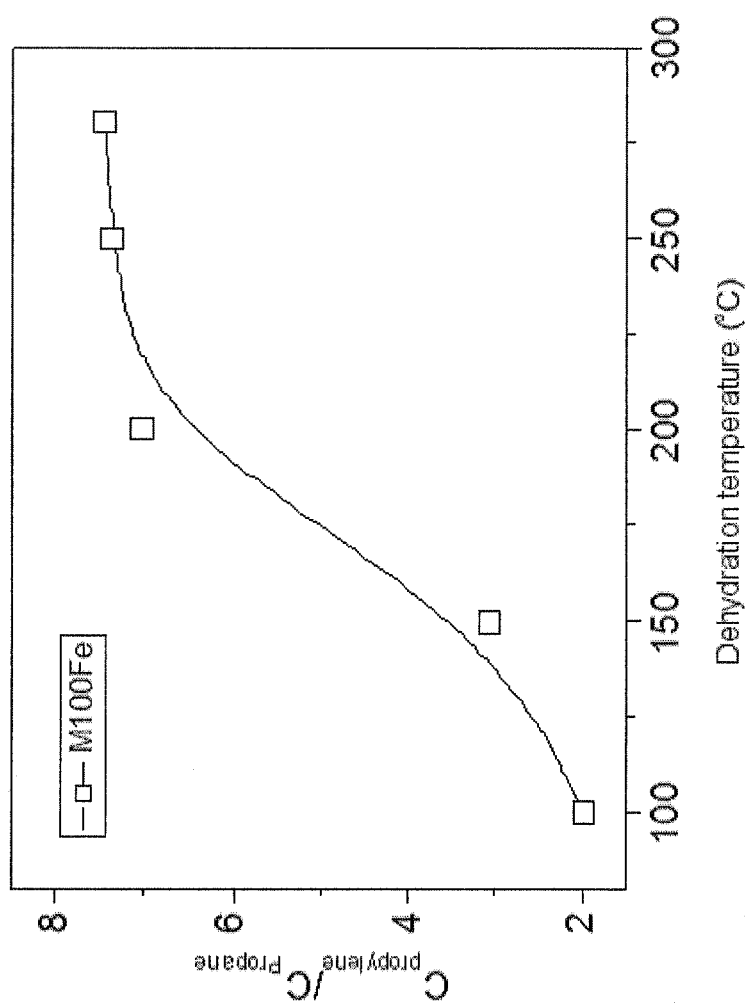
FIG. 38 shows the propylene/propane selectivity as a function of the activation temperature under helium of the MIL-100(Fe) solid pretreated with NH$_4$F: effect of the activation temperature under helium on the propane/propylene separation at 40° C. (total propane+propylene partial pressure (equimolar mixture)=5 kPa)
Figure 39:
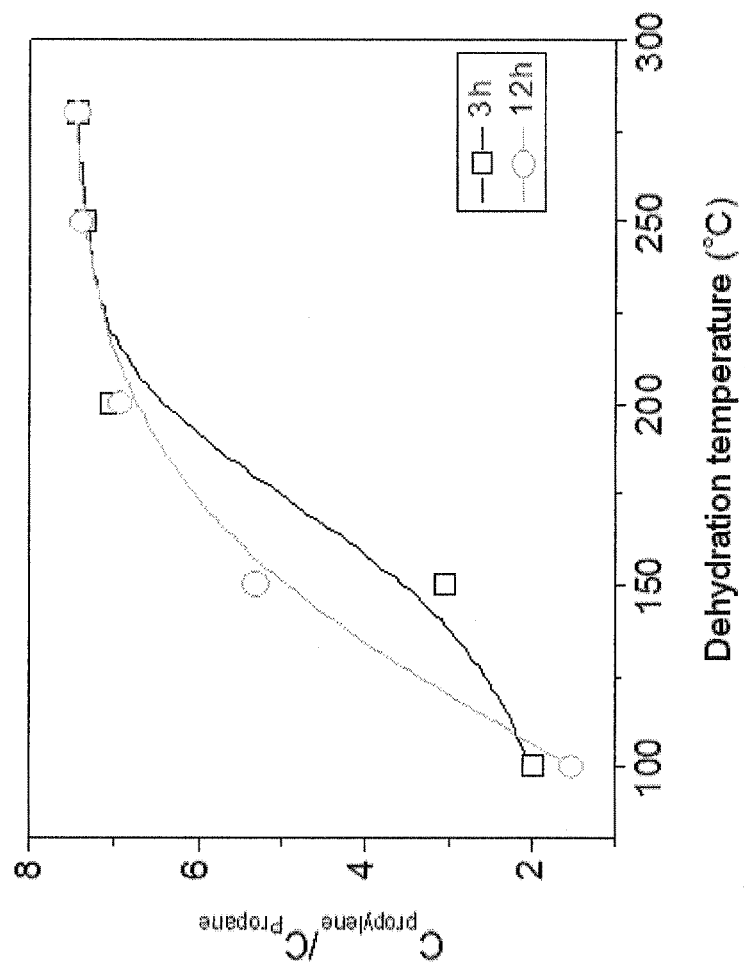
FIG. 39 shows the effect of the activation time at variable temperature (100-250° C.) under helium on the propane/propylene separation at 40° C. on the MIL-100(Fe) solid pretreated with NH$_4$F: (total propane+propylene partial pressure (equimolar mixture)=5 kPa)
Figure 40:
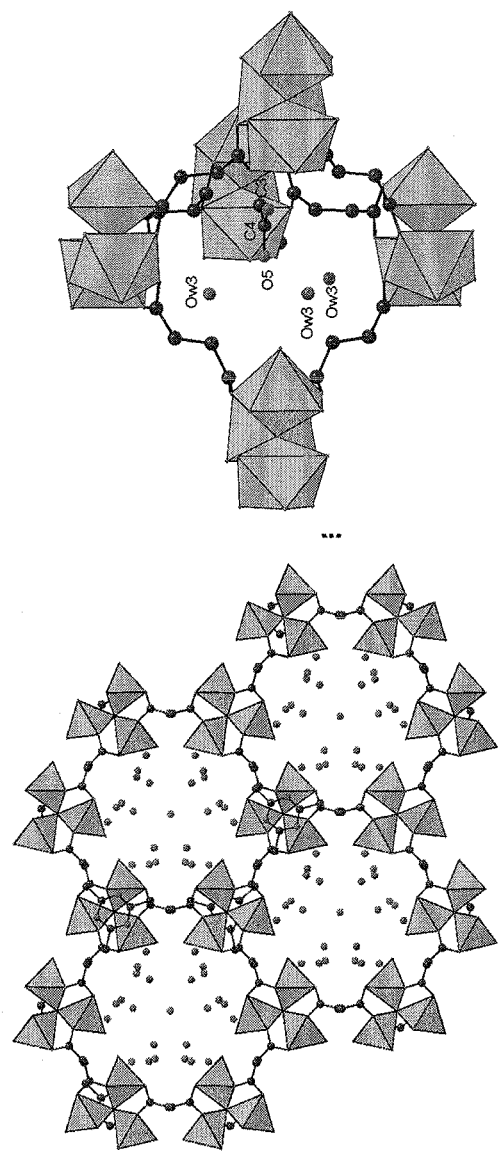
FIG. 40 shows the structure of the iron carboxylate MIL-88A (hydrated). Left: view along the axis of the tunnels (axis c), right: view along the axis perpendicular to the tunnels (axe b, similar view along the axis a). The iron octahedra, the carbon atoms and the molecules of water are in green, black and red respectively.
Figure 41:
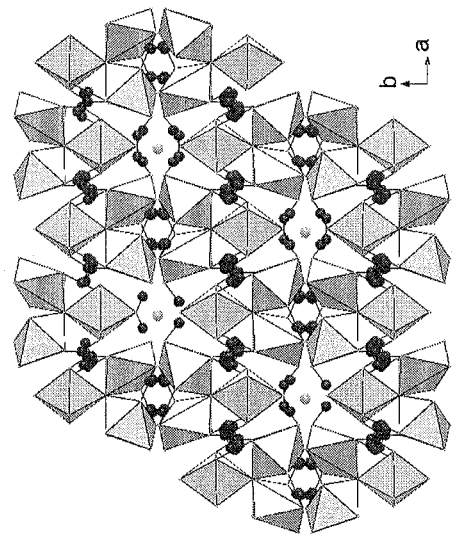
FIG. 41 shows the structure of the iron carboxylate MIL-89(Fe). Left: view along the axis of the tunnels (axis c), right: view along the axis perpendicular to the tunnels (axis b, similar view along the axis a). The atoms of iron and carbon and the molecules of water are in grey, black and white respectively.
Figure 41:
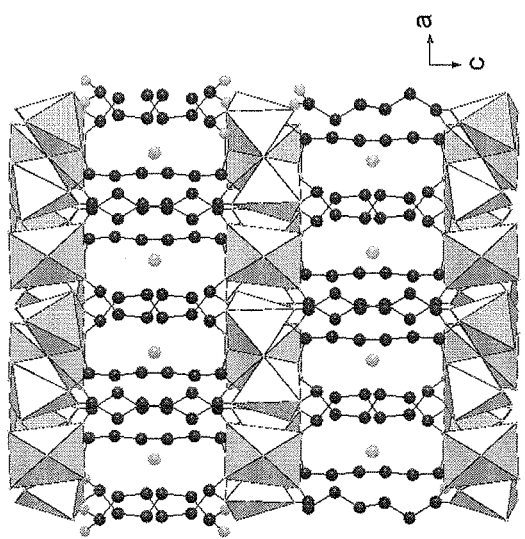

On the basis of the results of the dynamic separation tests, (current of helium, % propane=% propylene=3.7 mol %) with a 50/50 propane/propylene mixture on a column (2 meters*0.3125 cm ($\frac{1}{8}^{th}$ of an inch)) and 1 gram of MIL-100 (Fe) activated in a current of helium at different temperatures ° C., calculations of selectivity were performed (FIG. 38).

The calculation was made on the basis of from the quantities of gases desorbed during thermodesorption experiments. Assuming that these two gases behave as ideal gases, the selectivity is the ratio of the molar quantity of propylene/total quantity of propane and propylene in moles (reference 46: Newalkar, B. L., Choudary, N. V., Turaga, U. T., Vijayalakshimi, R. P., Kumar, P., Komarneni, S., Bhat, S. G. T. Chem. Mater. 2003, 15, 1474).

The propene content and the selectivity (ratio of propene/propane adsorbed) increases between 1 and 4.8 with the activation temperature, with a maximum at 280° C. (FIG. 38). Above this, the material degrades and is no longer selective at all.

Example 20

"Pre-Activation" of the MOF MIL-100(Fe) Solid by Prior Treatment with $Nh_4F$ The MOF MIL-100(Fe) solid is prepared according to example 1)a).

The solid is dispersed in a 1 mol/l solution of aqueous solution of $NH_4F$ at 70° C. for 24 hours and immediately filtered hot and washed with hot water. The solid is finally dried for one night at 100° C. in an oven.

This mode of "pre-activation" is applicable to all of the MOF solids described in the present application.

The solid is then subjected to the usual activation step, for example by heating at 250° C. for 3 to 12 hours under secondary vacuum.

The properties and separation performance of the MOF MIL-100(Fe) solid previously treated with $NH_4F$ were studied (FIGS. 57 to 67).

Figure 57:
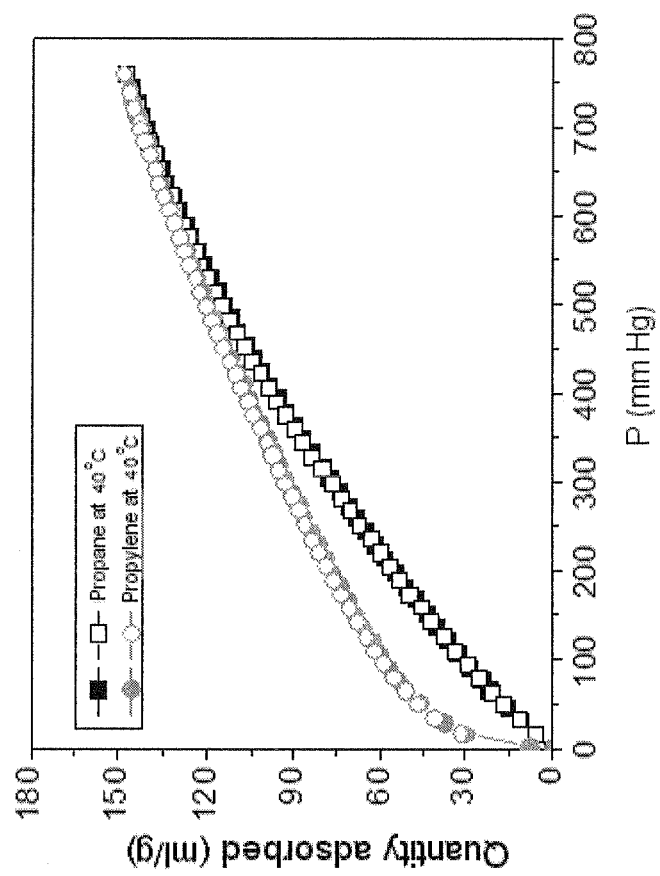
FIG. 57 shows propane/propylene adsorption isotherms at 40° C. from the MIL-100(Fe) solid pretreated with NH$_4$F ($S_{BET}$=2340 m$^2$/g)

The propane/propylene adsorption isotherms at 40° C. from the MIL-100(Fe) solid pretreated with $NH_4F$ are given in FIG. 57. The solid was activated for 12 hours at 250° C. under secondary vacuum and has a specific surface area $S_{BET}$=2340 m$^2$/g.

Figure 58:
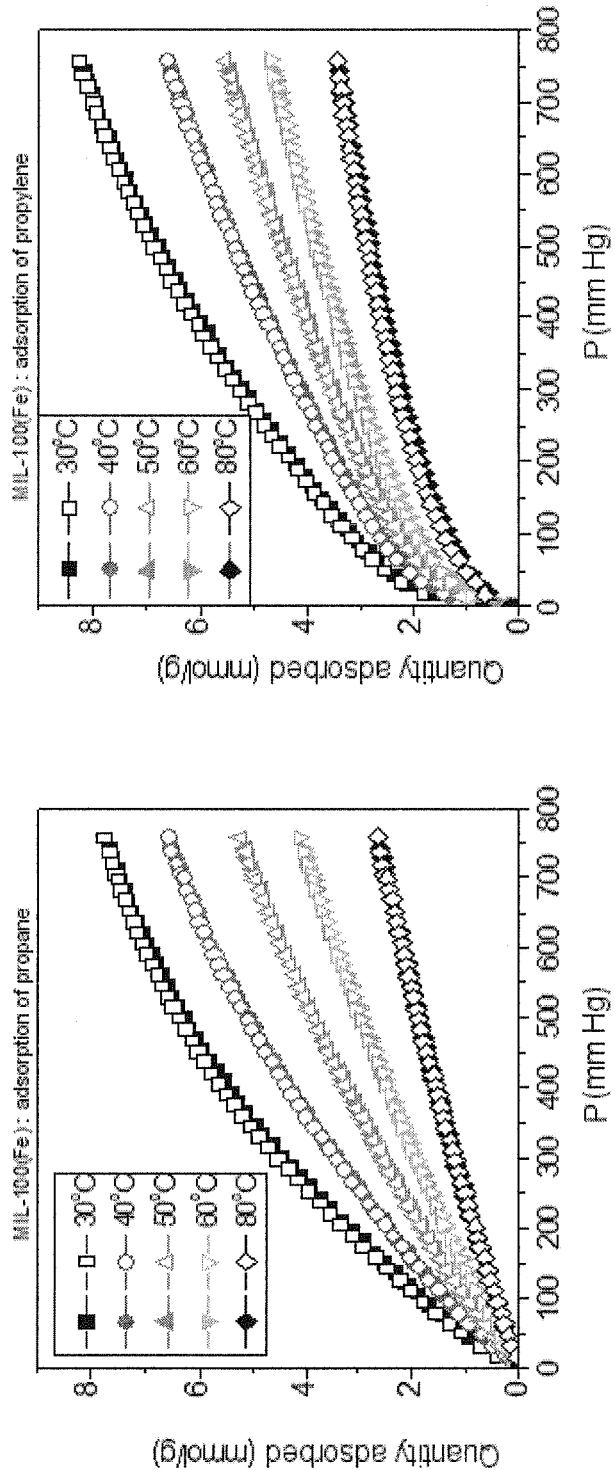
FIG. 58 shows the effect of the temperature on the propane/propylene adsorption isotherms on a MIL-100(Fe) solid pretreated with NH$_4$F, activated at 250° C. under secondary vacuum (12 hours).

FIG. 58 shows the propane (figure on left) and propylene (figure on right) adsorption isotherms at different temperatures. This relates to MIL-100(Fe) pretreated with $NH_4F$ activated at 250° C. under secondary vacuum (12 hours).

Figure 59:
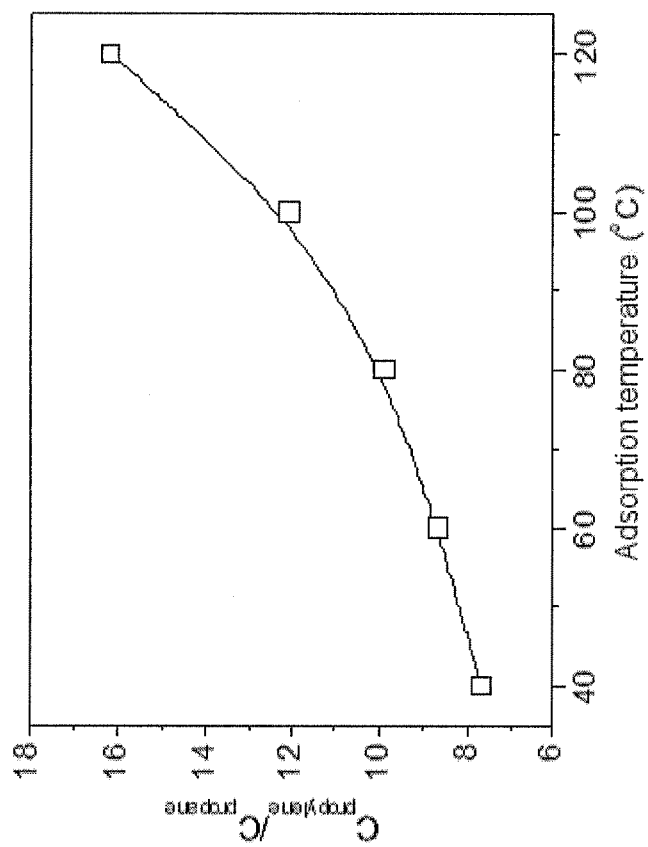
FIG. 59 shows a study of the selectivity of the propane/propylene separation as a function of the temperature, equimolar propane/propylene mixture, in He, on the propane/propylene separation at P(partial)=5 kPa on the MIL-100(Fe) solid pretreated with NH$_4$F, activated at 250° C. under helium (3 hours).

FIG. 59 shows the selectivity of the propane/propylene separation, at P(partial)=5 kPa, as a function of the temperature, for an equimolar propane/propylene mixture in a current of helium on the MIL-100(Fe) pretreated with $NH_4F$, activated at 250° C. under helium (3 hours). It is observed that at fixed partial pressure of 5 kPa, the selectivity increases as a function of the temperature and passes from about 7.8 at 40° C. to 16.2 at 120° C.

Figure 60:
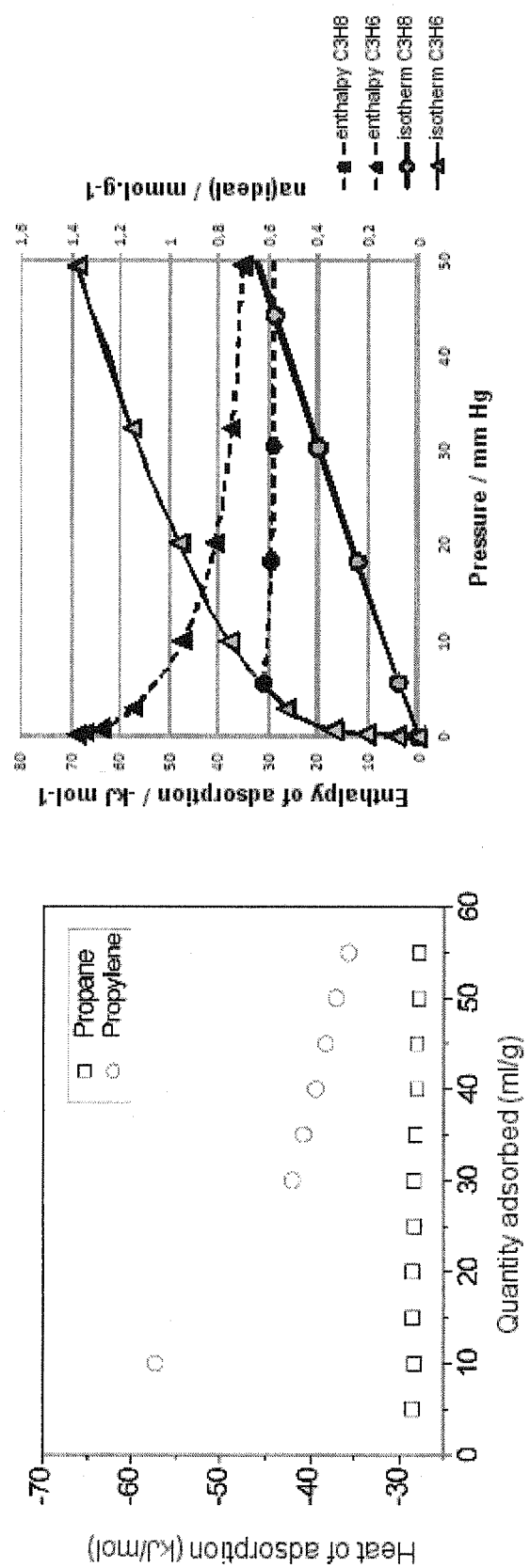
FIG. 60 shows calculations of propane/propylene heats of adsorption (deduced from the pure substance adsorption isotherms (cf FIG. 59)) on the MIL-100(Fe) solid pretreated with NH$_4$F, activated at 250° C. under secondary vacuum (12 hours)

FIG. 60 shows the heats of adsorption of propane and propylene for the MIL-100(Fe) solid pretreated with NH4F, and degassed 12 hrs at 250° C. under secondary vacuum. Figure on left: values calculated from the FIG. 58 isotherms (Clausius Clapeyron method), figure on right: Adsorption isotherms and heats of adsorption of propane and propylene at 303K in the MIL-100(Fe) solid after activation at 250° C. under secondary vacuum for 12 hours.

Figure 61:
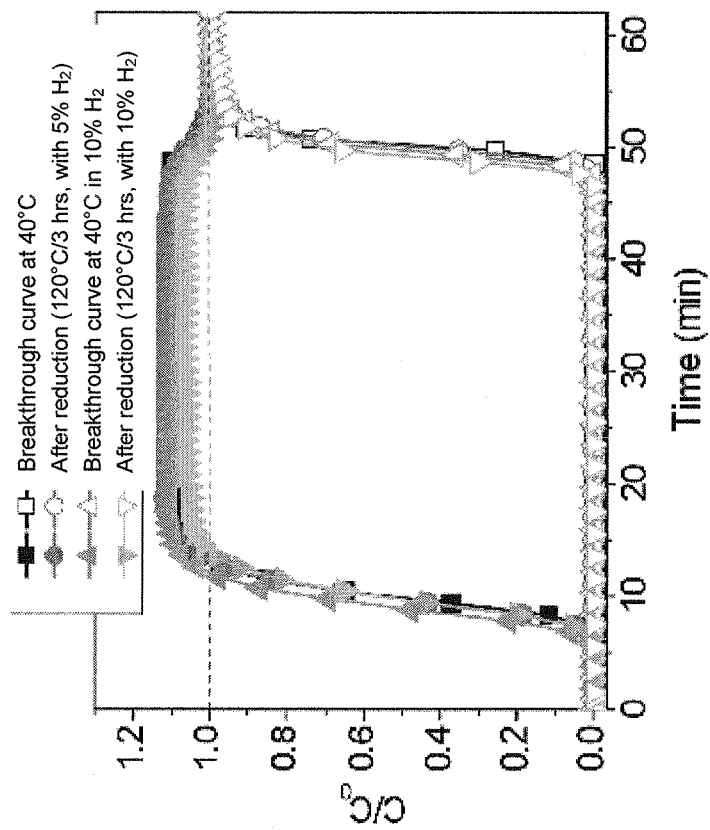
FIG. 61 shows the effect of the presence of hydrogen (H$_2$) in the propane/propylene mixture on the propane/propylene separation in MIL-100(Fe) pretreated with NH$_4$F, activated at 250° C. under helium (3 hours) (partial pressure equimolar propane/propylene mixture in He=5 kPa)

FIG. 61 shows the effect of activation for 3 hours under a current of hydrogen (10 or 20% in helium) on the propane/propylene separation for the MIL-100(Fe) solid pretreated with $NH_4F$. Hydrogen is often present in industrial gas streams and is capable of reducing $Ag^+$ or $Cu^+$ to metallic silver or copper in ion-doped silicas and thus deactivating the adsorbent. In the present case, after treatment at 120° C. under a stream containing a substantial proportion of hydrogen, no difference in terms of propane/propylene selectivity is observed before and after activation or adsorption in presence of hydrogen, indicating that this adsorbent is not deactivated in presence of hydrogen.

Figure 62:
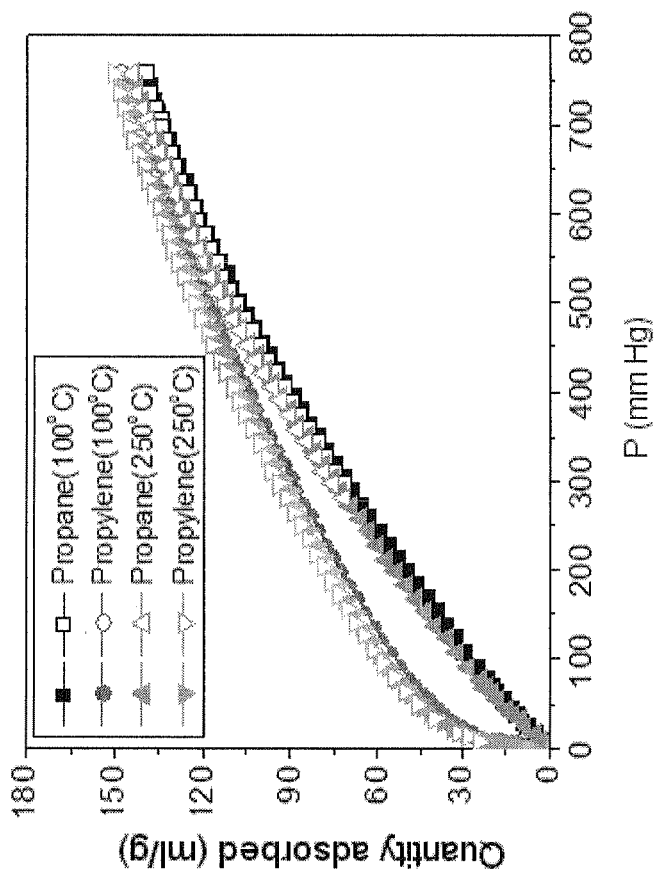
FIG. 62 shows C3 adsorption isotherms with granules of MIL-100(Fe).
Figure 63A:
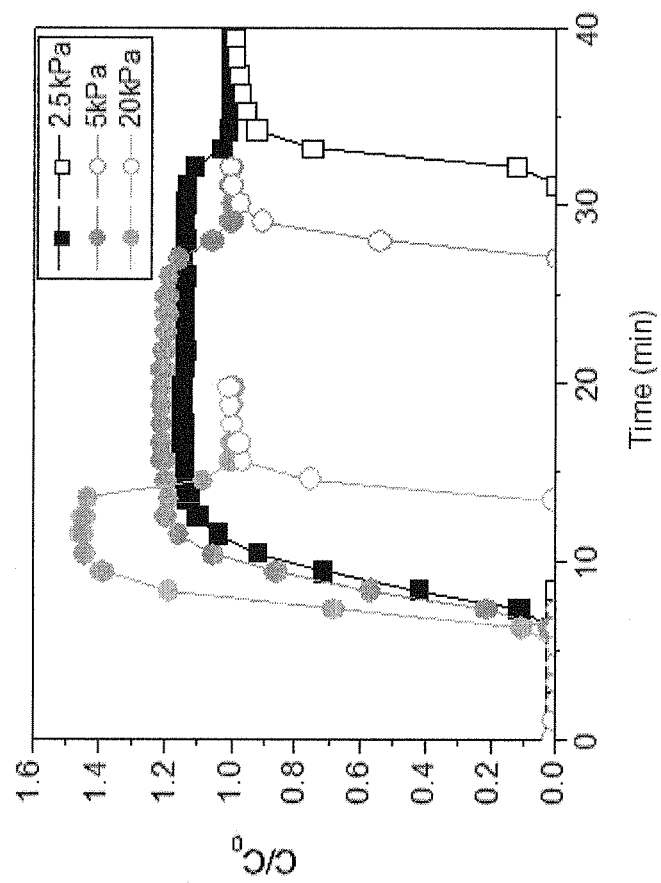
FIG. 63 shows separation tests with granules of MIL-100(Fe). Adsorption temperature: 40° C. Variable partial pressure.

An adsorbent cannot be used in powder form in the separation or adsorption of gases. It is thus important to shape the adsorbent in the form of granules or extrudates. This often results in significant modification of the adsorption properties. In the case of MIL-100(Fe) pretreated with $NH_4F$, pellets of this solid were made using a press typically used to make pellets for infrared spectroscopy (pressure of 75 Kgf/cm$^2$ for 2 minutes). The specific surface area of the granules thus formed is 1950 m2·g−1 (BET surface area) and their size is 1 mm. The propane/propylene breakthrough curves on the solid activated at 250° C. under a current of helium for 3 hours are similar to those obtained from the powder of the same sample, thus confirming that the separation properties of MIL-100 (Fe) do not change after shaping (FIG. 62). FIG. 63A shows the propane/propylene breakthrough curves at 40° C. obtained from an equimolar mixture in helium, at different partial pressures, and the MIL-100(Fe) solid pretreated with $NH_4F$ degassed for 3 hours in a current of helium at 250° C. ($S_{BET}$=2300 m$^2$/g), and shaped into the form of granules (particle size: 1 mm, $S_{BET}$: 1900 m$^2$/g).

Figure 63B:
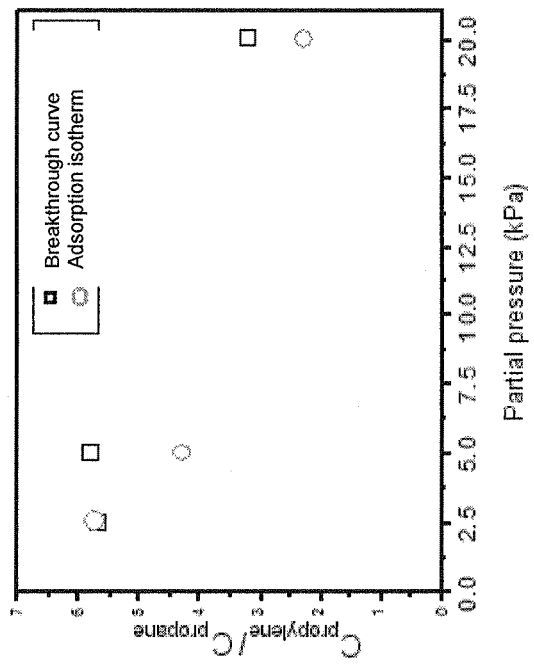

FIG. 63B shows a comparison of propylene/propane selectivities obtained with the shaped solid on the basis of adsorption isotherms (solid activated under vacuum for 12 hrs at 250° C.) or breakthrough curves (solid activated in a current of helium for 3 hrs at 250° C.)

Figure 63C:
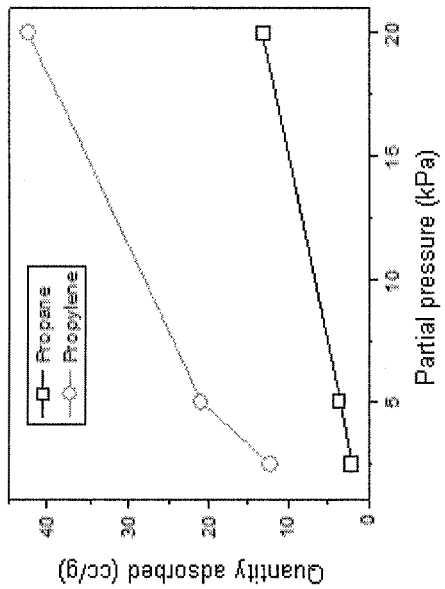

FIG. 63C shows propane/propylene adsorption isotherms at 40° C. obtained from the shaped solid.

Figure 64:
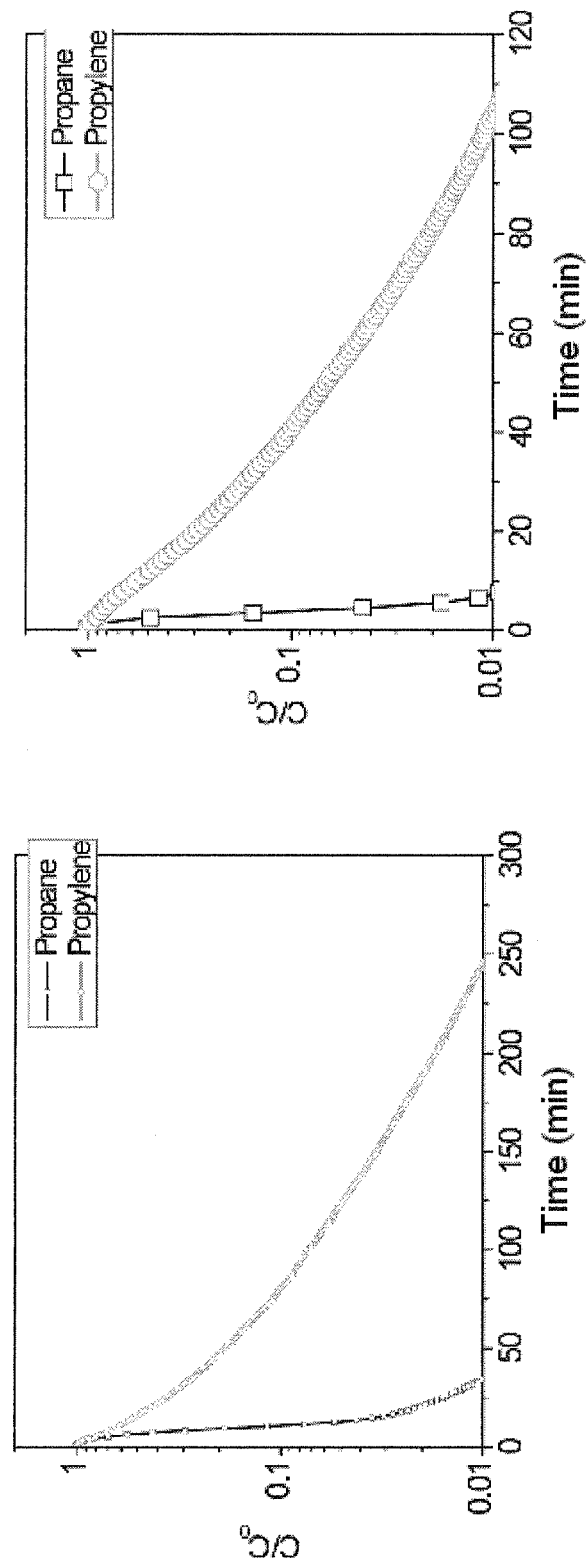
FIG. 64 shows the desorption isotherm at 40° C. in a current of helium (30 cc/min (left) and 100 cc/min (right)) after breakthrough test (equimolar propane/propylene mixture) at 40° C. and partial pressure=5 kPa on the MIL-100(Fe) solid pretreated with NH$_4$F

FIG. 64 shows the effect of the regeneration of the MIL-100(Fe) solid pretreated with $NH_4F$, degassed for one night in a current of helium at 250° C. for 3 hours. A propane/propylene mixture at a pressure of 5 kPa is passed at 40° C. over the column containing the activated MIL-100(Fe), until saturation of the adsorbent. The solid is then regenerated in a current of helium at 40° C. at a helium flow rate of 30 cc/min. As is shown by the desorption curves at 40° C., the propane is totally desorbed in less than 50 minutes whereas the propylene is totally removed in 250 minutes.

Figure 65:
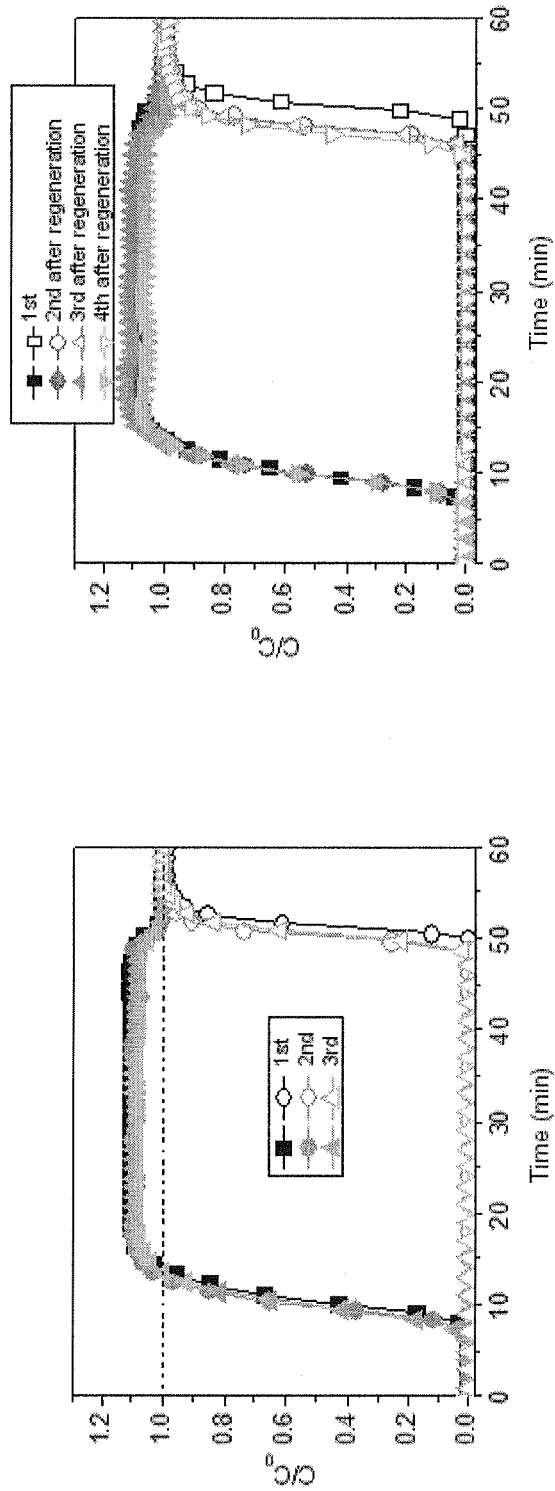
FIG. 65 shows repetitive breakthrough curves with regeneration under helium of the MIL-100(Fe) solid pretreated with NH$_4$F. Breakthrough test at 40° C. and 5 kPa. Regeneration: 30 ml/min He at 200° C. for 1 h (left) or 100 ml/min He at 40° C. for 2 hours.

FIG. 65 shows repetitive breakthrough curves with regeneration under helium (MIL-100(Fe) solid pretreated with $NH_4F$), with a flow rate of 30 cc/min. at 200° C. for 1 hour (figure on left) or 100 ml/min. at 40° C. for 2 hours (figure on right). Apart from a slight loss of selectivity (or of adsorption capacity) for propylene after the first regeneration, it is clear that the regeneration in a current of helium is very effective.

Figure 66A:
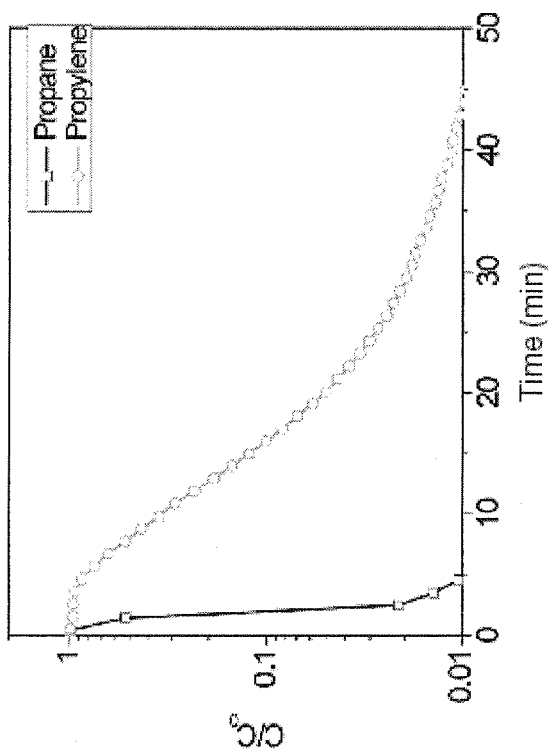
FIG. 66A shows the desorption isotherm at 80° C. in a current of helium (100 CC/min) after breakthrough test (equimolar propane/propylene mixture) at 80° C. and partial pressure=5 kPa on the MIL-100(Fe) solid pretreated with NH$_4$F.
Figure 66B:
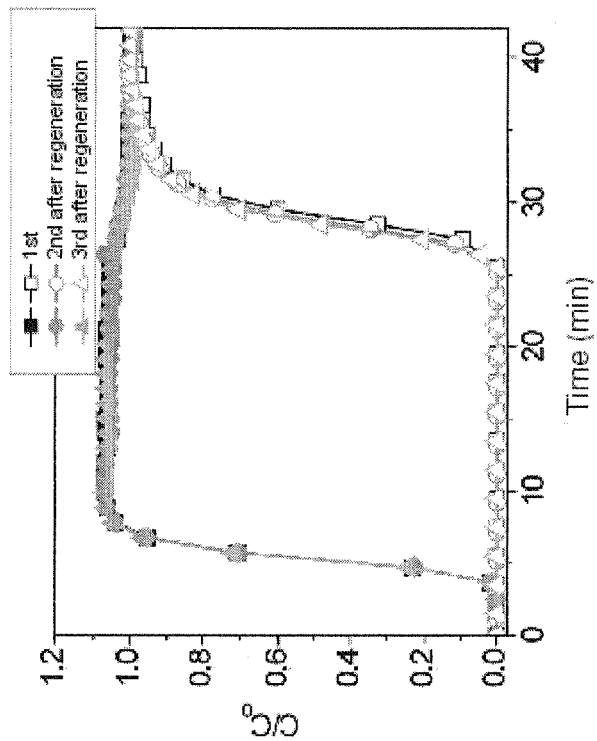
FIG. 66B shows the effect of the regeneration of the MIL-100(Fe) solid pretreated with NH4F. Breakthrough test at 80° C. and 5 kPa. Regeneration: with 100 ml/min He at 80° C. for 2 hours.

FIG. 66 shows the effect of the regeneration of the MIL-100(Fe) solid pretreated with $NH_4F$, degassed for one night in a current of helium at 250° C. for 3 hours. A propane/propylene mixture at a pressure of 5 Kpa is passed at 80° C. over the column containing the activated MIL-100(Fe), until saturation of the adsorbent. The solid is then regenerated in a current of helium at 80° C. at a helium flow rate of 100 cc/min. As is shown by the desorption curves at 80° C. (figure on left), the propane is totally desorbed in less than 5 minutes whereas the propylene is totally removed in 45 minutes. Increasing the temperature and the helium flow rate thus makes it possible to significantly reduce the regeneration time of the MIL-100 (Fe) column. The figure on the right next shows repetitive breakthrough curves with regeneration under helium (MIL-100(Fe) solid pretreated with $NH_4F$), with a flow rate of 100 cc/min. at 80° C. for 2 hours. No loss of selectivity (or of adsorption capacity) is observed either for the propylene or for the propane after the first regeneration, and it is clear that regeneration in a current of helium at 80° C. for 2 hours is very effective.

Figure 67:
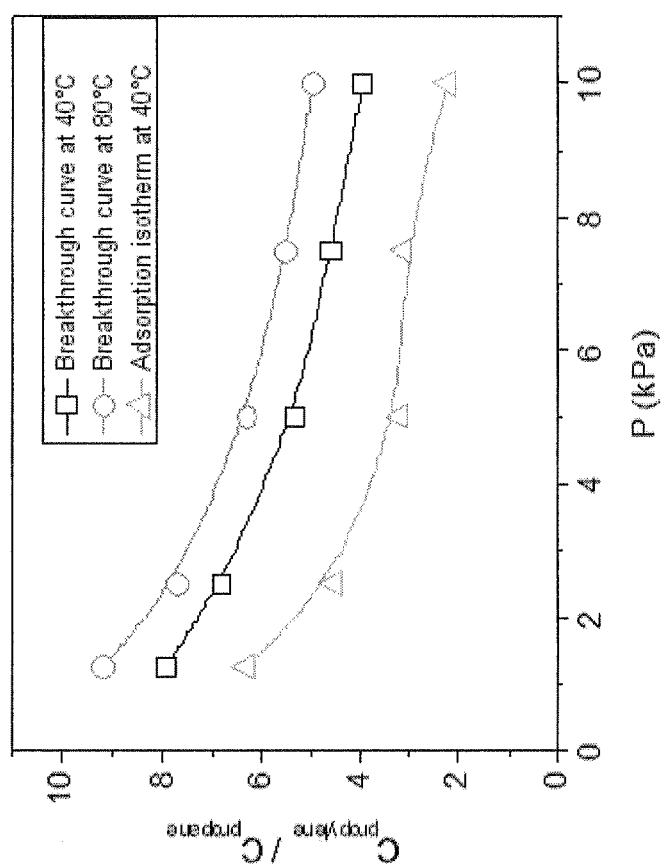
FIG. 67 shows the effect of the pressure at variable temperature (40 or 80° C.) on the propane/propylene separation under helium on the MIL-100(Fe) solid pretreated with NH4F then degassed at 250° C. for 3 hours in a current of helium (equimolar propane+propylene mixture).

FIG. 67 shows the propylene/propane selectivities measured from data in breakthrough curves (at 40 and 80° C.) of propane/propylene mixtures at different partial pressures in helium from the MIL-100(Fe) solid pretreated with $NH_4F$ and activated in a current of helium for 3 hrs at 250° C. By way of comparison, the selectivities deduced from adsorption isotherms (at 40° C.) obtained from the same solid activated under secondary vacuum at 250° C. for 12 hours are appended. First of all, it is observed that the selectivities deduced from breakthrough curves are slightly greater than those obtained from pure substance adsorption isotherms, and secondly that increasing the temperature makes it possible to increase the values of the propylene/propane selectivities.

Example 21

Propane-Propene Adsorption Isotherms in CPO-27 (Ni)

Synthesis of the CPO-27(Ni) solid or $Ni_2[C_6H_2(OH)_2-(CO_2)_2](H_2O)_2.8H_2O$ was reported in "Hydrogen adsorption in a nickel based coordination polymer with open metal sites in the cylindrical cavities of the desolvated framework", P. D. C. Dietzel, B. Panella, M. Hirscher, R. Blom, H. Fjellvag, *Chem. Commun.*, 2006, 959-961 [ref 53].

Propane and propylene adsorption measurements were performed at thermodynamic equilibrium (FIG. 53) at 40° C. from 1 g of CPO-27(Ni) solid previously activated at 250° C. under primary vacuum (P=1 Pa for 16 hours)

Figure 53:
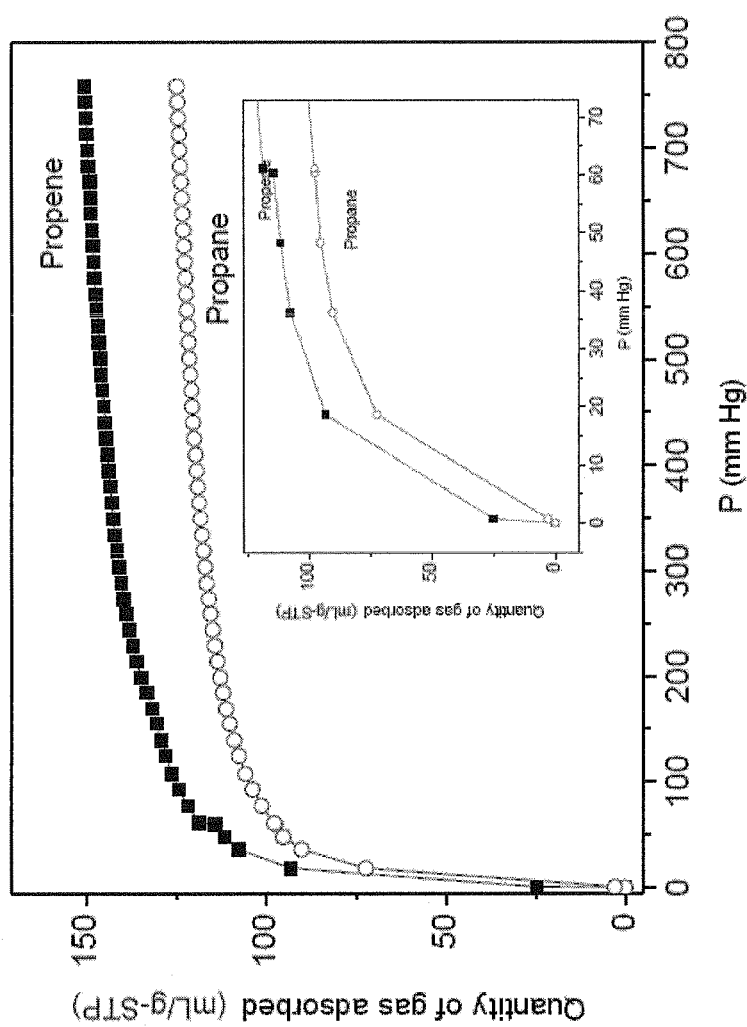
FIG. 53 shows adsorption isotherms of propane and propylene in thermodynamic equilibrium at 40° C. from 1 g of CPO-27(Ni) solid previously activated at 250° C. under primary vacuum (P=1 Pa for 16 hours).

The profile of the propane and propylene adsorption isotherms shows a small difference between the quantities of gas adsorbed, 125 and 150 mL/g for propane and propylene respectively (FIG. 53). The propane-propylene selectivity has a value of 10 at low pressure (1 mm Hg). In contrast, at pressures greater than 15 mm Hg the selectivity changes to 1.5.

Example 22

Propane-Propene Adsorption Isotherms in CPO-27 (Fe)

Propane and propylene adsorption measurements can be performed at thermodynamic equilibrium at 40° C. from 1 g of CPO-27(Fe) solid previously activated at different temperatures (20, 50, 100, 150, 200, 250° C.) under primary vacuum (P=1 Pa for 16 hours)

The expected profile of the adsorption isotherms of propane and propylene will be very similar to that obtained for the Ni compound (shown in the previous example), with a higher propane-propylene selectivity at low pressures and larger values at higher pressures. Considering the retrodonation effect of the iron, a better propane-propylene separation is expected.

Example 23

Propane-Propylene Adsorption Isotherms in MIL-127 (Fe)

Figure 54:
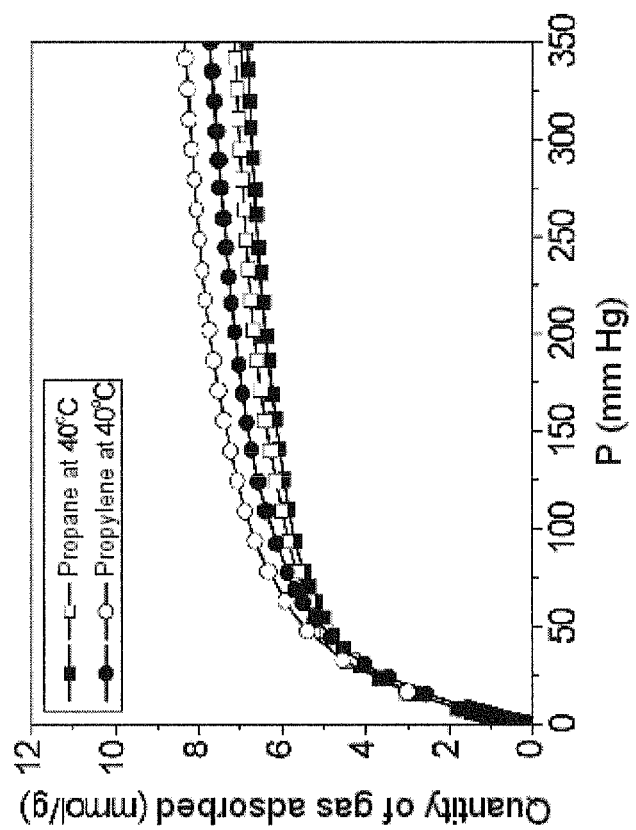
FIG. 54 shows adsorption isotherms of propane and propylene in thermodynamic equilibrium at 40° C. from 1 g of CPO-27(Fe) solid previously activated at 150° C. under primary vacuum (P=1 Pa for 16 hours).
Figure 55:
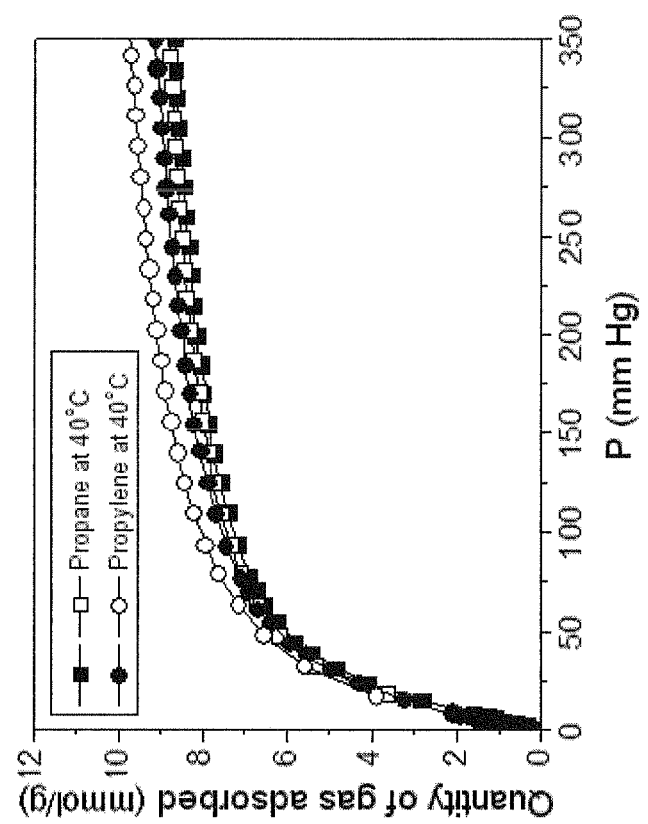
FIG. 55 shows adsorption isotherms of propane and propylene in thermodynamic equilibrium at 40° C. from 1 g of CPO-27(Fe) solid previously activated at 250° C. under primary vacuum (P=1 Pa for 16 hours).

Propane and propylene adsorption measurements were performed at thermodynamic equilibrium at 40° C. from 1 g of MIL-127(Fe) solid previously activated at 150 (FIG. 54) and 250° C. (FIG. 55) under primary vacuum (P=1 Pa for 16 hours).

The profile of the adsorption isotherms of propane and propylene is very similar, both in the material degassed at 150° C. and at 250° C. The propane-propylene selectivity observed is very low (1.2). The selectivity does not display significant changes with the pressure.

Example 24

Comparison of the Reduction of the Different Fluorinated MIL-100(Fe) Materials Activated by Two Method, Non-Fluorinated MIL-100(Fe) and MIL-127(Fe)

The reduction level of the various solids was determined by CO gas adsorption by infrared, according to the example 5. Thus the reduction was studied on the solids treated under primary vacuum at different temperatures (from 150 to 250° C.) for variable times (3 or 12 hrs).

The following materials were compared:
a) fluorinated MIL-100(Fe) solid (X=F, FIG. 22) pretreated beforehand in water or in ethanol under reflux for 3 hours
b) non-fluorinated MIL-100(Fe) solid (X=OH, Cl) pretreated beforehand in water or in ethanol under reflux for 3 hours
c) fluorinated MIL-100(Fe) solid pretreated in a solution of $NH_4F$
d) MIL-127(Fe) solid For pretreatment c), the solid is dispersed in a 1 mol/l solution of aqueous $NH_4F$ solution at 70° C. for 24 hours and immediately filtered hot and washed with hot water. Finally the solid is dried for one night at 100° C. in an oven.

This study made it possible to compare, on the same structure, the influence of the presence or absence of fluorine in the synthesis of MIL-100(Fe) or $Fe3O[C6H3-(CO2)3]2.X.nH2O$, i.e. fluorinated (X=F, FIG. 22) or non-fluorinated (X=OH, Cl) MIL-100(Fe) solid, both pretreated beforehand in water or in ethanol under reflux for 3 hours, and the fluorinated MIL-100(Fe) pretreated in a solution of NH4F.

Figure 56:
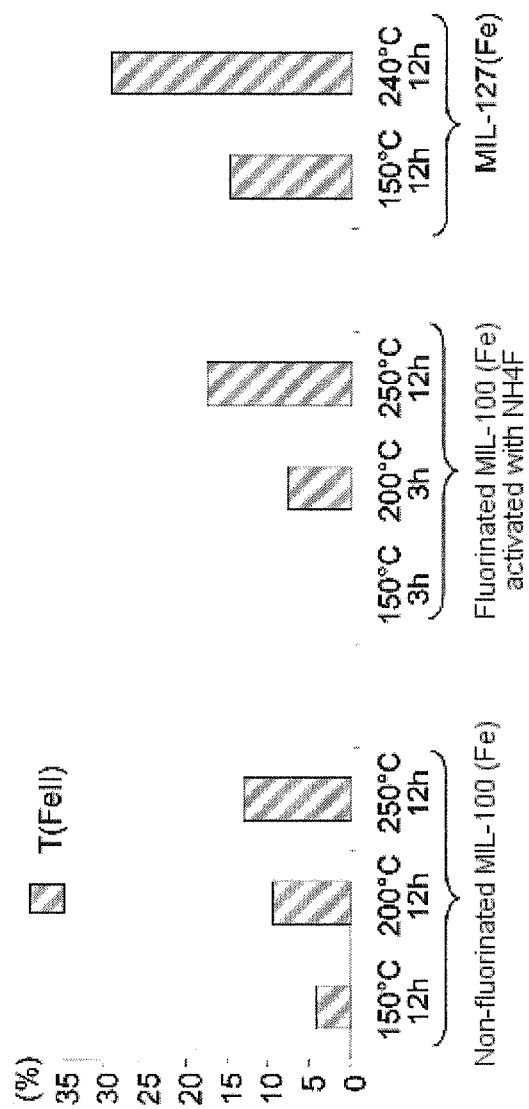
FIG. 56 shows a comparison of the content of $Fe^{2+}$ ions (expressed in % of iron(II) sites relative to the total number of iron sites) obtained for non-fluorinated MIL-100(Fe) (X=OH, Cl), fluorinated MIL-100(Fe) (X=F) pretreated with NH$_4$F, and MIL-127(Fe).

As discussed in example 5, the activation temperature has a clear influence on the reduction of the iron. As is shown by FIG. 56, an optimal temperature around 250° C. (under vacuum for 12 hrs) was observed both for the MIL-100(Fe) materials and for MIL-127.

The treatment with $NH_4F$ was found more effective, giving higher reduction values (around 18%) than in the MIL-100 (Fe) solid with or without F pretreated under reflux in water (around 13-15%).

In addition, the MIL-127 solid exhibited very high reduction of the iron (close to 30%) when it is activated at 240° C. under vacuum.

Example 25

Microcalorimetry and Propane/Propylene and CO/CO2 Adsorption Isotherms in MIL-100(Fe)

Propane/propylene and $CO/CO_2$ adsorption and heat of adsorption measurements were performed at thermodynamic equilibrium at ambient temperature from 0.4 g of MIL-100 (Fe) solid activated at 100 or 250° C. (linear increase of 0.2° C./min then 12 hr plateau at the final temperature) under secondary vacuum ($10^{-5}$ mbar). The experiments were performed with doses of gas up to a pressure of 1 bar.

Figure 68:
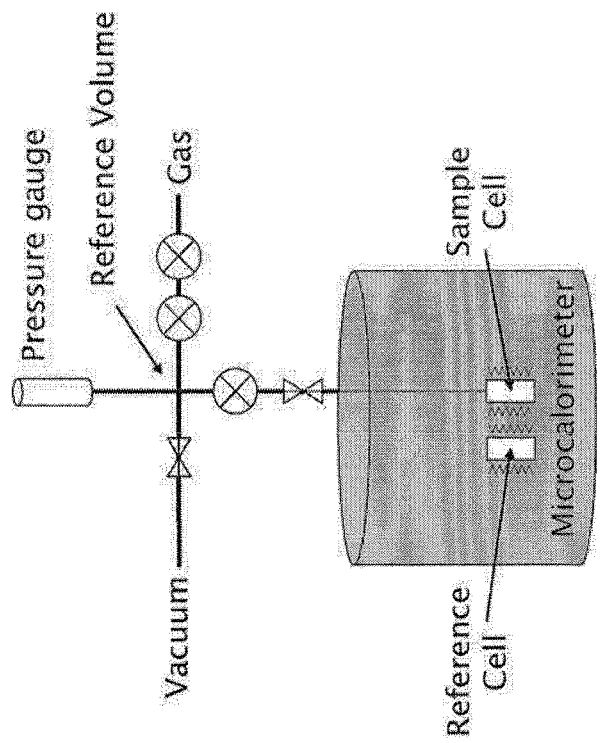
FIG. 68 is a diagram of an apparatus used for the microcalorimetry experiments of example 25.

The instrument used to perform these measurements was described in P. L. Llewellyn & G. Maurin, C. R. Chimie, 8, 283-302 (2005) [ref 55]. The home-made gas phase adsorption microcalorimeter, shown diagrammatically in FIG. 68, is coupled with a volumetric gas adsorption instrument (Micromeritics ASAP 2010). Thus the gas adsorption and microcalorimetry measurements are performed simultaneously.

Propane/Propylene

Figure 69:
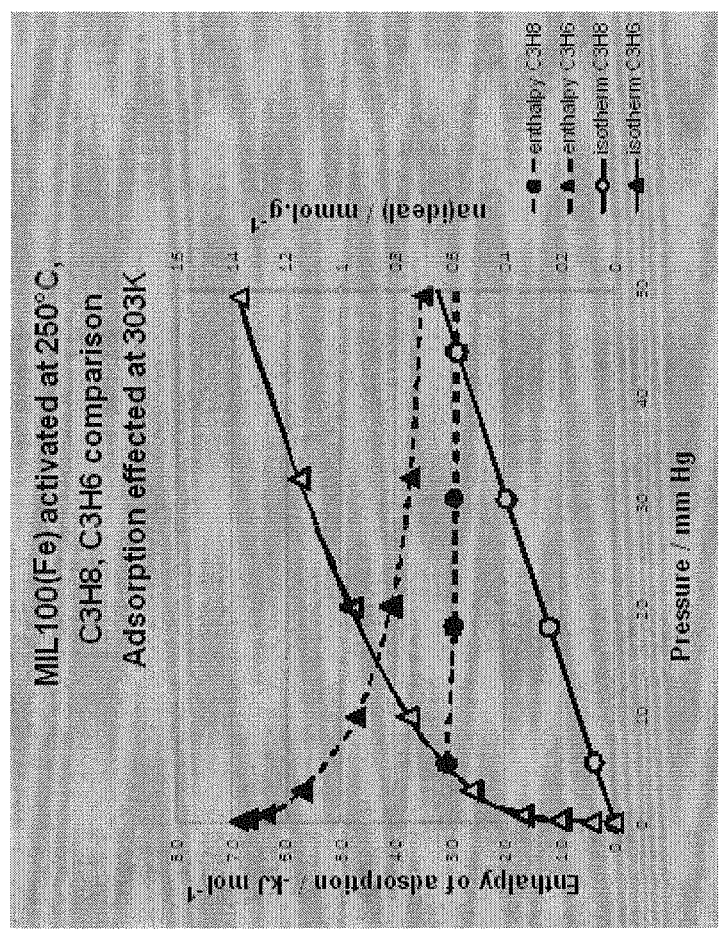
FIG. 69 shows adsorption isotherms and heats of adsorption of propane and propylene at 303K in the MIL-100(Fe) solid after activation at 250° C. under secondary vacuum for 12 hours.

The material MIL100(Fe) is partially reduced after the treatment at 250° C. under vacuum and shows good propane/propylene selectivity over the whole pressure range explored (FIG. 69). Thus, at low pressure (5 mm Hg) and at a value of 7.5 mm Hg decreasing with increasing pressure (4 to 20 mm Hg or 3 to 30 mm Hg). The enthalpies of adsorption of propylene are greater than those observed for propane (−30 KJ/mol), with however a very marked energy difference (−65 KJ/mol) at low pressures, consistently with a much stronger interaction of the propylene with the unsaturated metal sites Fe2+ compared to the propane.

Figure 70:
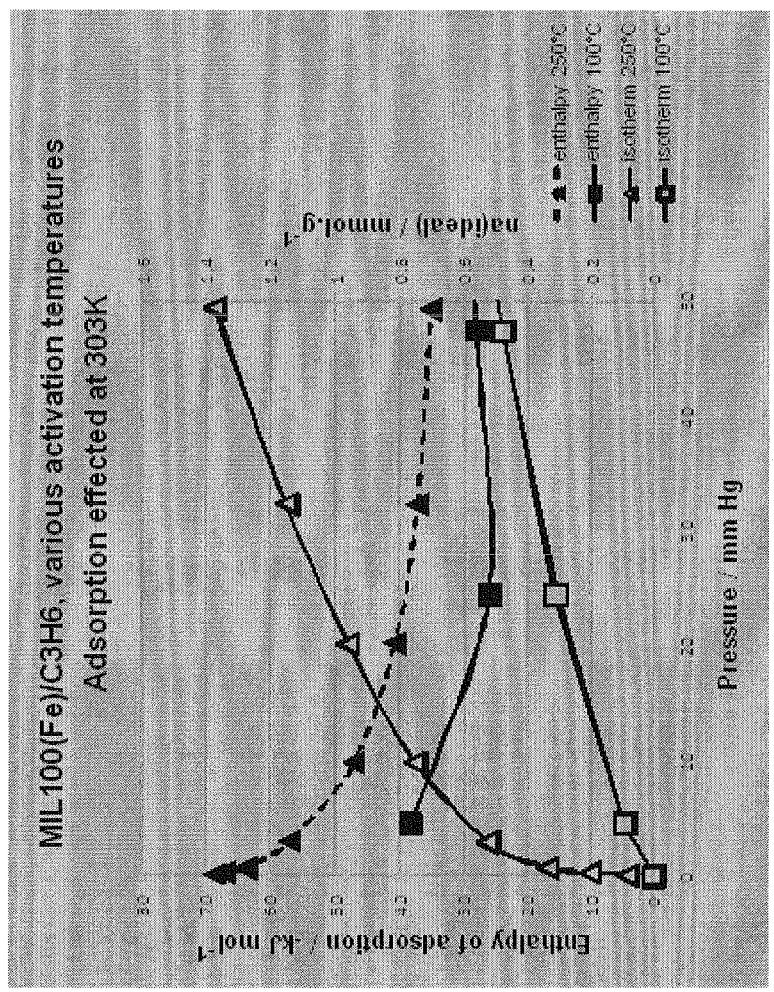
FIG. 70 shows adsorption isotherms and heats of adsorption of propylene at 303K in the MIL-100(Fe) solid after the treatment at 100 or 250° C. under secondary vacuum for 12 hours.

The influence of the pretreatment temperature on the adsorption of propylene and also on the heats of adsorption was studied (FIG. 70). The MIL-100(Fe) solid activated at 250° C. (under primary vacuum for 16 hours) adsorbs a much greater quantity of propylene than the material activated under the same conditions at a temperature of 100° C. (primary vacuum, 16 hours), consistently with the higher heats of adsorption when the activation temperature increases. This is due to the presence of unsaturated metal sites $Fe^{2+}$ which interact more strongly with the propylene, by a retro-donation effect, than the unsaturated metal sites $Fe^{3+}$.

CO/CO2

Figure 71:
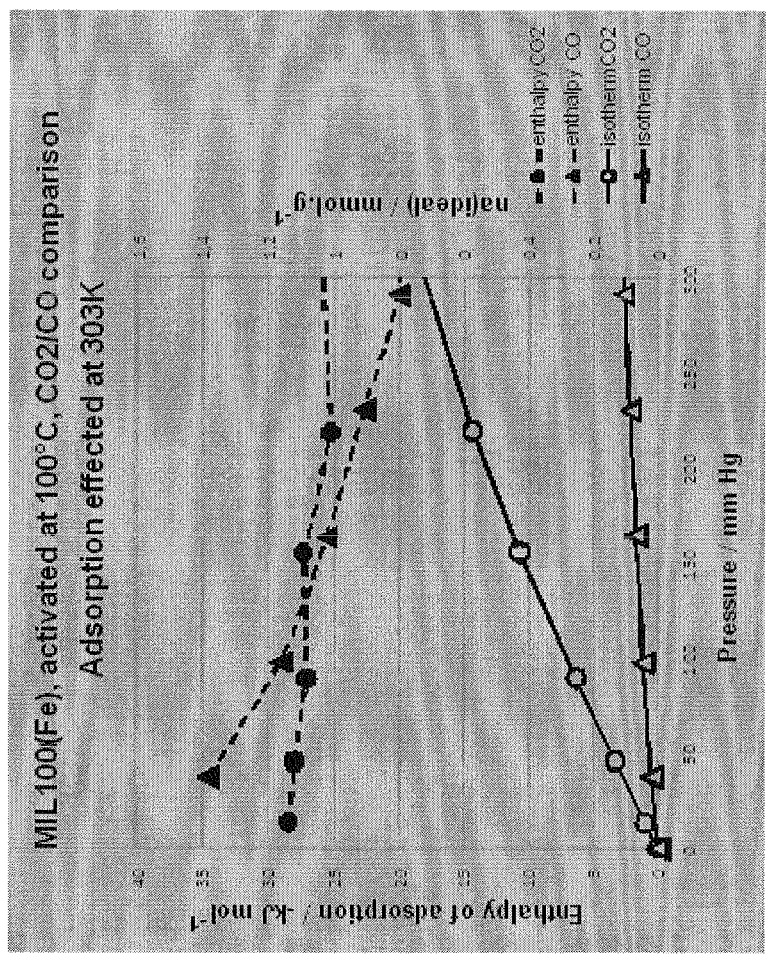
FIG. 71 shows adsorption isotherms and heats of adsorption of CO and CO2 at 303K in the MIL-100(Fe) solid after activation at 100° C. under secondary vacuum for 12 hours.

The material MIL-100(Fe) after activation under vacuum at 100° C. shows a $CO_2/CO$ selectivity of about 7 (FIG. 71). However, the enthalpies of adsorption of $CO_2$ (28.4 kJ/mol) are slightly lower than those for CO (34.5 kJ/mol) since in contrast to CO which only interacts with the unsaturated metal sites, $CO_2$ can interact with a greater number of sites (metal, aromatic rings, oxygens of carboxylates . . . ).

Table 13 shows the enthalpies of adsorption in kJ/mol extrapolated to zero recovery levels so as to quantify only the gas-solid interactions (error in the measurement+/−0.2 kJ/mol)

TABLE 13

| Gas | 100° C. | Measurement P/ mmHg | 200° C. | Measurement P/ mmHg | 250° C. | Measurement P/ mmHg |
|---|---|---|---|---|---|---|
| CO2 | 28.4 | 13.6 | 34.2 | 7.6 | 33.6 | 33.6 |
| CO | 34.5 | 37 | 49.6 | 7.0 | 50.5 | 4.2 |
| C3H8 | | | | | 30.9 | 5.6 |
| C3H6 | 38.5 | 4.6 | | | 68.7 | 0.1 |

Example 26

Figure 72:
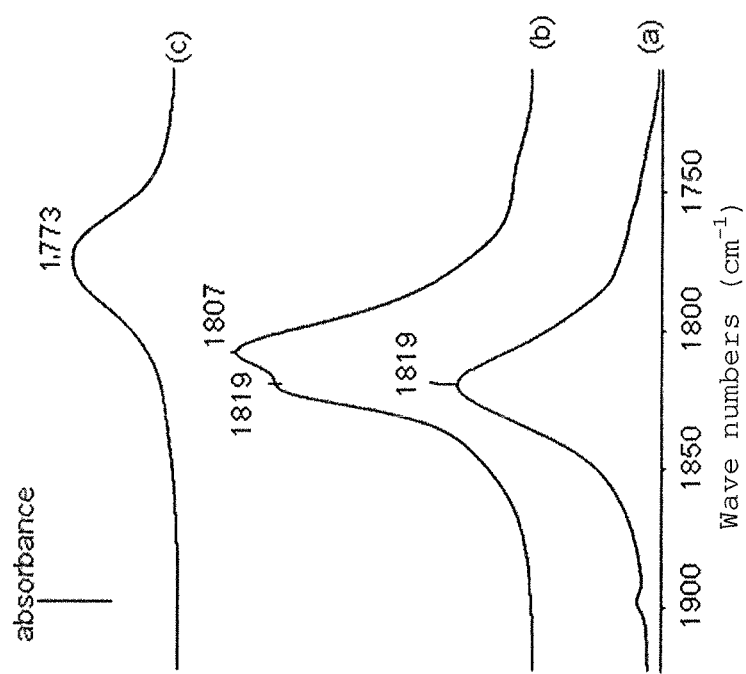
FIG. 72 shows the infrared bands for the stretching vibration of NO molecules interacting with the coordinatively unsaturated Fe(II) sites of the material MIL-102(Fe) activated under vacuum at 225° C. for 12 hours (spectrum a), the material MIL-100(Fe) pretreated with NH$_4$F and activated under vacuum at 250° C. for 12 hours (spectrum b) and the material MIL-127(Iron) activated under vacuum at 150° C. for 12 hours (spectrum c). The infrared spectra are recorded at ambient temperature under a pressure of NO equal to 1333 Pa.

Influence of the Nature of the Ligand on the Retrodonation Property of the FeII Sites The position of the vNO stretching band of the nitrosyl species coordinated onto the coordinatively unsaturated Fe(II) sites reflects of the strength of the interaction between the NO molecule and the metal site. The lower the wave number, the stronger will be the interaction involving retrodonation (A. A. Davidov, Infrared Spectroscopy of Adsorbed Species on the Surface of Transition Metal Oxides, Wiley Interscience, 1990 p 123-130 chapter 2 [ref 58]). This interaction can be modulated by the nature of the organic ligand (Structure and nuclearity of active sites in Fe-zeolites: comparison with iron sites in enzymes and homogeneous catalysts Adriano Zecchina, Mickaël Rivallan, Gloria Berlier, Carlo Lamberti, Gabriele Ricchiardi, Phys. Chem. Chem. Phys., 2007, (27), 3483-3499 [ref 56]). FIG. 72 shows that the position of the vNO band of the nitrosyl species on iron(II) depends on the structure and the ligand used. For MIL-127 (Fe), the lower value of the NO band reflects a retrodonation effect greater than on the other solids.

Example 27

Influence of the FeII Content on the Purification of a H2/CO2/CO Mixture

The MIL-127 solid (Fe) was pelleted in an infrared cell then heated under a current of argon (20 cc./min) for 3 hours at 150° C. or 250° C.

Figure 73:
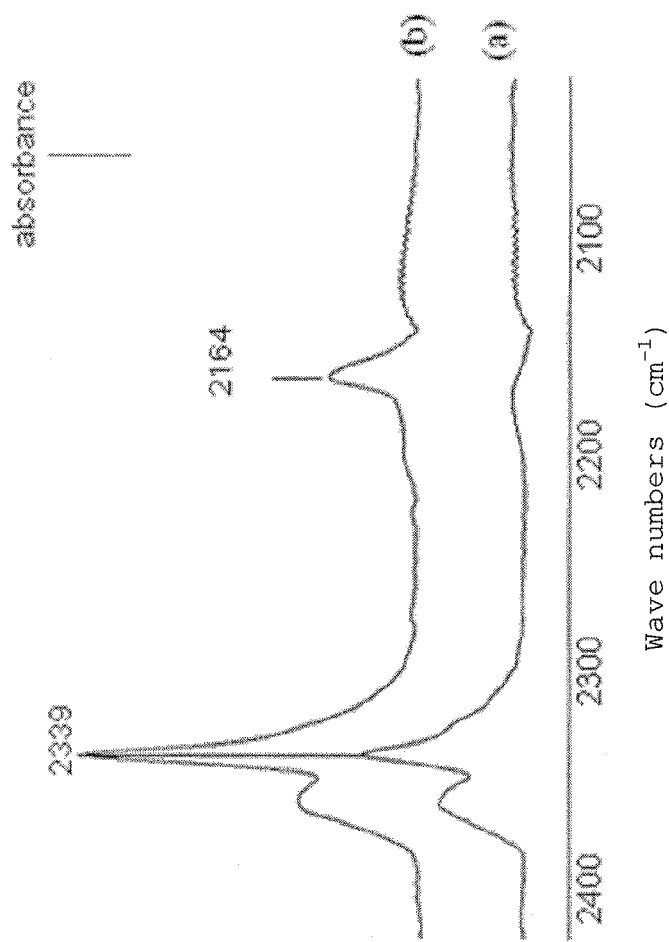
FIG. 73 shows an infrared spectrum of the MIL-127(iron) solid under a current of H$_2$/CO/CO$_2$ at 30° C. after heating under a current of argon at 150° C. (spectrum a), 250° C. (b).

The solid was then subjected to a stream (20 cc./min) made up of argon (48% vol), H2(50%), $CO_2$(1%) and CO(1%) at 30° C. FIG. 73 shows that the CO2 is adsorbed on the solid activated at 150 and 250° C. (band at 2339 cm−1) whereas only the activation at 250° C. gives rise to the adsorption of CO on the surface (band at 2339 cm−1). The position of the v(CO) band (2164 cm−1) is characteristic of CO coordinated onto FeII sites. This result shows that the solid under a current of H2/CO2/C0 possesses a stronger affinity towards CO when it exhibits FeII sites. The previously reduced solid should thus display better performance in hydrogen purification processes.

Example 28

Influence of FeII Content on the Affinity of MIL-100 (Fe) for Propyne ($C_3H_4$)

Figure 74:
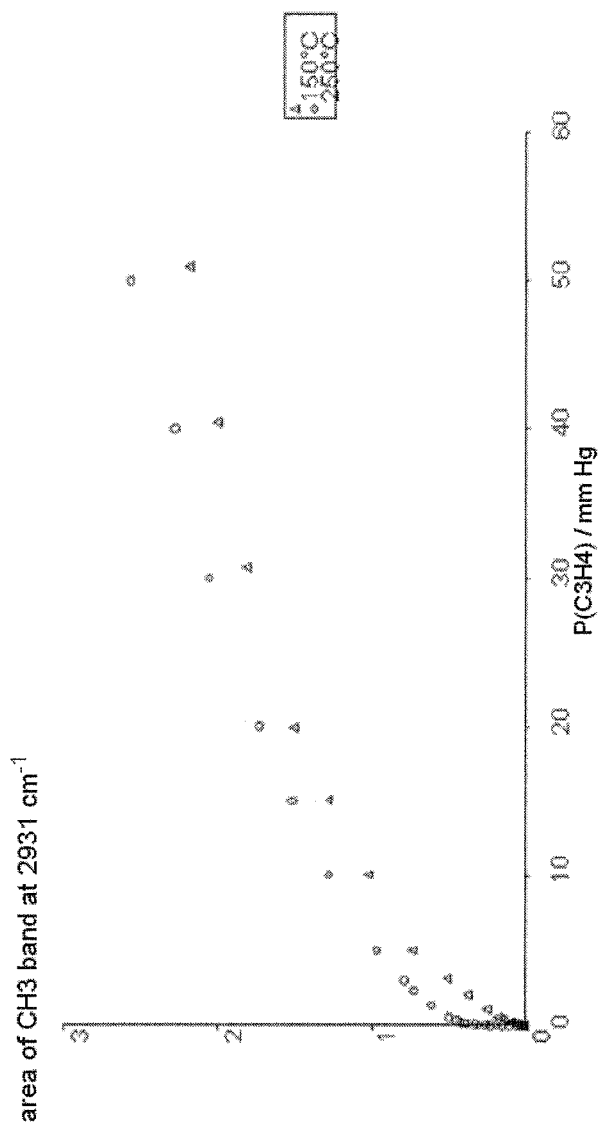
FIG. 74 shows the adsorption isotherms at 25° C. of C3H4 on MIL-100(Fe) pretreated with NH$_4$F and activated under secondary vacuum at 150° C. and 250° C. The quantities are qualitatively deduced from the intensity of the stretching band of the methyl group at 2931 cm−1.
Figure 75:
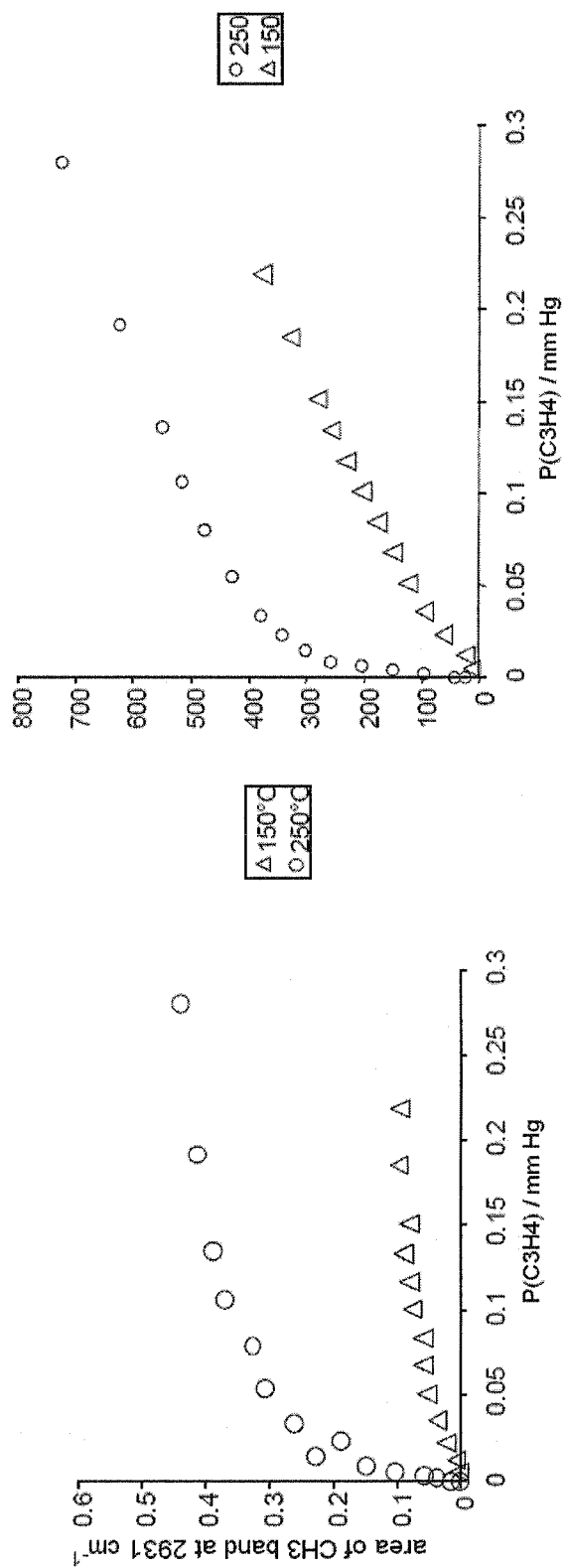
FIG. 75 shows the adsorption isotherms at 25° C. of C3H4 on MIL-100(Fe) pretreated with NH$_4$F and activated under secondary vacuum at 150° C. and 250° C. in the pressure range 0-0.3 mm Hg. On left: the quantities adsorbed are deduced from the intensity of the stretching band of the methyl group at 2931 cm−1. On right: the quantities adsorbed given in μmol per gram of dehydrated solid are deduced by the volumetric method.
Figure 76:
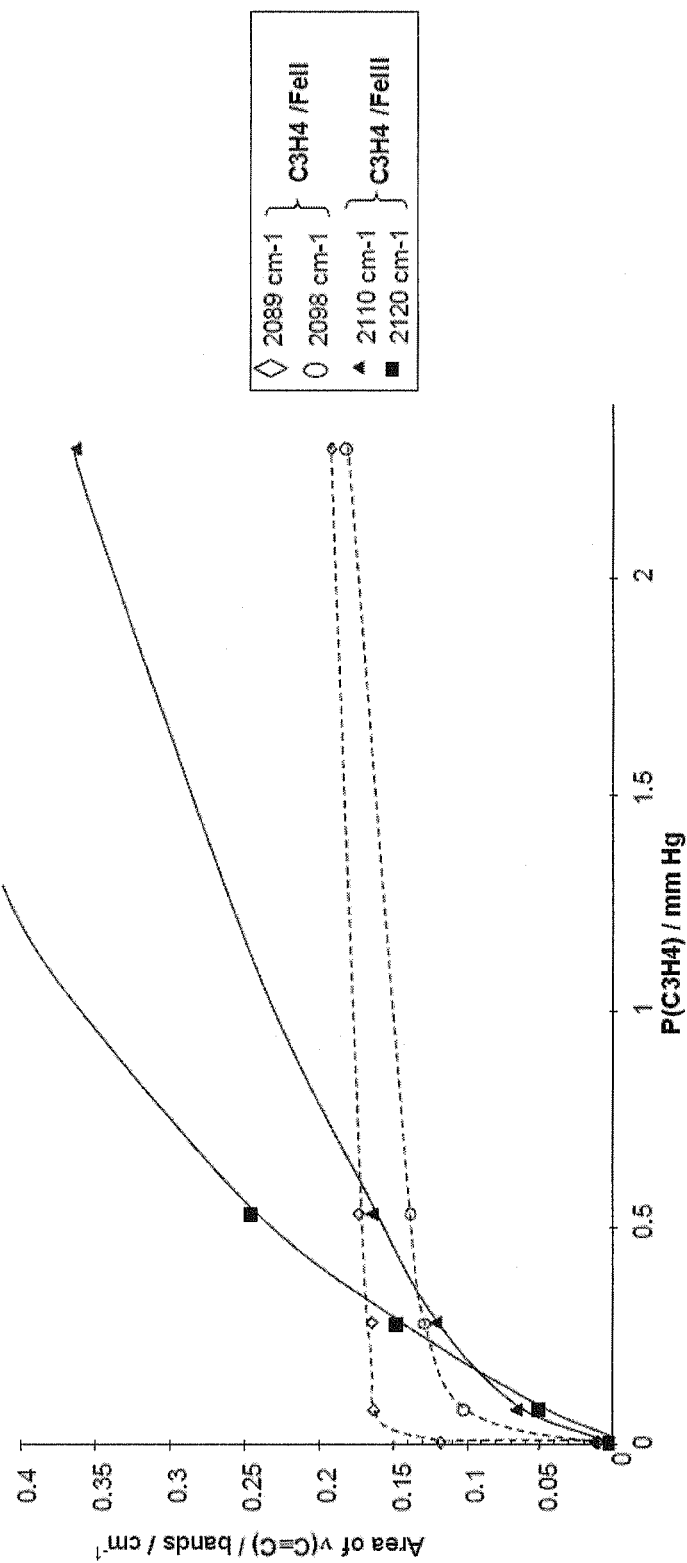
FIG. 76 shows the variation of the infrared bands v(C≡C) of C3H4 adsorbed on the FeII and FeIII sites of MIL-100(Fe) pretreated with NH$_4$F and activated at 250° C. as a function of the pressure of C3H4 in the gaseous phase (range 0-2.5 mm Hg).

The MIL-100(Fe) solid pretreated with $NH_4F$ was placed in a quartz infrared cell then activated under secondary vacuum for 3 hours at 150° C. or 12 hours at 250° C. The solid was contacted with increasing propyne pressures at 30° C. The quantity of propyne adsorbed was estimated by infrared spectroscopy and simultaneously by a volumetric method (FIG. 74). FIGS. 74 and 75 show that the solid reduced at 250° C. adsorbs more propyne at very low pressure (0-1 mm Hg). FIG. 76 shows that the propyne is adsorbed preferentially on the iron II sites at low pressure.

Example 29

Influence of FeII Content on the Affinity of MIL-100(Fe) for Propene (C3H6)

Figure 77:
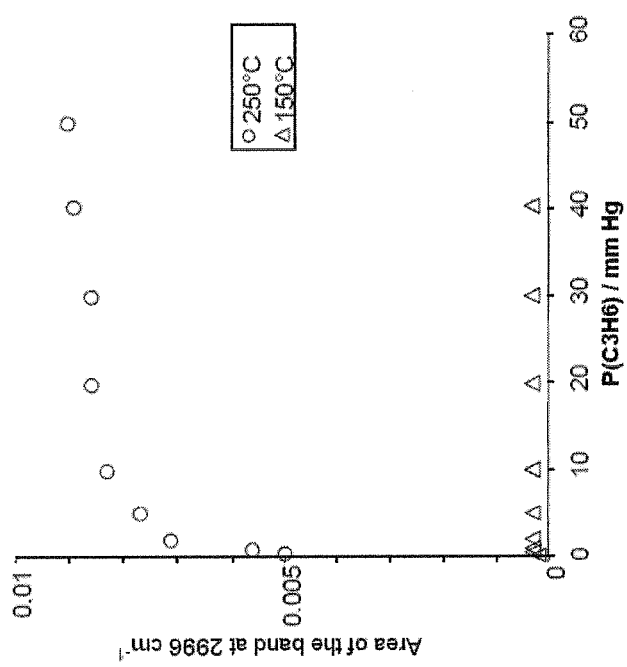
FIG. 77 shows the adsorption isotherms of C3H6 on fluorinated MIL-100(Fe) (X=F) activated at 150° C. and 250° C. in the pressure range 0-60 mm Hg. The quantities of C3H6 adsorbed on the Fe(II) sites are qualitatively represented by the area of the band at 2996 cm−1.

The fluorinated MIL-100(Fe) solid (X═F) was placed in a quartz infrared cell then activated under secondary vacuum for 12 hours at 150° C. or 12 hours at 250° C. The solid was contacted with increasing propyne pressures at 30° C. The quantity of propene adsorbed on ironII as a function of the pressure in the gas phase was qualitatively estimated by infrared spectroscopy (FIG. 77): the quantity adsorbed onto the Fe(II) sites is markedly greater on the solid activated at 250° C. (range 0-20 mm Hg).

Example 30

Reduction of a Co-Based MOF

The synthesis of the porous cobalt (III) metalloporphyrin [CoT(p-CO2)PPCo1.5], named PIZA-1, was reported in "A functional zeolite analogue assembled from metalloporphyrins", M. E. Kosal, J-H Chou, S. R. Wilson, K. S. Suslick, Nature, 2002, 1, 118-121 [ref 52].

The reduction of the cobalt (III) to cobalt (II) can for example be performed by one of the following two methods:
 in presence of a reducing gas (He, $H_2$). 200 mg of the solid are placed a column through which a current of gas (He, $H_2$) is passed at a variable flow rate (from 0.01 to 10 mL/min).
 200 mg of the solid are placed in a slink line under primary vacuum ($10^{-2}$ bar) and heated at different temperatures (from 50 to 250° C.) for 24 hours.

The solid thus reduced can be used for the separation of gases.

Example 31

Reduction of a Metal of the MOF with Charge Compensation by Oxidation of the Spacer (Redox Ligand) MIL-88B-2OH The reduction of the porous MOF solid can be performed by charge compensation by the loss of the counter-ion of the metal, but also by the oxidation of the organic ligand, using a redox ligand. Thus, the presence of redox ligands in the MOF can be useful in the reduction of MOF for the separation of gases.

For example in the iron carboxylate MIL-88B-2OH(Fe), $Fe_3O[C_6H_2\ (OH)_2-(CO_2)_2]_3.X.nH2O$ (X═F, Cl, OH), the organic ligand is 2,5-dihydroxoterephthalic acid. This ligand can be present in its reduced, i.e. hydroquinone, form or in its oxidized, quinone, form (see scheme below).

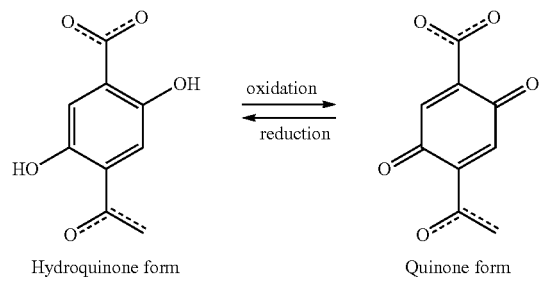

Hydroquinone form          Quinone form

Synthesis of the MIL-88B-2OH(Fe) Solid: See Example 1, Section j)

Reduction of MIL-88B-2OH(Fe):

The reduction of the iron (III) to iron (II) can be performed by the oxidation of the redox ligand, 2,5-dihydroxoterephthalic acid, for example by one of the following two methods:

100 mg of MIL-88B_2OH(Fe) are placed in a column through which a current of reducing gas (He, H2) is passed at a variable flow rate (from 0.01 to 10 mL/min) for 2-48 hours.

200 mg of the solid are placed in a slink line under primary vacuum ($10^{-2}$ bar) and heated at different temperatures (from 50 to 250° C.) for 24 hours.

LIST OF REFERENCES

[1] US patent application 2003-0078311
[2] U.S. Pat. No. 6,929,679
[3] U.S. Pat. No. 6,930,193
[4] (a) C. Staudt-Bickel, J. W. Koros, J. Membr. Sci., 1993, 82, 117, (b) J. S. Yang G. H. Hsuie, J. Membr. Sci., 1998, 138, 203, (c) A. Sungpet, J. D. Way, C. A. Koval, M. E. Eberhart, J. Membr. Sci., 2001, 189, 271, (d) O. H. Leblanc, W. J. Ward, S. L. Matson, S. G. Kimura, J. Membr. Sci., 1980, 6, 339, (e) I. Pinnau, L. G. Toyl, J. Membr. Sci., 2001, 184, 39, (f) C. M. Shue, S. Kulvaranon, M. E. Findlay, A. I. Liapis, Sep. Technol., 1990, 1, 18
[5] P. Glanz, B. Körner, G. H. Findenegg, *Adsorption Sci. Technol.*, 1984, 1, 41
[6] H. Järvelin, J. R. Fair, *Ind. Eng. Chem. Res.* 1993, 32, 2201
[7] M. Kargol, J. Zajac, D. J. Jones, Th. Steriotis, J. Rozeire, P. Vitse, *Chem. Mater.*, 2004, 16, 3911
[8] E. R. Gilliland, H. L. Bliss, C. E. Kip, *J. Am. Chem. Soc.*, 1941, 63, 2088
[9] (a) Dewar, M. Bull. Soc. Chim. Fr. 1951, 1 8, C79, (b) J. Chatt and L. A. Duncanson, J. Chem. Soc., 1953, 2939 doi:10.1039/JR9530002939 "*Olefin coordination compounds. Part III. Infra-red spectra and structure: attempted preparation of acetylene complexes*", (c) J. Chatt, L. A. Duncanson, L. M. Venanzi, J. Chem. Soc., 1955, 4456-4460 doi:10.1039/JR9550004456 *Directing effects in inorganic substitution reactions. Part I. A hypothesis to explain the trans-effect*, (d) Miessler, Gary L., Donald A. Tarr (2004). *Inorganic Chemistry*. Upper Saddle River, N.J.: Pearson Education, Inc. Pearson Prentice Hall. ISBN 0-13-035471-6., (e) Herrmann/Brauer: *Synthetic Methods of Organometallic and Inorganic Chemistry* Georg Thieme, Stuttgart, 1996
[10] (a) D. L. Peterson, F. Helfferich, R. K. Griep, in: Molecular Sieves p. 217-229 Proc. $1^{st}$ Int. Conf. On Molecular Sieves, London 1967 published by Soc. for Chem. Ind. in 1968. (b) C. M. Shu, K. Kulvaranon, M. E. Findley, A. T. Liapis, *Sep. Sci. Technol.* 1990, 1, 18
[11] (a) Y. Boucheffa, C. Thomazeau, P. Cartraud, P. Magnoux, M. Guisnet, S. Jullian, *Ind. Eng. Chem. Res.* 1997, 36, 3198, (b) H. Järvelin, J. R. Fair, *Ind. Eng. Chem. Res.* 1993, 32, 2201, (c) J. Kärger, D. M. Ruthven, *Diffusion in zeolites*, John Wiley & Sons: New York, 1992, p 104
[12] D. M. Ruthven, S. C. Reyes, *Microp. Mesop. Mater.*, 2007, 104, 59
[13] D. H. Olson, X. Yang, M. A. Camblor, *J. Phys. Chem. B*, 2004, 108, 11044
[14] B. Xiao, P. S. Wheatley, X. Zhao, A. J. Fletcher, S. Fox, A. G. Rossi, S. Bordiga, L. Regli, I. L. Megson, K. M. Thomas and R. E. Morris, *J. Am. Chem. Soc.* 2007, 129, 1203
[15] A. Wagener, M. Schindler, F. Rudolphi, S. Ernst, "Metallorganische Koordinationspolymere zur adsorptiven Trennung von Propan/Propen-Gemischen", *Chem. Ing. Tech.*, 2007, Volume 79, Issue 6, Pages 851-855
[16] U.S. Pat. No. 6,491,740
[17] Serre et al., "A new route to the synthesis of trivalent transition metals porous carboxylates with trimeric SBU", *Angew. Chem. Int. Ed.* 2004, 43, 6286
[18] K. Byrapsa, M. Yoshimura, "Handbook of hydrothermal technology", Noyes Publications, Parkridge, N.J. USA, William Andrew Publishing, LLC, Norwich N.Y. USA, 2001
[19] G. Tompsett, W. C. Conner, K. S. Yngvesson, *ChemPhysChem.* 2006, 7, 296
[20] S.- E. Park, J.- S. Chang, Y. K. Hwang, D. S. Kim, S. H. Jhung, J.- S. Hwang, *Catal. Survey Asia* 2004, 8, 91
[21] C. S. Cundy, *Collect. Czech. Chem. Commum.* 1998, 63, 1699
[22] S. H. Jhung, J.- H. Lee, J.- S. Chang, *Bull. Kor. Chem. Soc.* 2005, 26, 880
[23] A. Pichon, *Cryst. Eng. Comm.* 8, 2006, 211-214
[24] D. Braga, *Angew. Chem. Int. Ed.* 45, 2006, 142-246
[25] D. Braga, *Dalton Trans.*, 2006, 1249-1263.
[26] Rostrup-Nielsen, Catal. Today, 2005, 106:293-296
[27] J. Kärger, D. M. Ruthven, *Diffusion in zeolites*, John Wiley & Sons: New York, 1992, p 104
[28] Patricia Horcajada, Suzy Surblé, Christian Serre, Do-Young Hong, You-Kyong Seo, Jong-San Chang, Jean-Marc Greneche, Irene Margiolaki and Gérard Férey, *Chem Comm*, 2007, 2820: Synthesis and catalytic properties of MIL-100(Fe), an iron(III) carboxylate with large pore
[29] Dziobkowski et al., *Inorg. Chem.* 1982, 20, 671
[30] Anzalone et al., *J. Org. Chem.* 1985, 50, 2128
[31] Ameerunisha et al., *J. Chem. Soc. Perkin Trans.* 2 1995, 1679
[32] Shiotani Akinori, *Z. Naturforsch.* 1994, 49, 1731-1736
[33] Serre et al., "Role of solvent-host interactions that lead to very large swelling of hybrid frameworks", *Science,* 2007, 315, 1828-1831
[34] Serre et al. *J. Am. Chem. Soc.*, 2005, 127, 16273-16278
[35] (a) A. Vimont, J.- M. Goupil, J.- C. Lavalley, and M. Daturi, S. Surblé, C. Serre, F. Millange, G. Férey, N. Audebrand, *J. Am. Chem. Soc.*, 2006, 128, 3218-3227: First characterization of acid sites in a new chromium(III) dicarboxylate with giant pores, (b) A. Vimont, H. Leclerc, F. Mauge, M. Daturi, J. C. Lavalley, S. Surblé, C. Serre and G. Férey, *Journal of Physical Chemistry C,* 111 (2007), 383-388: Creation of Controlled Brønsted Acidity on a Zeotypic Mesoporous Chromium(III) Carboxylate by Grafting Water and Alcohol Molecules
[36] (a) R. B. Eldridge, Ind. Eng. Chem. Res., 1993, 32, 2208, (b) H. Jarvelin, J. R. Fair, *Ind. Eng. Chem. Res.,* 1993, 32, 2201
[37] Suzy Surblé, Christian Serre, Caroline Mellot-Draznieks, Franck Millange, and Gérard Férey: *Chem. Comm.* 2006 284-286: A new isoreticular class of Metal-Organic-Frameworks with the MIL-88 topology
[38] De Weireld, G., Frere, M., Jadot R. *Meas. Sci. Technol.* 10, 117, 1999.
[39] Dreisbach, F., Seif, R., Losch, H. W. *Fundamental of Adsorption* 7, 255, 2002.
[40] Sorensen, O., Rouquerol, J. *Sample Controlled Thermal Analysis*, Kluwer Academic Publishers, 2003.
[41] Battiston A. A. et al., "Reactivity of Fe-binuclear complexes in over-exchanged Fe/ZSM5 studied by in situ XAFS spectroscopy. Part 1: Heat treatment in He and $O_2$", *Journal of Catalysis,* 215, 279-293, 2003.
[42] Magnacca G. et al., "Structural and surface characterization of pure and sulfated iron oxides", *Chem. Mater.,* 15, 675-687, 2003.

[43] (a) Denayer, J. F. M., De Meyer, K., Martens, J. A., Baron, G. V. *Angew. Chem., Int. Ed.* 2003, 42, 2774-2777. (b) Denayer, J. F. M., Ocakoglu, R. A., Arik, I. C., Kirschhock, C. E. A., Martens, J. A., Baron, G. V. *Angew. Chem., Int. Ed.* 2005, 44, 400-403.

[44] U.S. Pat. No. 6,024,781

[45] International publication WO 98/006684

[46] Newalkar, B. L., Choudary, N. V., Turaga, U. T., Vijayalakshimi, R. P., Kumar, P., Komarneni, S., Bhat, S. G. T. Chem. Mater. 2003, 15, 1474

[47] Surblé et al., "A new isoreticular class of metal-organic frameworks with the MIL-88 topology", Chem. Comm., 2006, 284-286

[48] Mellot-Draznieks et al., "Very large swelling in hybrid frameworks: a combined computational and power diffraction study", J. Am. Chem. Soc., 2005, Vol. 127, 16273-16278

[49] Férey et al., "A chromium terephthalate-based solid with unusually large pore volumes and surface area", Science, 2005, Vol. 309, 2040-2042

[50] S. Surblé, F. Millange, C. Serre, T. Düren, M. Latroche, S. Bourrelly, P. L. Llewellyn and G. Férey "MIL-102: A Chromium Carboxylate Metal Organic Framework with Gas Sorption Analysis" *J. Am. Chem. Soc.* 128 (2006), 46, 14890

[51] Y. Liu and al, Angew. Chem. Int. Ed. 2007, 46, 3278-3283

[52] Kosal et al., "A functional zeolite analogue assembled from metalloporphyrins", *Nature*, 2002, 1, 118-121

[53] Dietzel et al., "Hydrogen adsorption in a nickel based coordination polymer with open metal sites in the cylindrical cavities of the desolvated framework", *Chem. Commun.*, 2006, 959-961

[54] P. D. C. Dietzel, R. E. Johnsen, R. Blom, H. Fjellvag, P. Chem. Eur. J., 2008, 14, 2389-2397

[55] P. L. Llewellyn & G. Maurin, C. R. Chimie, 8, 283-302 (2005).

[56] Adriano Zecchina, Mickael Rivallan, Gloria Berlier, Carlo Lamberti, Gabriele Ricchiardi, Phys. Chem. Chem. Phys., 2007, (27), 3483-3499

[57] Philip L. Llewellyn, Sandrine Bourrelly, Christian Serre, Alexandre Vimont, Marco Daturi, Lomig Hamon, Guy De Weireld, Jong-San Chang, Do-Young Hong, Young Kyu Hwang, Sung Hwa Jhung, Gérard Férey "High Uptakes of CO2 and CH4 in Mesoporous Metal Organic Frameworks MIL-100 and MIL-101", Langmuir, 2008, 24, 7245-7250

[58] A. A. Davidov, Infrared Spectroscopy of Adsorbed Species on the Surface of Transition Metal Oxides, Wiley Interscience, 1990 p 123-130 chapter 2

The invention claimed is:

1. A process for separating a mixture of molecules having different unsaturation degrees and/or a different number of unsaturations by preferential adsorption of the molecules with a greater unsaturation degree and/or number of unsaturations on a porous crystalline MOF solid containing reduced metal sites for separating a mixture of molecules having different unsaturation degrees and/or a different number of unsaturations said solid containing a three-dimensional structure of moieties having the following formula (I):

$$M_mO_kX_lL_p \qquad (I)$$

in which:

each occurrence of M independently represents an ion of a transition metal $M^{z+}$ or the reduced form thereof $^{(z-1)+}$ selected from the group consisting of Fe, Mn, Co, Ni and V, and in which z is 3 or 4, provided that the ratio $y=M^{(z-1)+}/M^{z+}$ lies between $0<y\leq x$, where x is the fraction of accessible ions $M^{z+}$ of the MOF solid, m is 1 to 12, k is 0 to 4, l is 0 to 18, p is 1 to 6, X is an anion selected from the group consisting of OH, Cl⁻, F⁻, I⁻, Br⁻, $SO_4^{2-}$, $NO_3^-$, $ClO_4^-$, $PF_6^-$, $BF_4^-$, R—(COO)$_n^-$ where R is as defined below, $R^1$—(COO)$_n^-$; $R^1$—(SO$_3$)$_n^-$ and $R^1$—(PO$_3$)$_n^-$, where $R^1$ is a hydrogen atom, a linear or branched, optionally substituted $C_1$ to $C_{12}$ alkyl and an optionally substituted $C_6$ to $C_{10}$ aryl, where n represents an integer from 1 to 4, L is a spacer ligand comprising a radical R containing q carboxylate groups

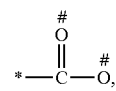

where q is 1, 2, 3, 4, 5 or 6,

\* designates the point of attachment of the carboxylate to the radical R,

\# designates the possible points of attachment of the carboxylate to the metal ion, R represents:

(i) a $C_{1-12}$ alkyl, $C_{2-12}$ alkene or $C_{2-12}$ alkyne radical, (ii) a mono- or polycyclic, fused or non-fused aryl radical, comprising 6 to 50 carbon atoms, (iii) a mono- or polycyclic, fused or non-fused heteroaryl, comprising 1 to 50 carbon atoms, or (iv) an organic radical containing a metallic element selected from the group consisting of ferrocene, porphyrin and phthalocyanine, the radical R optionally being substituted by one or more groups $R^2$, independently selected from the group consisting of $C_{1-10}$ alkyl, $C_{2-10}$ alkene, $C_{2-10}$ alkyne, $C_{3-10}$ cycloalkyl, heteroalkyl, $C_{1-10}$ haloalkyl, $C_{6-10}$ aryl, $C_{3-20}$ heterocycle, $C_{1-10}$ alkyl $C_{6-10}$ aryl, $C_{1-10}$ alkyl $C_{3-10}$ heteroaryl, F, C, Br, I, —NO$_2$, —CN, —CF$_3$, —CH$_2$CF$_3$, —OH, —CH$_2$OH, —CH$_2$CH$_2$OH, —NH$_2$, —CH$_2$NH$_2$, —NHCHO, —COOH, —CONH$_2$—SO$_3$H, —CH$_2$SO$_2$CH$_3$, —PO$_3$H$_2$, or a -GR$^{G1}$ group in which G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, and —C(=S)—, where independently of the other occurrences of $R^{G2}$ each occurrence of $R^{G2}$ is a hydrogen atom; or a linear, branched or cyclic, optionally substituted $C_{1-12}$ alkyl, $C_{1-12}$ heteroalkyl, $C_{2-10}$ alkene or $C_{2-10}$ alkyne group; or a $C_{6-10}$ aryl, $C_{3-10}$ heteroaryl, $C_{5-10}$ heterocycle, $C_{1-10}$ alkyl $C_{6-10}$ aryl or $C_{1-10}$ alkyl $C_{3-10}$ heteroaryl group in which the aryl, heteroaryl or hetero-cyclic radical is optionally substituted, or else, when G represents —NR$^{G2}$—, $R^{G1}$ and $R^{G2}$ together with the nitrogen atom to which they are bound form an optionally substituted heterocycle or heteroaryl, wherein said process comprises:

(i) mixing in a polar solvent:

at least one solution containing at least one inorganic metal precursor present in the form of metal M, a metal salt of M or a coordination complex containing a metal ion of M, at least one ligand L' comprising a radical R containing q groups *—C(=O)—R³, where
* designates the point of attachment of the group to the radical R,
R³ is selected from the group consisting of an OH, an OY, wherein Y is an alkaline cation, a halogen, a radical —OR⁴, —O—C(=O)R⁴ and —NR⁴R⁴', where R⁴ and R⁴' are $C_{1-12}$ alkyl radicals,
to obtain an MOF material,
(ii) activating the MOF material obtained in step (i), wherein said activation is performed under conditions selected from the group consisting of:
at a temperature between 25° C. and 400° C., under a flow of an inert gas selected from the group consisting of helium, argon, nitrogen, and mixtures thereof;
at a temperature between 25° C. and 400° C., under a reducing atmosphere selected from the group consisting of $H_2$, CO, NO, and mixtures thereof;
at a temperature between 25° C. and 400° C., under a reduced pressure ranging from 1 to $10^{-5}$ Pa; and
at a temperature between 25° C. and 300° C., under vacuum or in an inert atmosphere,
thereby providing an activated MOF material in which the pores are accessible for coordination of the molecule to be separated, and in which at least some of the accessible sites are reduced from $M^{z+}$ to $M^{(z-1)+}$ in which the ratio $y=M^{(z-1)+}/M^{z+}$ lies between $0<y \leq x$, where x is the fraction of accessible ions $M^{z+}$ of the MOF solid; and
(iii) placing the MOF material obtained in step (ii) in contact with a mixture of molecules having different unsaturation degrees and/or a different number of unsaturations.

2. The process as claimed in claim 1, wherein step (ii) is a step of reduction of at least some of the metal centers $M^{z+}$ of said MOF material to $M^{(z-1)+}$ ions in which z is 3.

3. The process as claimed in claim 1, further comprising a step (i') of treatment of the MOF material obtained in step (i) with a source of $F^-$ ions.

4. The process as claimed in claim 1, wherein the mixture of molecules is selected from:
a mixture of at least one paraffin and at least one olefin;
a mixture of at least one olefin and one alkyne,
a mixture of acetylene and carbon dioxide; and
a mixture of hydrogen ($H_2$) and carbon monoxide and/or dioxide.

5. The process as claimed in claim 4, wherein the mixture of molecules is a mixture of propane and propene, a mixture of n-butane and isobutene, a mixture of n-butane and butenes, a mixture of acetylene and ethylene, or a mixture of acetylene and carbon dioxide.

6. The process as claimed in claim 1, wherein the mixture of molecules is a mixture of at least one saturated hydrocarbon and at least one unsaturated hydrocarbon or carbon dioxide, and the Brönsted acidity of the MOF material obtained in step (ii) does not trigger polymerization of the unsaturated hydrocarbon.

7. The process as claimed in claim 1, wherein the mixture of molecules is in the gaseous phase.

8. The process as claimed in claim 1, further comprising a step (iv) of desorption of the molecule preferentially adsorbed.

9. The process as claimed in claim 8, wherein the desorption is effected by a desorption technique selected from the group consisting of displacement with an at least 98% pure gas at low pressure, a pressure change, a temperature change and a combination thereof.

10. The process as claimed in claim 1, wherein the ligand L is a di-, tri-, tetra- or hexacarboxylate ligand selected from the group consisting of: $C_2H_2(CO_2^-)_2$ (fumarate), $C_2H_4(CO_2^-)_2$ (succinate), $C_3H_6(CO_2^-)_2$ (glutarate), $C_4H_4(CO_2^-)_2$ (muconate), $C_4H_8(CO_2^-)_2$ (adipate), $C_5H_3S(CO_2^-)_2$ (2,5-thiophenedicarboxylate), $C_6H_4(CO_2^-)_2$ (terephthalate), $C_6H_2N_2(CO_2^-)_2$ (2,5-pyrazine dicarboxylate), $C_7H_{16}(CO_2^-)_2$ (azelate), $C_{10}H_6(CO_2^-)_2$ (naphthalene-2,6-dicarboxylate), $C_{12}H_8(CO_2^-)_2$ (biphenyl-4,4'-dicarboxylate), $C_{12}H_8N_2(CO_2^-)_2$ (azobenzenedicarboxylate), $C_{12}H_6Cl_2N_2(CO_2^-)_2$ (dichloroazobenzenedicarboxylate), $C_{12}H_6N_2(CO_2^-)_4$ (azobenzenetetracarboxylate), $C_{12}H_6N_2(OH)_2(CO_2^-)_2$ (dihydroxo-azobenzenedicarboxylate), $C_6H_3(CO_2^-)_3$ (benzene-1,2,4-tri-carboxylate), $C_6H_3(CO_2^-)_3$ (benzene-1,3,5-tricarboxylate), $C_{24}H_{15}(CO_2^-)_3$ (benzene-1,3,5-tribenzoate), $C_{42}H_{27}(CO_2^-)_3$ (1,3,5-tris[4'-carboxy(1,1'-biphenyl-4-yl)benzene), $C_6H_2(CO_2^-)_4$ (benzene-1,2,4,5-tetracarboxylate, $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2^-)_4$ (biphenyl-3,5,3',5'-tetracarboxylate, and the modified analogs selected from the group comprising 2-amino-terephthalate, 2-nitroterephthalate, 2-methylterephthalate, 2-chloroterephthalate, 2-bromoterephthalate, 2,5-dihydroxoterephthalate, 2,5-diperfluoroterephthalate, tetrafluoroterephthalate, 2,5-dicarboxyterephthalate, dimethyl-4,4'-biphenyldicarboxylate, and tetramethyl-4,4'-biphenyldicarboxylate and dicarboxy-4,4'-biphenyldicarboxylate.

11. The process as claimed in claim 1, wherein the anion X is selected from the group consisting of $OH^-$, $Cl^-$, $Br^-$, $F^-$, $R-(COO)_n^-$, $PF_6^-$, $NO_3^-$, $SO_4^{2-}$ and $ClO_4^-$, with R and n as defined in claim 1.

12. The process as claimed in claim 1, wherein said mixture of molecules is selected from the group consisting of:
a mixture of at least one saturated hydrocarbon and at least one unsaturated hydrocarbon,
a mixture of at least one compound containing one or more free electron pair(s) and at least one compound not containing a free electron pair, and
a mixture of hydrogen ($H_2$) and carbon monoxide and/or dioxide.

13. The process as claimed in claim 12, wherein the mixture of hydrocarbons is a mixture of propane and propene, a mixture of n-butane and isobutene, a mixture of n-butane and butenes, a mixture of acetylene and ethylene or a mixture of acetylene and carbon dioxide.

14. The process as claimed in claim 1, wherein M is Fe, z is 3 and the ratio $y=M^{(z-1)+}/M^{z+}$ lies between $0<y \leq 1/3$.

15. The process as claimed in claim 1, wherein the MOF solid contains a three-dimensional succession of moieties having formula (I) selected from the group consisting of:
$M_3OX[C_6H_3(CO_2)_3]_2$ (structure of MIL-100 type);
$M_3OX[C_6H_4(CO_2)_2]_3$ (structure of MIL-101 type);
$M_3OX[C_6(CH_3)_4(CO_2)_2]_3$ (structure of MIL-88B_4CH₃ type);
$M_6O_2X_2[C_{10}H_2(CO_2)_4]_3$ (structure of MIL-102 type); and
$Fe_6O_2[C_{12}H_6N_2-(CO_2)_4]_3 \cdot X_2 \cdot nH_2O$ (structure of MIL-127 type),
in which M is selected from Fe, Mn, Co, and X is as defined in claim 1.

16. The process as claimed in claim 15, wherein M is Fe.

* * * * *